US012453826B2

(12) United States Patent
Ahern et al.

(10) Patent No.: US 12,453,826 B2
(45) Date of Patent: Oct. 28, 2025

(54) INHALER DEVICE

(71) Applicant: SANDOZ AG, Basel (CH)

(72) Inventors: David Gregory Ahern, Cambridge (GB); Robin Craig Cocker, Cambridge (GB); Ewen Humphrey Christie, Cambridge (GB); Christopher Iain Davidson, Cambridge (GB); James Anthony Tibbatts, Cambridge (GB); Paul Christopher Edward Mutti, Cambridge (GB); James Terence Collins, Cambridge (GB)

(73) Assignee: Sandoz AG, Basel (CH)

( * ) Notice: Subject to any disclaimer, the term of this patent is extended or adjusted under 35 U.S.C. 154(b) by 1140 days.

(21) Appl. No.: 17/264,404

(22) PCT Filed: Aug. 2, 2019

(86) PCT No.: PCT/GB2019/052184

§ 371 (c)(1),
(2) Date: Jan. 29, 2021

(87) PCT Pub. No.: WO2020/025977

PCT Pub. Date: Feb. 6, 2020

(65) Prior Publication Data

US 2021/0386945 A1 Dec. 16, 2021

(30) Foreign Application Priority Data

Aug. 3, 2018 (GB) ..................................... 1812671

(51) Int. Cl.
*A61M 15/00* (2006.01)

(52) U.S. Cl.
CPC .... *A61M 15/0045* (2013.01); *A61M 15/0025* (2014.02)

(58) Field of Classification Search
CPC .......... A61M 15/0045; A61M 15/0025; A61M 15/00; A61M 15/0031; A61M 15/0041; A61M 15/0051; A61M 11/00
See application file for complete search history.

(56) References Cited

U.S. PATENT DOCUMENTS 4,627,432 A 12/1986 Newell et al.
5,590,645 A 1/1997 Davies et al.
(Continued)

FOREIGN PATENT DOCUMENTS

EP 1651296 5/2006
EP 2082761 7/2009
(Continued)

OTHER PUBLICATIONS

International Search Report for International Application No. PCT/GB2019/052184, dated Nov. 12, 2019, 6 pages.
(Continued)

*Primary Examiner* — Justine R Yu
*Assistant Examiner* — Matthew R Moon
(74) *Attorney, Agent, or Firm* — Luedeka Neeely, P.C.

(57) ABSTRACT

Inhaler devices are disclosed (701), and in particular inhaler devices provided with medicament carriers containing individual pockets or blisters of powdered medicament covered by a lidding sheet such as a lidding foil. A common actuator (710) is provided for controlling movement of an indexing system (712,714) for advancing/indexing a dose and an opening system (790,791) for opening a dose such that progression of the opening system (790,791) is disproportional to progression of the indexing system (712,714) during movement of the common actuator (710).

22 Claims, 45 Drawing Sheets

(56) References Cited

U.S. PATENT DOCUMENTS

| | | | |
|---|---|---|---|
| 7,434,579 B2 | 10/2008 | Young et al. | |
| 8,511,304 B2 | 8/2013 | Anderson et al. | |
| 8,746,242 B2 | 6/2014 | Connell et al. | |
| 8,931,479 B2 | 1/2015 | Keegstra | |
| 2004/0244794 A1 | 12/2004 | Richards | |
| 2006/0196504 A1 | 9/2006 | Augustyn et al. | |
| 2009/0139516 A1* | 6/2009 | Augustyn | G06M 3/025 128/200.23 |
| 2012/0291782 A1* | 11/2012 | Bowman | A61M 15/0045 128/203.15 |
| 2013/0152928 A1 | 6/2013 | Kirniak | |
| 2019/0015608 A1* | 1/2019 | Glusker | A61M 15/0028 |
| 2019/0307975 A1* | 10/2019 | Gupta | A61M 15/0048 |

FOREIGN PATENT DOCUMENTS

| | | | |
|---|---|---|---|
| GB | 2407042 | A | 4/2005 |
| JP | 2005515039 | A | 5/2005 |
| JP | 2015037466 | A | 2/2015 |
| WO | 03061743 | A1 | 7/2003 |
| WO | 2007012871 | A1 | 2/2007 |
| WO | 2017203021 | | 11/2017 |
| WO | 2017203021 | A1 | 11/2017 |

OTHER PUBLICATIONS

UKIPO Search Report for Application No. GB1812671.4, dated Mar. 20, 2019, 4 pages.

UKIPO Search Report for Application No. GB1812671.4, dated Jul. 31, 2019, 2 pages.

* cited by examiner

INHALER DEVICE

REFERENCE TO RELATED APPLICATION

This application is a U.S. National Phase filing of International Application No. PCT/GB2019/052184, filed Aug. 2, 2019, which relates and claims priority to Great Britain Application No. 1812671.4 filed Aug. 3, 2018, the entirety of each of which are hereby incorporated by reference in their entirety.

BACKGROUND OF THE INVENTION

The present invention relates to inhaler devices, in particular to devices provided with medicament carriers containing individual pockets or blisters of powdered medicament covered by a lidding sheet such as a lidding foil.

Delivery of drugs in aerosol form to the airways using an inhalation device is a well-known and effective method of treating diseases such as asthma and Chronic Obstructive Pulmonary Disease (COPD). The aerosol can either be in liquid or powder form.

Dry powder devices often use the patient's inhalation air flow to aerosolize and deliver the dry powder drug. One benefit of this is that a user need not coordinate inspiration with another action, for example depressing a canister or pressing a button to release a propellant.

Various different types of dry powder inhaler are known.

A first group of devices holds the powdered drug in a reservoir and meters the dose prior to delivery. These devices often suffer from poor accuracy of dose metering and it can be difficult to protect the bulk powder from moisture.

Also known are pre-metered dry powder devices, in which accurate dose metering is carried out as part of the manufacturing process and each dose is independently protected from moisture.

The individual doses used in pre-metered devices are typically held in either a gelatine capsule or a foil blister. Capsule based inhaler devices can be simple and low-cost, but typically require the patient to load the inhaler with a capsule prior to each use. The environmental protection provided by the capsule is also not particularly effective. This generally necessitates the use of secondary, foil-based packaging, adding to the number and awkwardness of the steps in the use-sequence.

Blister devices tend to provide better environmental protection due to the aluminium foil used in their construction. They can also be more convenient for users, because a blister pack can contain several doses, ideally enough for a month's usage.

Since most current drugs for asthma or COPD are used once or twice a day, this means an inhaler should be able to contain 30 or 60 doses. To enable these doses to be packaged into a conveniently sized device, the blisters may be configured into a disk form or an elongate strip form. The individual blisters need to be opened before inhalation takes place, so that when the patient inhales the powdered drug is entrained in the patient's inspiratory airflow and carried out of the device into the patient's lungs. Before, after, or during each inhalation, the pack must be also indexed by one blister so that the previously emptied blister is replaced by a fresh blister.

Various means of opening blisters and indexing are known from the prior art.

U.S. Pat. No. 4,627,432 describes an inhaler device that uses a blister pack in disk form. The doses are arranged in a circular pattern, with each disk containing 8 blisters. A plunger is used to pierce each blister and enable the drug therein to be inhaled. A separate indexing mechanism rotates the disk to move a fresh blister into place.

Although mechanically simple, a problem with this device is that the number of doses is limited to eight in order to keep the device small in size and simple in operation. Configuring a disk-based device to contain 30 or 60 doses and still be of acceptable size requires modification of the pocket-shape, or a significantly more complicated device with either multiple disks, or dose cavities formed in (for example) concentric rings or a spiral pattern.

This problem can be partially addressed by providing a similar device with blisters in an elongate strip form. The elongate strip can be coiled within an inhaler device to minimise the necessary packaging space. Separate indexing and piercing mechanisms can be provided, or a single actuating lever may be provided to first index the blister-strip and then pierce the blister, preparing it for inhalation.

A drawback that applies to blister-strip devices such as described so far, is that the action of piercing a blister tends to involve a piercing element that occupies and partially obstructs the blister. As a result, pierceable blisters typically need to be 2 or 3 times larger than the required dose volume in order to provide space for the piercer and to allow the drug to move freely and be entrained in the airflow.

An alternative approach is to use a blister-strip with a peelable lid, the inhaler device peeling the lid of each blister in turn prior to each inhalation. The mechanism for such inhalers is typically more complex, since it needs to manage both the used base sheet/foil and the used lid sheet or lidding foil. However, because no piercer is entering the blister, and because the lid is removed completely, the blister need only be big enough to contain the powdered drug. Smaller blisters can therefore be used for a given dose size.

A well-known peelable strip device is shown in U.S. Pat. No. 5,590,645. The device contains a coil of sealed blisters, a coil of used base sheet and a separate coil of used lid sheet. The base and lid sheets are separated at an opening station, where the lid is peeled back from the base as the strip is indexed. Thus, all three coils move simultaneously. The main strip driver is a drum incorporating recesses that engage with the blisters in the base sheet, while the base and lid sheet coils are also driven to ensure that the used strips are coiled after use. The used base sheet/foil is loosely wound, while the used lid sheet is tightly coiled such that the tension needed to ensure separation from the base sheet is maintained.

A variant of this device that incorporates two blister-strips indexed and opened in the same way is shown in U.S. Pat. No. 8,511,304B. The two strips are arranged so that when opened two fresh blisters lie either side of a single airway manifold. Thus, the contents of both blisters can be inhaled simultaneously. The potential advantage of this is that two separate drugs or drug combinations can be stored in separate blisters yet inhaled together.

One significant use error that can occur in peelable strip devices arises from the blisters being opened as the strip is indexed, rather than in a separate action as with most pierceable blister devices. Typically, the user-input in such devices is linked directly to a set of components that simultaneously index and peel the strip to present an open blister-pocket up to the airway for the user to inhale. As a result, blister opening can occur when the actuating mechanism is only partially moved. This is a particular problem in devices where the actuating mechanism is driven by a mouthpiece cover of the device rather than by a separate actuation lever. If the patient part opens the cover, for example to inspect or clean the mouthpiece, then the blister may be partially or completely opened thus exposing the blister contents to environmental moisture. A user may then return the mouthpiece cover to its unopened position without being aware of the potential degradation of the now-exposed formulation. Subsequent complete opening of the cover and inhalation risks inhalation of a compromised dose. Even if a user becomes aware of the premature opening of a blister and rejects the associated dose, the dose will be wasted.

The problem can be mitigated by providing an inhaler with a breath-actuation mechanism so that actuation of a lever or mouthpiece cover indexes a blister strip, but individual blisters are only opened on inhalation be a user. U.S. Pat. No. 7,434,579, for example, discloses a device with a strip comprising a base sheet and lid sheet permanently sealed to each other, and a further tear sheet glued to the lid sheet locally above each blister cavity such that it is able to tear a portion of the lid sheet away from the rest of the blister. When the device is actuated the blister-strip is indexed but no tension is applied to the lid tear sheet until a breath-actuated trigger releases a spring that drives the lid tear sheet coiling mechanism. Although effective, the inclusion of a breath-actuation mechanism adds significant complexity to the inhaler device, and the tear-strip feature is non-standard in blister strip manufacture.

One alternative approach, as discussed in U.S. Pat. No. 8,746,242B, is to provide a delayed actuation mechanism, ie a mechanism where initial movement of a mouthpiece cover does not actuate the indexing and opening mechanism. By delaying the actuation, the likelihood of accidental actuation is reduced. However, it is still possible for an incomplete opening of the cover to partially actuate the device.

There is therefore a need for an improved inhaler device, suitable for use with one or more medicament carriers, that has a simple means of enabling the actuating lever or cover to be moved by the patient without accidentally opening blisters to expose the medicament. Ideally the lever or cover should be reversibly movable through most of its travel, with the point at which blister opening happens being close to the end of the actuation movement and clearly identifiable by the patient.

It is an aim of the present invention to provide such an inhaler device, which mitigates or overcomes some or all of the abovementioned problems while ideally being suitable for use with conventional medicament carriers such as standard blister strips.

BRIEF SUMMARY OF THE INVENTION

According to a first aspect of the invention there is provided an inhaler device as defined in the appended claim 1. Further optional features are recited in the associated dependent claims.

A further aspect of the invention provides an inhaler device.

The invention disconnects, or at least partially separates, the indexing and peeling operations during use of an inhaler device. For example, it allows the start of indexing and the start of peeling to occur at different times, and/or it allows one or more particular points in the peeling operation(s) (for example, a point at which the dose or doses are considered to be compromised, such as the point when the dose-pocket (s) begins to open) to be delayed until a more desirable point in the actuation of the device, without the indexing operation (s) necessarily being similarly delayed.

The user's input to the device, for example closing and/or opening the cap or operating a lever/button, can be used to first initiate indexing of the medicament carrier(s), and then to initiate peeling of the lidding sheet/foil(s) from individual blister(s) to present the formulation to the airway.

The invention therefore allows the user to open the device up to a desirable 'commitment' point without initiating peeling of the lidding sheet/foil(s), or at least without exposing a blister-pocket of formulation. This means that there is less chance of wasted doses, and less chance of inhalation of degraded formulation.

The commitment point will generally be arranged at or near the end of actuator operation, for example at or adjacent the end of motion during mouthpiece opening. However, it may be provided at any point after the indexing operation has commenced. For example, the operation of peeling open an individual blister of a medicament carrier may coincide or overlap with a portion of the indexing operation.

There are known devices that use a series of geared components to deliver Active Pharmaceutical Ingredient (API) from two distinct blister-strips.

A simple mechanical solution when designing a strip-based device of this type, is to link the user input (usually either a lever/button, or the cap of the device) directly to a set of components that simultaneously index and peel the blister strip. The individual doses or blisters in one or more blister strips are thereby peeled and presented to a single/common airway for the user to inhale.

One common flaw with this system is that part-opening the cap (or part-depressing the lever/button) will partially advance a dose, and partially or fully open the associated blister-pocket. Release or return of the actuator can then cause the blister to be returned to its 'unpeeled' position, or left in the position that it has reached, without the user being informed of the potential degradation of the now-exposed formulation.

This problem could be solved by charging a spring and releasing it at the end of cap-open or lever operation, simultaneously effecting indexing and peeling of the strip. However, this requires a very strong spring, not least because the force required to index a strip will be potentially variable if it snags within the device. This increases the required input force, and negatively impacts on user 'feel' or feedback during use of the device.

Another known solution is to delay the initiation of the operation (index and peel) until partway through the cap-open/actuation sequence. However, this reduces the range of motion across which the user can input the required energy to the system (the user must input all of the required energy in a single section of cap-opening or lever-operation), which causes similar problems to the incorporation of a strong spring as discussed above.

In the system according to the present invention, a relevant part of the operation of peeling, for example the part or phase of the operation that exposes a dose ready for inhalation, can be delayed relative to the initiation of an indexing operation. In more general terms, at least part of the operation of peeling is delayed relative to the equivalent part of the indexing operation. For example, the initiation of peeling may be delayed relative to the initiation of indexing, and/or the point at which the peeling operation has been progressed by 30% may be delayed relative to the point at which the indexing operation has been progressed by 30%, etc. The point at which a dose is exposed may be delayed until the latest possible moment during cap-open or operation of an alternative actuator.

With conventional systems, indexing and peeling can only be achieved simultaneously. The operations of peeling and indexing are mechanically linked so that their progression is substantially proportional, and delaying one with respect to the other as described above is impossible. By dissociating or separating the two actions, disproportional movement of the indexing and peeling components/systems becomes possible from a single actuator. The benefits of a delayed peel operation can thus be combined with a smoother user experience and improved feedback, because indexing of the device can still take place across the entire operation of an actuator.

Significant development work was required to provide solutions to the problem of delaying at least the part of the 'peel' operation that opens or exposes a dose for inhalation, and uncoupling or dissociating this from the indexing of the inhaler device. The solutions can be broadly categorised as one of two main approaches: either regulation—i.e. absence or reduction, to some degree—of tension in the lidding sheet at the peel-front below the level of tension required for peeling, or maintenance of peel-front position relative to the medicament carrier through the use of a moving 'peel-beak'.

Regulation of Tension in the Lidding-Sheet

This involves initially indexing the medicament carrier under a position that the airway occupies during inhalation, with the peel-front (i.e. the location at which a lidding sheet or foil is removed from the medicament carrier) substantially moving with the next unopened blister of the medicament carrier. For example, the peeled lidding sheet may be folded back on top of the unopened blister(s) in the medicament carrier during initial indexing. A lidding sheet take-up system is then actuated or allowed to apply tension at the specified point in the operation of the actuator, peeling the lidding sheet under the airway and exposing the open blister to the airway.

Because there is nothing actively maintaining the position of the peel front (the line of peeling separation) in this embodiment, the tension on the lidding sheet should not be applied, or should be released, or 'backed off', during the indexing operation to ensure that peeling does not occur until the desired moment.

Moving Peel-Beak

This option involves the use of a specific component (per medicament carrier) that substantially travels with the medicament carrier, keeping the peel-front substantially stationary relative to the medicament carrier during indexing. This moving/movable peel-beak then moves relative to the medicament carrier, at a desirable point, allowing peeling/opening of a desired number of blisters/pockets. For example, the peel-beak may be released, allowing tension in the lidding sheet to pull it back and thus effect peeling.

In some instances, including a moving peel-beak can create an associated problem that may need to be addressed. The space that the peel-beak must sweep through can result in a gap being provided between the newly-peeled blister and the airway. This can be solved in a variety of ways, including, but not limited to:

- Moving part or all of the airway—the airway can move into the gap between it and the medicament carrier (previously occupied or swept through by the peel-beak); this can be achieved in a number of ways:
  - Combined peel-beak and airway-section—the moving peel-beak component can include, or be attached to, a (possibly straight) section of airway (for example, an extra section of airway, or the entire airway) that moves (for example, rotates or translates) with the peel-beak to fill the gap previously occupied or swept through by the peel-beak;
  - Separate moving airway—a section of airway (for example, an extra section of airway, or the entire airway) can move (for example, rotate or translate, or some other more complex movement) towards the medicament carrier after/as the peel-beak effects/allows peeling, closing the gap that the peel-beak has previously occupied or swept through.
- Moving medicament carrier—the medicament carrier can be moved (for example, translated) towards the airway after/as the peel-beak rotates, for example by the indexing component or another component, closing the gap that the peel-beak has previously occupied or swept through.

The peel-beak movement and the movement of the indexing component may be linked by a single component or mechanism, or may be driven simultaneously.

Both the peeling under the inhalation position of the airway option and the moving peel-beak option generally require that the lidding sheet take-up system is capable of allowing the peel-front to substantially move with the medicament carrier.

One way of achieving this is to situate the lidding sheet take-up system in a place where the distances between the take-up system and the start and end position of the peel-front (during peeling) are substantially the same. For example, the take-up system could be situated on (or near) the perpendicular bisecting line of the peel-front's movement. Similarly, this effect could be achieved by situating the lidding sheet take-up system in a place where the distance between the take-up system and the start position of the peel-front (at the commencement of peeling) is greater than the distance between the take-up system and the end position of the peel-front (at the conclusion of peeling). For example, the take-up system could be situated past (ie on the opposite side to the peel-front's start-position) a line that is both perpendicular to a line struck through the peel front's start position and end position, and struck through the peel-front's end position, it will only be required to operate (ie take up lidding sheet/foil) uni-directionally.

An alternative approach is to design the lidding sheet take-up system to be capable of 'releasing' some lidding sheet, for example one index-length of lidding sheet (the length of lidding sheet/foil associated with a single index step or dose). This requires the extra take-up of this released length of lidding sheet when the peeling event occurs, for example a length of lidding sheet equal to two index-lengths in total. Conventional take-up systems are unidirectional, and do not envisage the need to release tension and/or run in reverse. Providing this functionality can be achieved in various ways. Some examples are provided below.

Sprung Tension

Where a moving peel-beak is provided, a spring element may be incorporated in the drive-train of the take-up system. The system will then automatically allow some lidding sheet to be released under sufficient tension from the indexing system. This forced release will generate extra spring potential energy, which will in turn effect the extra take-up required during peeling. The sprung biasing may be provided in various ways, for example:

- Sprung take-up drum or other take-up system (such as a coil spring incorporated into a take-up drum or hub);
- A sprung compound gear or other sprung element elsewhere in the drive-train;
- A lidding sheet material that can be elastically deformed to store energy; or Spring-induced tension in the lidding sheet, for example:
- One or more sprung tensioners acting on the lidding sheet
- A take-up system sprung away from the peel-beak, for example a take-up drum mounted on a sprung arm.

Spring-induced tension in the lidding sheet may be combined with active movement of the tensioning component, allowing the system to reduce the maximum force experienced by the lidding sheet/spring(s).

In known systems, the inclusion of a spring in the drive train of the take-up system has been purely to compensate for the growing diameter of a take-up drum as used sheet is wound on during use. Springs have not previously been considered as a means of allowing the take-up system to run in reverse during indexing.

Controlled Tension

This approach involves actively controlling (for example, reducing or releasing) the tension in the lidding sheet a sufficient amount to allow the peel-front to move substantially with the medicament carrier by the required amount to avoid substantial or undesirable peeling. There are several ways in which this can be achieved, including:
- Take-up system movement—moving a take-up system (usually a take-up drum), for example translating it towards the peel-front by one index-distance, allowing the release or movement of enough lidding sheet for the peel-front to move by the same distance;
- Take-up system reverse—releasing a clutch or similar mechanism, for example disengaging the take-up system's ratchet-set, or actively reversing the take-up system by the required amount (for example mounting the take-up drum on a ratchet wheel that is turned by the appropriate angle to allow sufficient lidding sheet slackening, and then turned back in the opposite direction during peeling);
- Tensioner release—removing or moving a tensioning member from the lidding sheet tension-path, allowing the sheet to straighten out partially or fully, to the extent that some distance of the sheet (for example, one index-distance) is released to allow the peel-front to substantially move with the strip; or
- Keeping the strip and peel-front substantially stationary during indexing—effecting indexing without moving the strip or the peel-front, for example rotationally indexing the strip the required distance with an index wheel while moving the index wheel towards the take-up system by the same distance, effectively keeping the strip and peel-front stationary.

Another advantage of separating indexing and peeling is that it allows some of the device's operations, such as indexing one or both wheels in a dual-strip device, to be carried out during cap-close (or another analogous reverse operation of the actuator). The required user input can then be distributed over an even greater range of motion, ie over more than one section of actuator operation, to further reduce the required force and further smooth operation.

The inhaler device according to the first aspect comprises an actuation mechanism having an indexing system for advancing a medicament carrier comprising a base with a plurality of medicament pockets or blisters and a peelable lidding sheet, such as a lidding foil, covering the blisters, an opening system for peeling the lidding sheet from the medicament carrier to open a blister, and a common actuator for the indexing system and the opening system, wherein the common actuator is movable between a first position and a second position via an intermediate position, and wherein progression of the opening system is disproportional to progression of the indexing system during movement of the common actuator.

In use, movement of the common actuator through a single defined range of motion causes movement or progression of the indexing system sufficient to advance a medicament carrier by a single dose and movement or progression of the opening system sufficient to completely remove the lidding sheet from a corresponding length of the medicament carrier, but the movements of the opening system and of the indexing system are not proportional. In other words, the speed ratio or percentage of total movement/progression of the opening system and indexing system are not constant during operation of the inhaler device.

Movement of the common actuator through a first range of motion may cause operation of the indexing system and movement of the common actuator through a second range of motion causes operation the opening system, and the indexing system may be dissociated (eg decoupled or separated) from the opening system so that said first range of motion is not the same as said second range of motion. The dissociation of the opening system and indexing system enables one to move largely independently of the other so that their movement need not be proportional, as in the prior art.

A defined movement of the common actuator may operate both the indexing system and the opening system, and the speed of movement of the opening system relative to the speed of movement of the actuator may vary during said defined movement of the actuator.

Alternatively, a defined movement of the common actuator may cause operation of the indexing system to advance one dose of medicament and cause the opening system to move through a first phase of operation in which said peeling occurs without exposing medicament in a blister and a second phase of operation in which medicament in a blister is exposed by said peeling, to thereby present a dose of medicament ready for inhalation, and said second phase of operation of the peeling system may be delayed until said operation of the indexing system is 30% complete. Some peeling of the lidding sheet may take place early in the operation of a device, but a critical part of the operation, when a sheet is peeled over the edge of a blister pocket and a medicament is actually exposed, is delayed until later in the operation.

The second, or critical, phase of operation of the opening system may be delayed until said operation of the indexing system is 50% complete, or 60%, 70%, 80%, 90%, 95% or 100% complete.

The dose of medicament may be defined as the dose to be delivered by the inhaler device according to a particular dosage regime. This may comprise the contents of a single blister, or a pair of blisters, or more as required.

The defined movement may be movement from the first position to the second position, or movement from the second position to the first position and back to the second position, for example.

Movement of the common actuator from said first position, for example any movement away from the first position, may advance the indexing system, and only movement of the actuator beyond the intermediate position may actuate the opening system.

Reverse movement of the actuator from a position between said first position and said intermediate position back to said first position may result in reversing of said advancement of the indexing system. This helps to avoid partially advancing and/or exposing doses during incorrect or incomplete actuation of the inhaler device. An actuator can be moved up to a point, for example the point of peeling or exposure of a dose, and then returned to its initial position without leaving a dose partially advanced or exposed. The next 'correct' or full operation of the inhaler device is, therefore, not compromised by an incorrect or incomplete actuation. This is particularly relevant where indexing begins immediately on movement of the actuator.

Movement of the actuator between the second position and the first position, i.e. in a direction moving from the second position towards the first position, may also result in advancement of the indexing system.

The inhaler device may further comprise a central hub driven by the actuator.

The inhaler device may further comprise a gear linkage or a cam system, for example a cam plate, to transmit drive from the hub to the index system.

The actuation mechanism may further comprise a trigger component, movement of which triggers the opening system. The trigger component may be a linearly moving component such as a push rod or slider for releasing a sprung biased component within the opening system.

Movement of the common actuator past the intermediate position may result in movement of the trigger component.

The actuation mechanism may further comprise a cam for controlling the opening system.

The actuation mechanism may further comprise a lidding sheet take-up component for receiving used lidding sheet peeled from a medicament carrier, and a drivetrain between the common actuator and the lidding sheet take-up component. The drive train may comprise the central hub.

The actuation mechanism may comprise means for regulating tension generated in a lidding sheet during advancing of the indexing system. The system may be active (eg driven) or passive allow minimal tension in a lidding sheet when the device is left or stored with the actuator in the first position.

A torsion spring may be provided between two rotating components provided on a common centre in the drivetrain. For example, a torsion spring may be provided between two stacked gears in a geared drivetrain. The two rotating components may be within a central logic hub, or within a further driving element within the drivetrain, or may form a sprung idler.

The torsion spring is charged due to tension in the used lidding sheet during advancing of the indexing system. This may provide a form of passive tension regulation in a lidding sheet.

The drivetrain may actively move, for example rotate, the lidding sheet take-up component to regulate tension in the lidding sheet, for example reduce tension or create slack in a lidding sheet, before or during advancing of the indexing system.

At least some of the peeled lidding sheet, for example slack generated by active tension regulation, may be turned back over an unopened section of a medicament carrier during advancing of the indexing system.

The inhaler device may further comprise a peel-beak component for regulating separation of a lidding sheet from a medicament carrier. The peel-beak component may, in particular, resist peeling/separation of a lidding sheet at a location on the medicament carrier which is adjacent the peel-beak in use.

The peel-beak component is movable during or before advancement of the indexing system. For example, the peel-beak may move with a component of the indexing system during indexing The peel-beak component may follow a path substantially coincident with or offset from the path of a medicament carrier.

The peel-beak component may selectively engage with a component of the indexing system, for example with a moving indexer such as an index wheel.

The peel-beak component may comprise a pawl or ratchet that selectively engages with said component of the indexing system.

The indexing system may comprise means for indexing first and second medicament carriers each comprising a base with a plurality of medicament pockets or blisters and a peelable lidding sheet covering the blisters. Means may be provided for advancing more than two medicament carriers.

The opening system may be configured for peeling the lidding sheet from each of the first and second medicament carriers, and movement of the common actuator from said first position may result in operation of the indexing system to advance the first medicament carrier, but only movement of the actuator beyond the intermediate position may result in actuation of the opening system to peel the lidding sheet from a blister of the second medicament carrier.

The indexing system may comprise separate first and second indexers for indexing said first and second medicament carriers.

The indexing system may advance the first and second indexers disproportionally, i.e. such that the progression of the first indexer is disproportional to the progression of the second indexer.

An inhaler device is also provided comprising an actuation mechanism having an indexing system comprising first and second indexers for advancing first and second medicament carriers, and a common actuator for the first and second indexers, wherein the common actuator is movable between a first position and a second position via an intermediate position, and wherein progression of the first indexer is disproportional to progression of the second indexer. The progression may take place during or after movement of the common actuator, for example the progression may be driven by a spring force released after movement of the actuator is complete.

The first indexer and the second indexer may, in particular, not be advanced simultaneously during movement of the common actuator, ie their movement may be mutually exclusive.

Movement of the common actuator through a first range of motion may cause operation of the first indexer and movement of the common actuator through a second range of motion causes operation the second indexer, and the first indexer may be dissociated from the second indexer so that said first range of motion is not the same as said second range of motion.

The indexing system may advance one of the first and second indexers as the common actuator is moved from said second position to said first position.

At least one, and possibly both, of the first and second indexers may comprise an index wheel.

The indexing system may alternatively comprise a single indexer, which may comprise an index wheel.

The or each index wheel may be rotatable to advance a medicament carrier in the form of a blister strip, and may comprise cavities for receiving individual blisters of the blister strip.

The opening system may be configured to simultaneously peel open a blister on each of said first and second medicament carriers.

Said intermediate position of the common actuator may be closer to said second position of the common actuator than to said first position of the common actuator. For example, the intermediate position may be within the final 45%, 35%, 25%, 20% or 15% A of the total movement between said first and second positions, or of a full range of movement of the common actuator.

Said intermediate position of the common actuator may be adjacent said second position of the common actuator, for example within 0-10% of the said movement of the common actuator, and/or within 10° where the actuator moves in an arc.

The actuation mechanism may comprise one or more gears with intermittent drive and/or locking surfaces. This enables intermittent drive and/or locking of the elements of the actuation system (eg lidding sheet take-up components, individual indexers, moving peel-beaks, etc) during use.

The indexing system may comprise locking means for selectively preventing movement of one or more components, for example one or more indexers/index wheels, of the indexing system.

The locking means may comprise one or more gears with locking surfaces, to provide a Geneva lock, and/or one or more pawls.

The actuator may comprise a mouthpiece cover, and the first position may be a fully closed position of the mouthpiece cover, i.e. a position of the mouthpiece cover in which a mouthpiece of the inhaler is fully covered. The second position may be a fully open position of the mouthpiece cover, i.e. a position of the mouthpiece cover in which a mouthpiece of the device is fully uncovered.

Alternatively, the actuator may comprise a separate lever, button or other actuator, and the first and/or second positions may be defined stop positions of the actuator.

The inhaler device may further comprise a movable airway component, either as a unitary movable airway or as part of a split airway comprising a stationary airway component and the movable airway component. The movable airway component provides a peel-beak component for regulating separation of a lidding sheet from a medicament carrier.

The movable airway component may follow a path that is not substantially coincident with or merely offset from the path of a medicament carrier. For example, the movable airway component may follow a substantially linear path. A medicament carrier may, for example, follow a curved or circular path.

This invention can be employed in a device containing one or more medicament carriers, to release formulation for inhalation by the user in a mechanically advantageous fashion, while minimising the risk of accidental exposure of the formulation to the environment through unintended peeling.

Wherever practicable, any of the essential or preferable features defined in relation to any one aspect of the invention may be applied to any further aspect. Accordingly, the invention may comprise various alternative configurations of the features defined above.

BRIEF DESCRIPTION OF THE DRAWINGS

Practicable embodiments of the invention are described in further detail below by way of example only with reference to the accompanying drawings, of which.

DETAILED DESCRIPTION OF THE INVENTION

Figure 1:
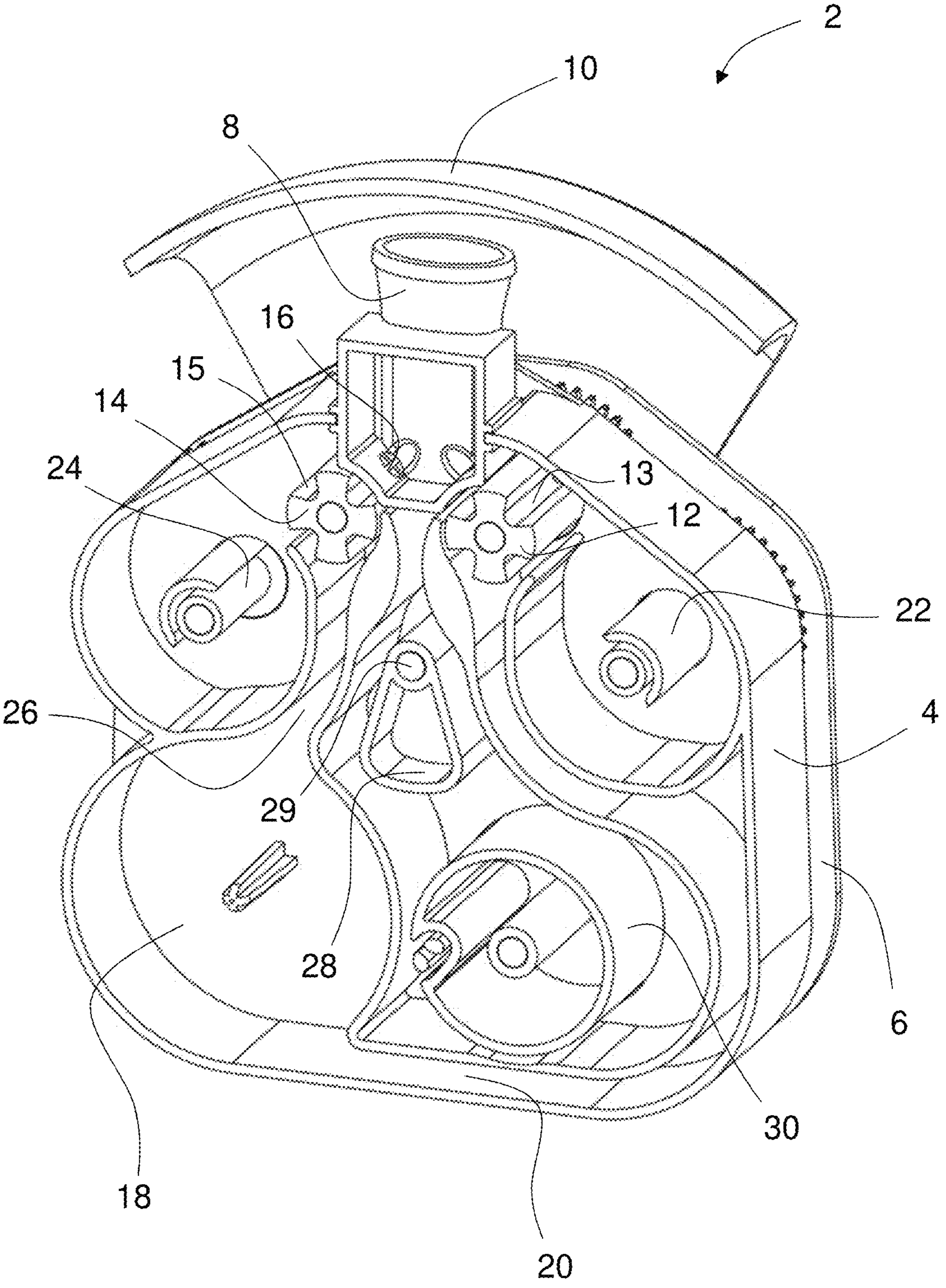
FIG. 1 is a perspective view of the interior of an inhaler device according to a first embodiment of the present invention.

FIG. 1 shows the interior of an inhaler device 2 according to a first embodiment of the invention. The inhaler device 2 is configured to use elongate blister strips of medicament comprising a base sheet/foil, defining individual blister pockets of medicament, and a lidding sheet in the form of a lidding foil which is peeled from the base foil to open the pockets and expose the medicament for inhalation.

A mid chassis 4 defines interior chambers and pathways of the device for receiving the and guiding the blister strips, and a rear chassis 6 provides mounting posts for various rotating components 12,14,22,24,30 within the device. An airway manifold 8, comprising a feature to allow interfacing with a mouthpiece, is received in an opening at the top of the mid chassis 4, and a moveable mouthpiece cover 10 (of which, for clarity, only the rear half is shown) is also provided.

First and second index wheels 12,14 each provide recesses 13,15 for receiving blister pockets of two separate blister strips and advancing them into place beneath openings 16 in the airway manifold 8 as the first and second index wheels 12,14 are rotated. The unopened blister strips are coiled and stored together in a storage chamber 18 defined by the mid chassis 4. From here, a first of the two blister strips is fed through a first passageway 20 in the mid chassis 4 and clockwise around the first index wheel 12, before the base foil is engaged with a first spool wheel 22. Similarly, the second blister strip is fed from the storage chamber 18 through a second passageway 26 and anticlockwise round the second index wheel 14, before its base foil is attached to a second spool wheel 24.

In use, the lidding foil from each of the first and second blister strips is separated from the base foil at the first and second index wheels 12,14 respectively. The first and second spool wheels 22,24 rotate with the first and second index wheels 12,14 to coil the used base foils. The two lidding foils pass either side of a tension balancer 28, which is mounted to the mid chassis 4 at a pivot 29, before being engaged with a common take-up drum 30. Rotation of the take-up drum 30 generates tension in the lidding foils when required to peel open the blisters in the first and second blister strips. Since both lidding foils are wound onto the same drum 30, a small imbalance in the tension of the first and second lidding foils can arise. However, a greater tension in the lidding foil running down either side of the tension balancer 28 will serve to bias the tension balancer 28 about the pivot 29 towards the other foil. This effectively shortens the path followed by the higher tension foil and lengthens the path followed by the lower tension foil until the tensions in the two lidding foils are balanced. Thus, maintenance of the tension in the lidding-foil within an acceptable range of tensions could be performed.

Figure 2:
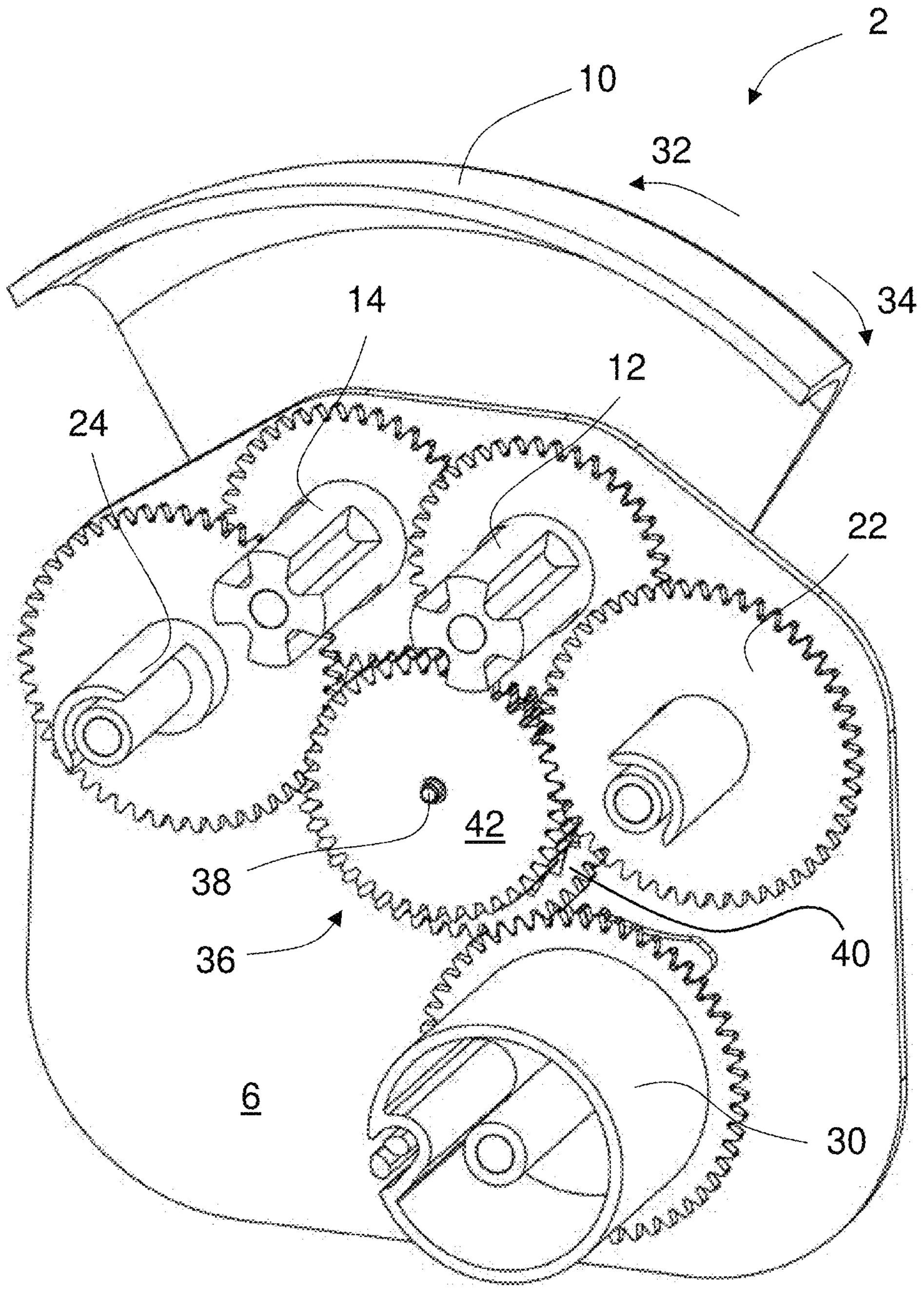
FIG. 2 shows a similar view to FIG. 1, but with a component removed.

FIG. 2 shows a similar view of the inhaler device interior with the mid chassis 4 and airway manifold 8 removed to expose the gearing between the various components of the inhaler device 2. In use, closing and opening the mouthpiece cover 10, as indicated by arrows 32 and 34, actuates a mechanism to drive the index wheels 12,14, the spool wheels 22,24 and the take-up drum 30 in a predefined sequence to index and peel doses for inhalation. The sequence is controlled by a central logic hub 36, which is mounted on a spindle 38 extending from the rear chassis 6 and is directly driven by movement of the mouthpiece cover 10.

The central logic hub 36 is mounted concentrically with three driving gears 40,42,44, which surround and are selectively engaged by the central logic hub 36. A take-up drum drive gear 40 can be seen engaging gearing on the base of the take-up drum 30, and a first index wheel drive gear 42 can be seen engaging gearing on the first index wheel 12 and first spool wheel 22. Although obscured in FIG. 2, a second index wheel drive gear 44 is also provided to engage gearing on the second index wheel 14 and second spool wheel 24.

Figure 3:
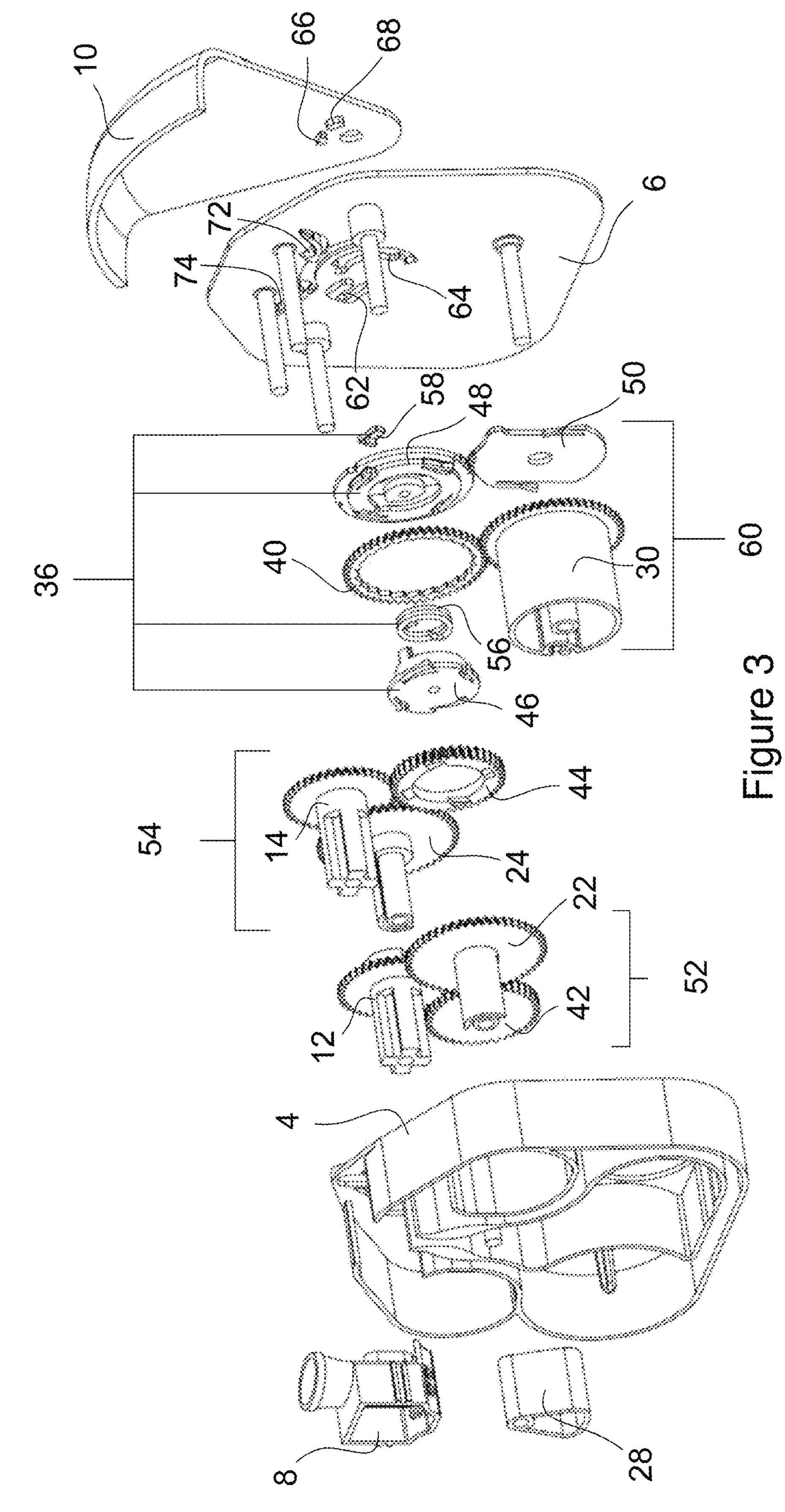
FIG. 3 shows an exploded view of the device of FIG. 1.

FIG. 3 is an exploded view of the inhaler device 2 of FIG. 1, in which the components making up the central logic hub 36 can be seen. The two main components of the central logic hub 36 are an index driving ratchet wheel 46, which engages with the first and second index wheel drive gears 42,44, and a peel driving ratchet wheel 48 which engages with the take-up drum drive gear 40 and with a take-up drum ratchet wheel 50 which, together with the take-up drum 30 and take-up drum drive gear 40, forms a take-up drum drive train 60. FIG. 3 also indicates the components making up a first index wheel drive train 52 and a second index wheel drive train 54, as will be described more fully later. A torsion spring 56 is arranged between the index driving ratchet wheel 46 and peel driving ratchet wheel 48 in the central logic hub 36, and a slider 58 is provided to selectively resist rotation of one or other of the index driving ratchet wheel 46 and peel driving ratchet wheel 48.

The rear chassis 6 also provides a channel 62 for receiving the slider 58, and a generally crescent shaped aperture 64. Inner and outer protrusions 66,68 formed on the mouthpiece cover 10 extend through the aperture 64. The aperture 64 also receives projections on the rear of the index driving ratchet wheel 46 and peel driving ratchet wheel 48 so that these components can be driven by rotational movement of the mouthpiece cover 10. More specifically, opening of the mouthpiece cover (clockwise movement from the position shown in FIG. 1) will result in the inner protrusion 66 engaging with and driving the index driving ratchet wheel 46 in a clockwise direction, while closing the mouthpiece cover 10 will engage the outer protrusion 68 with the peel driving ratchet wheel 48 to drive it in an anticlockwise direction.

The slider 58 allows one of the index driving ratchet wheel 46 and peel driving ratchet wheel 48 to be 'locked' while rotation of the mouthpiece cover 10 rotates the other. This builds a biasing force in the torsion spring 56, which can then be released by moving the slider 58 to release the previously locked component.

The rear chassis 6 also provides first and second ratchet pawls 72,74 to selectively lock the first and second index wheels 12,14 respectively.

Figure 4:
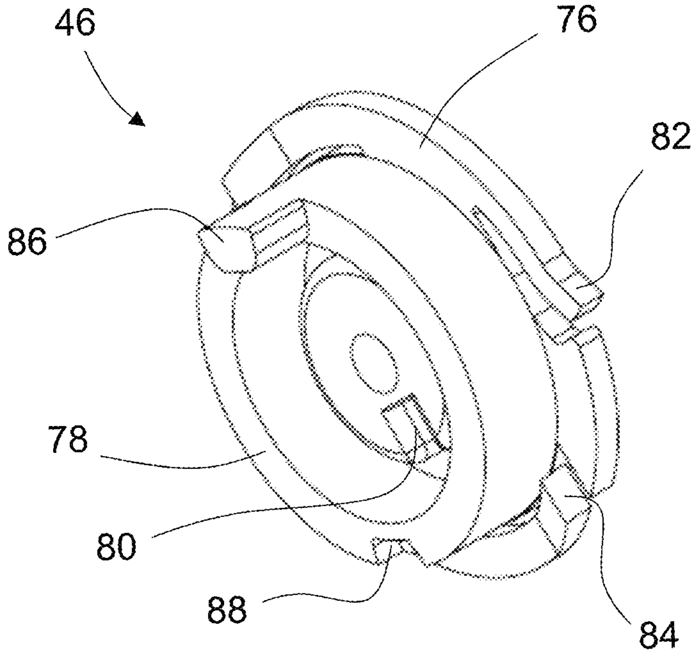
FIG. 4 shows a first component from a central hub of the inhaler device.

The rear of the index driving ratchet wheel 46 from the central logic hub 36 is shown in FIG. 4. The wheel 46 comprises a generally circular plate 76 with a ring-shaped boss 78 extending from the rear face. A recess 80 is provided in the rear face of the plate 76 within the flange 78 for receiving an arm of the torsion spring 56. Around the periphery of the plate 76 are provided two circumferential ratchet pawls 82 and two axial ratchet pawls 84. The circumferential ratchet pawls 82 and axial ratchet pawls 84 are oriented so that they apply a driving force in opposite rotational directions. FIG. 4 also shows a projection 86 extending from the end of the boss 78, and a recess 88 in its outer periphery. The projection 86 is for engagement with the inner protrusion 66 of the mouthpiece cover, and the recess 88 receives the slider 58 to lock the index driving ratchet wheel 46 against rotation.

Figure 5:
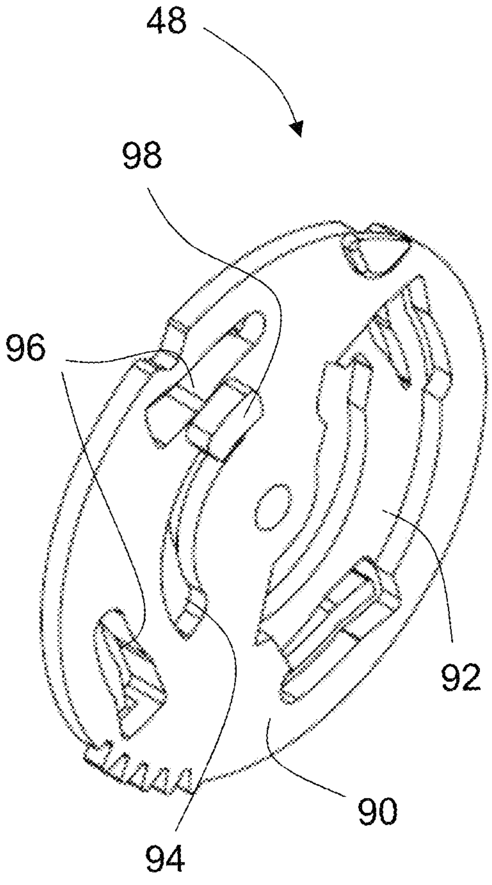
FIGS. 5 and 6 show a second component from a central hub of the inhaler device.
Figure 6:
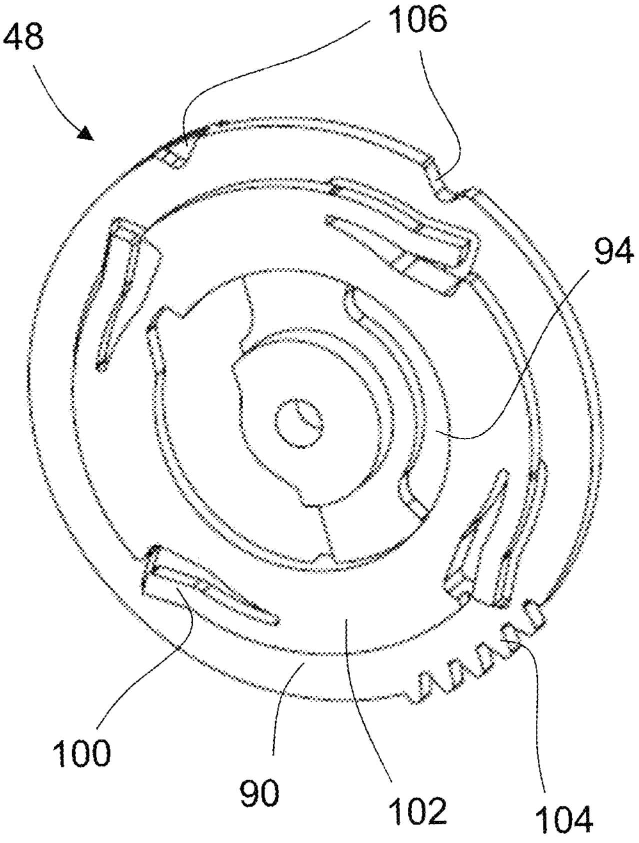

FIGS. 5 and 6 show the peel driving ratchet wheel 48 in greater detail. A rear view is provided in FIG. 5, showing a generally circular plate 90 with a large cut-out section 92 to one side, and a generally crescent-shaped slot 94 and two smaller cut-out sections 96 on the other. A projection 98 extends from the rear surface of the plate, adjacent the edge of the slot 94, for engagement with the outer protrusion 68 formed on the mouthpiece cover 10. A front view of the peel driving ratchet wheel 48 is shown in FIG. 6. Four radial ratchet pawls 100 are provided around the outer periphery of a ring-shaped boss 102 that extends from the front of the plate 90. So that the plate 90 does not prevent movement of the ratchet pawls 100, two are located in the region of the wheel 48 where the large cut-out section 92 is provided, and the other two correspond with the locations of the smaller cut-out sections 96. A small toothed section 104 is provided on the outer periphery of the plate 90, along with a pair of notches 106.

The inner diameter of the ring-shaped boss 102 is large enough to receive the boss 78 of the index driving ratchet wheel 46 when the central logic hub 36 is assembled. When assembled, the projection 86 extending from the end of the boss 78 on the index driving ratchet wheel 46 passes through the slot 94 to extend from the rear surface of the plate 90 of the peel driving ratchet wheel 48 to the same extent as the projection 98 formed directly on the plate 90 of the peel driving ratchet wheel 48.

Figure 7:
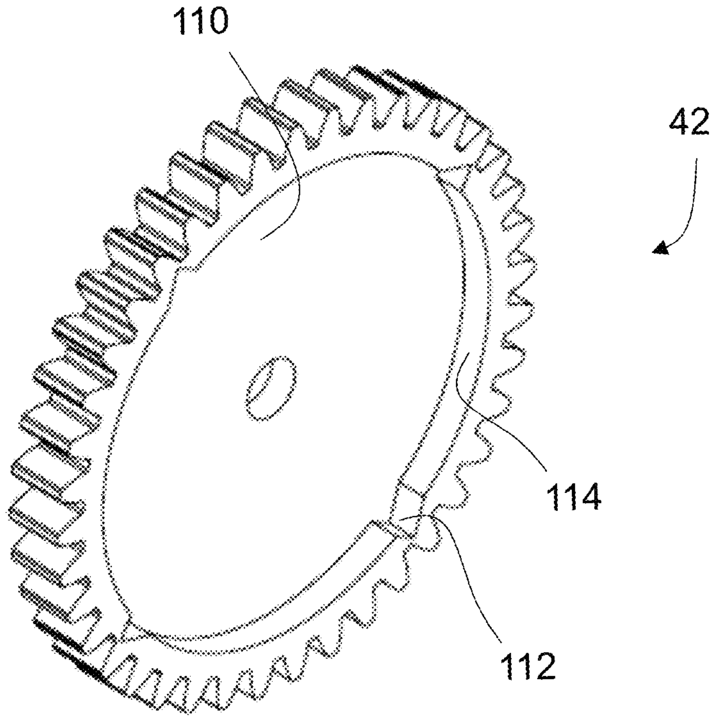
FIG. 7 shows a gear component for linking the central hub to a first drive train assembly of the inhaler device.

FIG. 7 shows the rear surface of the first index wheel drive gear 42. An internal cavity 110 is shown in a rear surface of the drive gear 42, with four radially extending notches 112 provided around the inner peripheral wall 114 of the cavity 110. The diameter of the cavity 110 is sufficient to receive the generally circular plate 76 of the index driving ratchet wheel 46 shown in FIG. 4, with the circumferential ratchet pawls 82 being received in two of the four notches 112.

Figure 8:
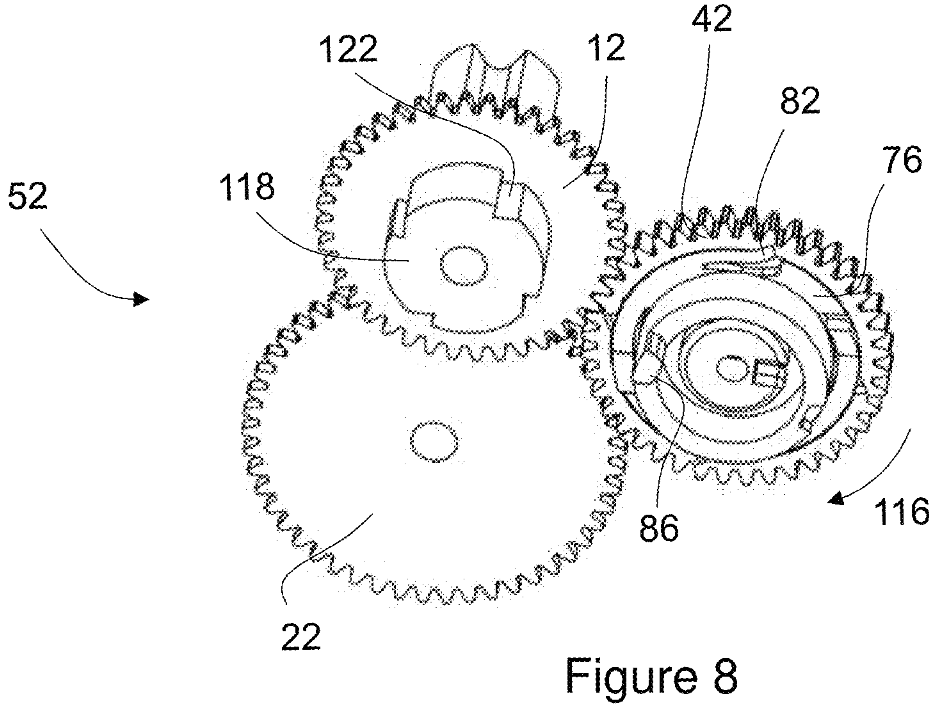
FIG. 8 shows the first drive train assembly.

The assembly is shown, with the rest of the first index wheel drive train 52, in FIG. 8. The engagement of the circumferential ratchet pawls 82 in the notches 112 transmits drive from the index driving ratchet wheel 46 to the first index wheel drive gear 42 only in an anticlockwise direction 116 (FIG. 8 being a rear view of the assembly). During clockwise movement of the index driving ratchet wheel 46, as generated during mouthpiece opening by engagement of projection 86 with the inner protrusion 66 of the mouthpiece cover, the circumferential ratchet pawls 82 are able to flex out of the notches 112 permitting relative rotation between the index driving ratchet wheel 46 and the first index wheel drive gear 42. A boss 118 provided on a rear surface of the first index wheel 12 provides notches 122 for engagement with the first ratchet pawl 72 on the rear chassis 6 to resist rotation of the first index wheel 12 in the corresponding direction. Accordingly, the first index wheel drive train 52 provides drive to the first index wheel 12 and first spool wheel 22 only during mouthpiece cover closing.

Figure 9:
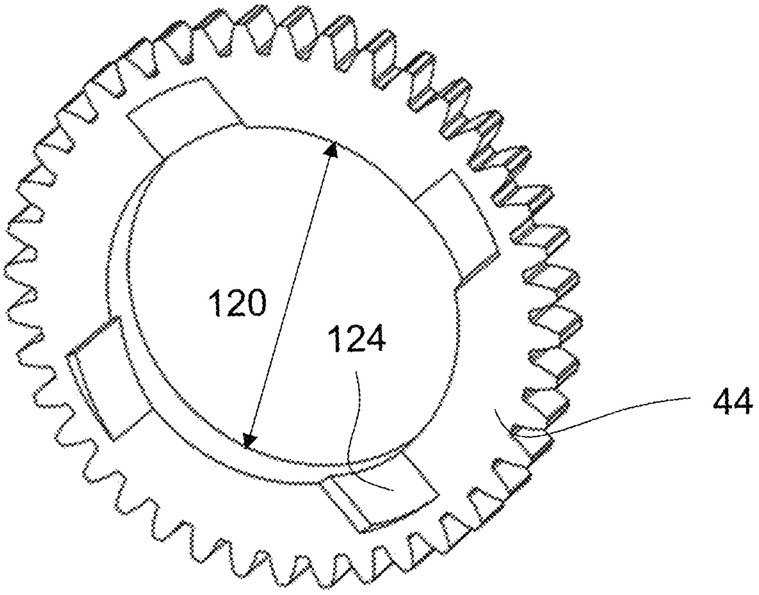
FIG. 9 shows a gear component for linking the central hub to a second drive train assembly of the inhaler device.

FIG. 9 shows the ring-shaped second index wheel drive gear 44 in greater detail. Four sloping recesses or notches 124 are provided in a front face of the drive gear 44 for engagement with the axial ratchet pawls 84 provided on the index driving ratchet wheel 46 when the boss 78 of the index driving ratchet wheel 46 is received within the ring. The inner diameter 120 of the index wheel drive gear 44 is the same as the inner diameter of the ring-shaped boss 102 of the peel driving ratchet wheel 48 to receive the boss 78 of the index driving ratchet wheel 46.

Figure 10:
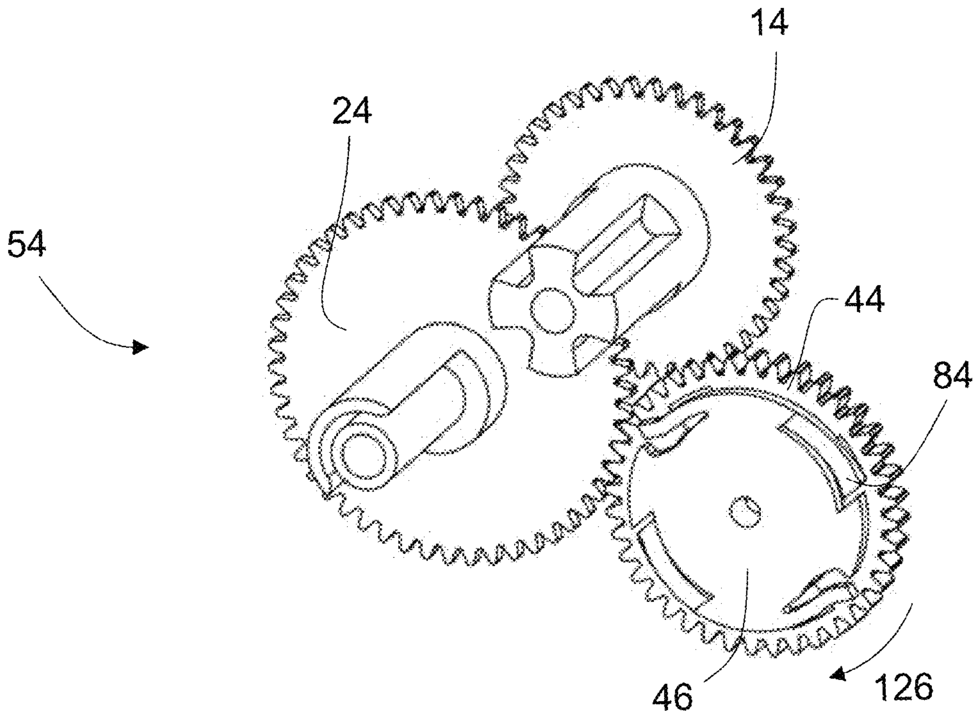
FIG. 10 shows the second drive train assembly.

FIG. 10 shows a front view of the second index wheel drive train 54 incorporating the assembly of the second index wheel drive gear 44 and index driving ratchet wheel 46 as described above. The axial ratchet pawls 84 are shown engaged with two of the notches 124 so that clockwise drive 126 from the index driving ratchet wheel 46 is transmitted to the second index wheel drive gear 44. As discussed above, the index driving ratchet wheel 46 is driven clockwise 126 by engagement of projection 86 on the rear surface of the index driving ratchet wheel 46 with the inner protrusion 66 of the mouthpiece cover during opening the mouthpiece cover 10. Therefore, the second index wheel 14 and second spool wheel 24 are both driven when the mouthpiece 10 is opened. In contrast, anticlockwise rotation of the index driving ratchet wheel 46 results in the axial ratchet pawls 84 flexing out of the notches 124 permitting relative rotation between the index driving ratchet wheel 46 and the second index wheel drive gear 44.

Figure 11:
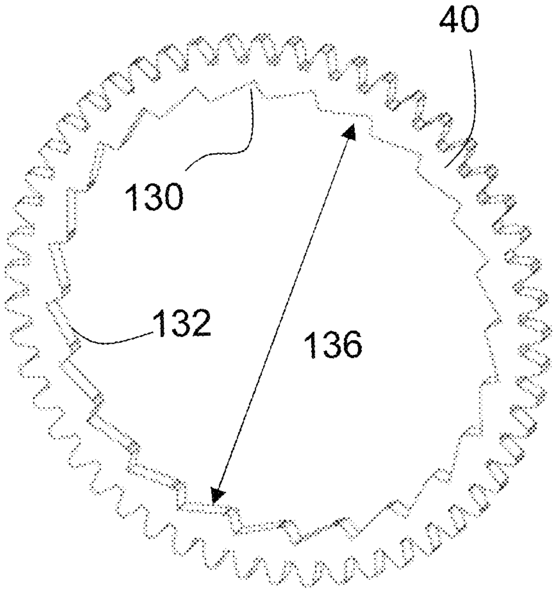
FIG. 11 shows a gear component for linking the central hub to a third drive train assembly of the inhaler device.

FIG. 11 shows the ring-shaped take-up drum drive gear 40 in greater detail. A number of notches 130 are provided in an inner peripheral wall 132 of the drive gear 40 to serve as ratchet teeth. The opening defined by the inner peripheral wall 132 has a diameter 136 sized to receive the boss 102 of the peel driving ratchet wheel 48.

Figure 12:
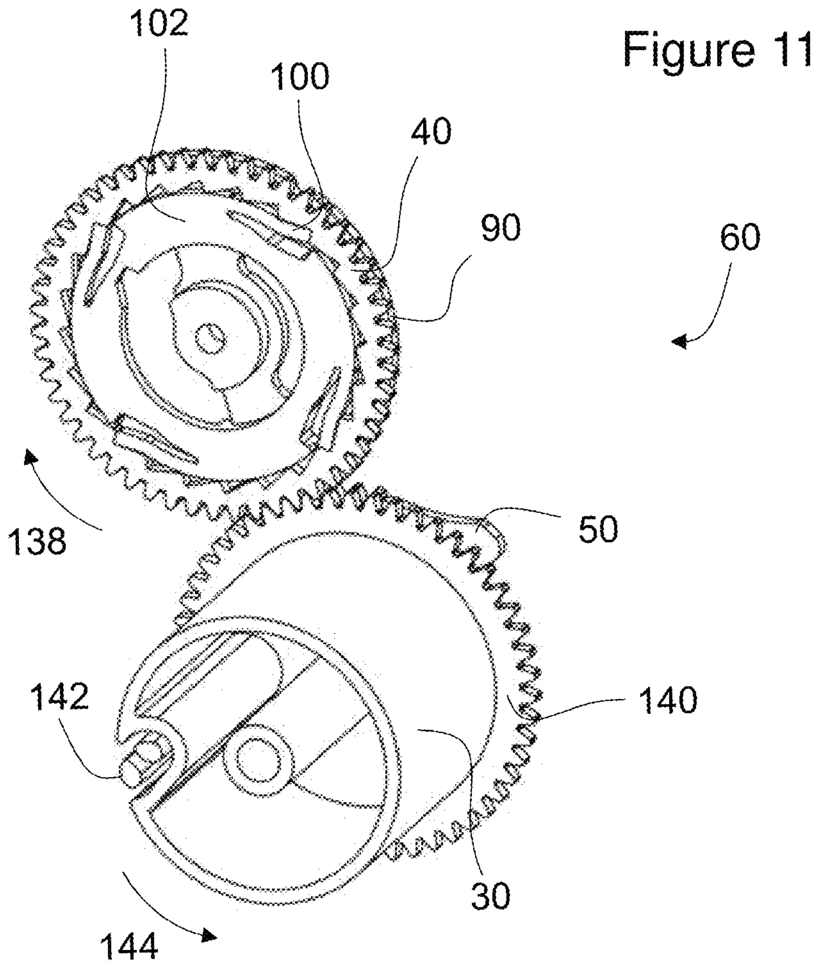
FIG. 12 shows a front view the third drive train assembly.

A front view of the take-up drum drive train 60 is shown in FIG. 12. The boss 102 of the peel driving ratchet wheel 48 has been inserted into the take-up drum drive gear 40 from behind such that the radial ratchet pawls 100 of the peel driving ratchet wheel 48 are engaged with the notches 130 to transmit clockwise rotation 138 of the peel driving ratchet wheel 48 to the take-up drum drive gear 40. The take-up drum drive gear 40 engages with gear teeth 140 provided around a base of the take-up drum 30 to transmit rotation to the take-up drum 30. A pair of retaining features 142 on one side of the take-up drum 30 retains the free ends of a pair of lidding foils such that, in use, anticlockwise rotation 144 of the take-up drum 30 applies tension to the lidding foils and winds them around the body of the take take-up drum 30.

The plate 90 of the peel driving ratchet wheel 48 bears against a rear surface of the take-up drum drive gear 40, and its generally circular profile can be seen between the gear teeth of the take-up drum drive gear 40. Part of the take-up drum ratchet wheel 50 is also visible in the front view of FIG. 12, behind the take-up drum 30.

Figure 13:
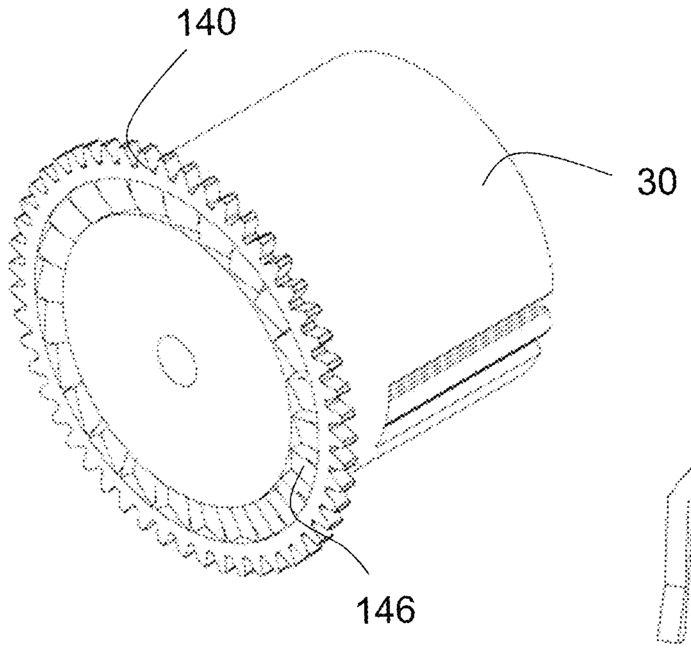
FIGS. 13 and 14 show components of the third drive train assembly
Figure 14:
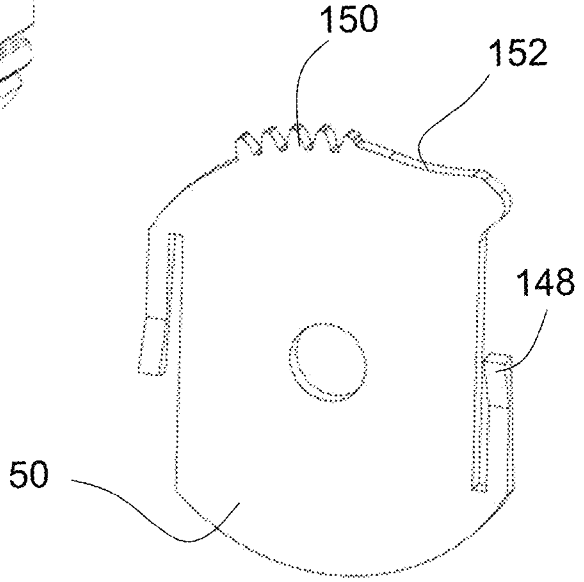

FIG. 13 shows a rear view of the take-up drum 30. The gear teeth 140 around the base of the take-up drum 30 are clearly visible, along with a ring of ratchet teeth 146 provided on the rear surface. The ratchet teeth 146 engage, in use, with a pair of ratchet pawls 148 provided on the opposite sides of the take-up drum ratchet wheel 50, extending from its front face which is shown in FIG. 14. Gear teeth 150 are provided on a section of the outer edge of the take-up drum ratchet wheel 50, adjacent an inwardly curved section 152.

Figure 15:
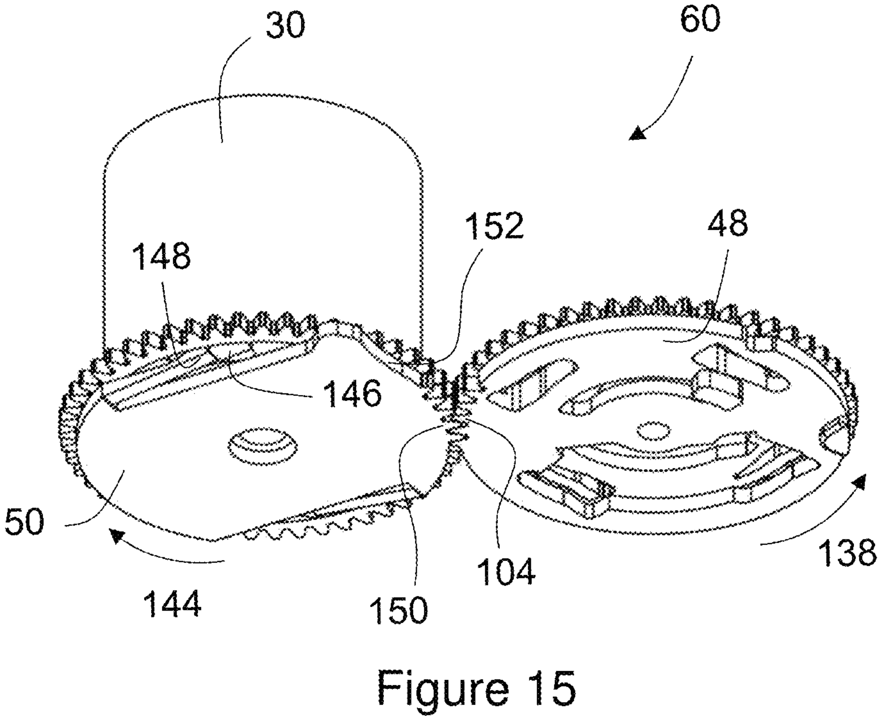
FIG. 15 shows a rear view the third drive train assembly.

A rear view of the take-up drum drive train 60 is shown in FIG. 15. The rear view shows the engagement of the ratchet pawls 148 and gear teeth 150 on the take-up drum ratchet wheel 50 with, respectively, the ratchet teeth 146 on the take-up drum 30 and the toothed section 104 on the peel driving ratchet wheel 48. It will be understood that clockwise rotation 138 of the peel driving ratchet wheel 48 will be transferred to the take-up drum ratchet wheel 50 while the gear teeth 150 remain engaged with the toothed section 104, and that the resulting anticlockwise rotation 144 will be transmitted to the take-up drum 30 via the ratchet pawls 148 and ratchet teeth 146. When the gear teeth 150 reach the end of the toothed section 104, the inwardly curved section 152 of the take-up drum ratchet wheel 50 will receive the curved outer edge of the peel driving ratchet wheel 48, providing a Geneva style lock to hold the take-up drum ratchet wheel 50 against further rotation. The ratchet pawls 148 are able to flex past the ratchet teeth 146 to allow further anticlockwise rotation 144 of the take-up drum 30 driven by the peel driving ratchet wheel 48 and take-up drum drive gear 40 as previously described, but engage with the ratchet teeth 146 to resist any clockwise rotation of the take-up drum 30 while the take-up drum ratchet wheel 50 is static.

Figure 16:
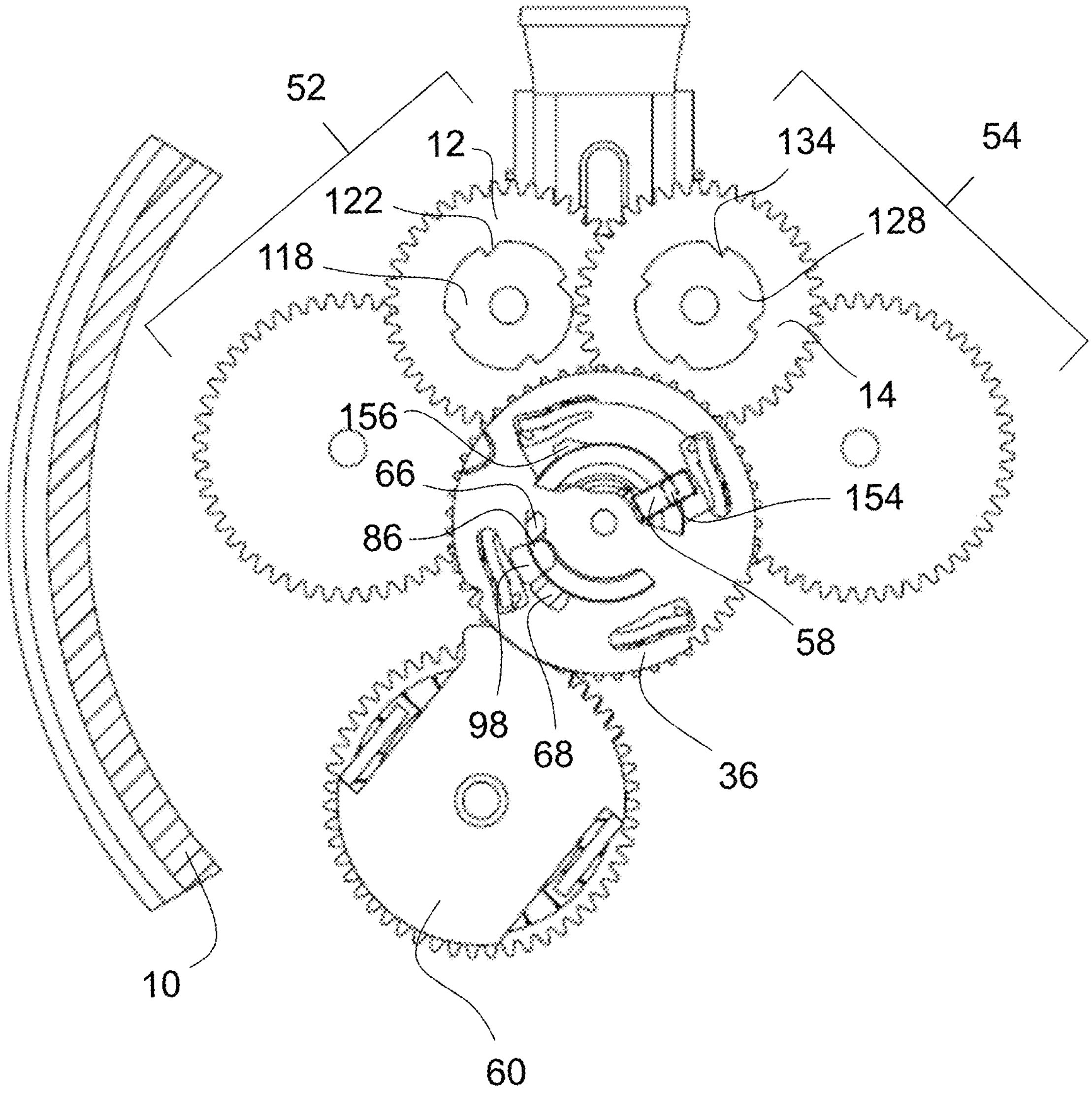
FIG. 16 shows a rear view of the overall mechanism of the inhaler device of FIG. 1.

FIG. 16 shows a rear view of the entire mechanism of the inhaler device 2, including the central logic hub 36, take-up drum drive train 60 and first and second index wheel drive trains 52,54. The rear view also shows notches 134 on a boss 128 on the rear surface of the second index wheel 14, similar to the boss 118 and notches 122 provided on the rear surface of the first index wheel 12. The notches 134 on the second index wheel 14 are designed to engage with the second ratchet pawl 74 provided on the rear chassis 6 in the same way as the notches 122 on the first index wheel 12 engage with the first ratchet pawl 72. However, rotation is resisted in the opposite direction.

The mouthpiece cover 10 is also shown in cross section, including the inner and outer protrusions 66,68 formed thereon. The inner protrusion 66 is shown abutting the projection 86 of the index driving ratchet wheel 46 that extends through the a generally crescent-shaped slot 94 in the peel driving ratchet wheel 48. The outer protrusion 68 is shown abutting the projection 98 on the peel driving ratchet wheel 48. The slider 58 is also shown, with a tab 154 provided on the obscured front face of the slider 58 illustrated in broken lines. The tab 154 engages with either the recess 88 (not shown) in the index driving ratchet wheel 46 or with a similar recess 156 provided in the peel driving ratchet wheel 48 to selectively lock one or other component against rotation.

As illustrated in FIG. 16, the mouthpiece cover 10 is fully open, and a dose has just been inhaled from the inhaler device 2. The operation of the device 2 from this position will be explained in the following figures.

Figure 17:
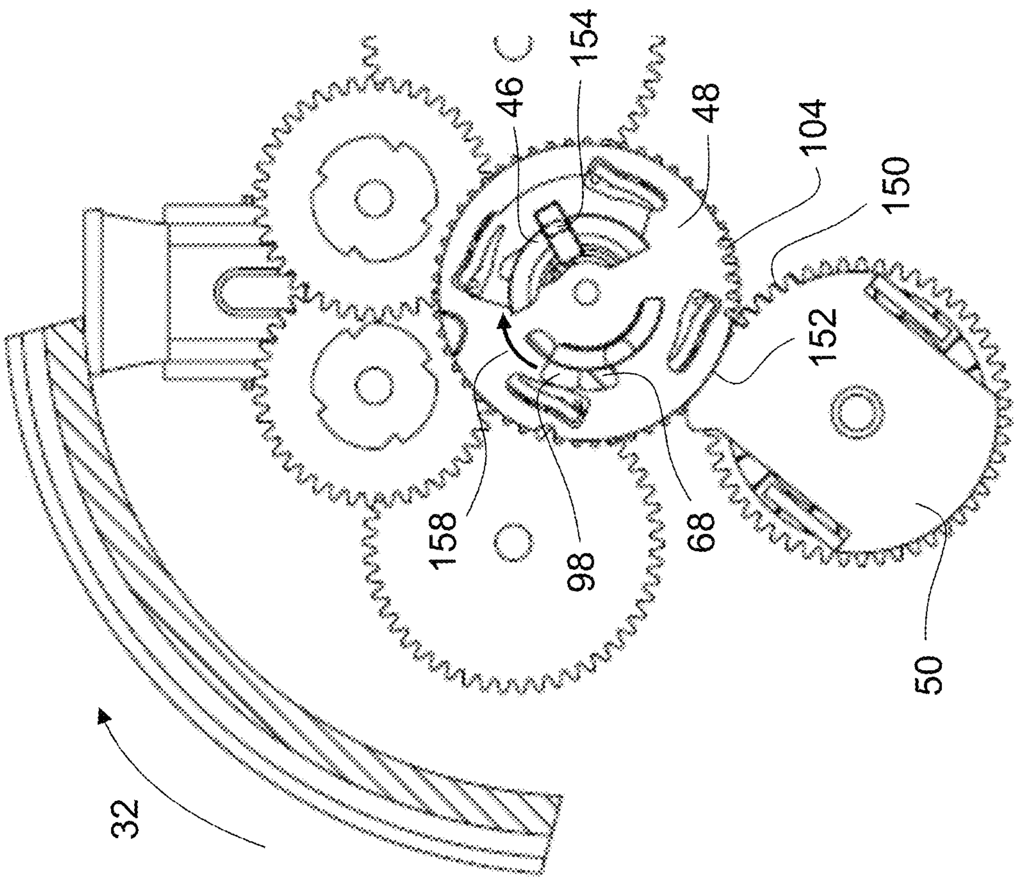

FIG. 17 shows the initial stage of mouthpiece cover closing. The mouthpiece 10 has been rotated by around 45° in the direction of arrow 32. The engagement of the outer protrusion 68 with the projection 98 on the peel driving ratchet wheel 48 directly drives the peel driving ratchet wheel 48 to rotate in the same direction 158, anticlockwise as the inhaler device 2 is viewed from the front, as the mouthpiece cover 10. None of the other components is rotated from the position shown in FIG. 16. The ratchet pawls 100 allow anticlockwise rotation of the peel driving ratchet wheel 48 within the take-up drum drive gear 40. The curved outer edge of the peel driving ratchet wheel 48 runs past the inwardly curved section 152 of the take-up drum ratchet wheel 50 until just after the point shown in FIG. 17, when the gear teeth 150 on the take-up drum ratchet wheel 50 are close to engagement with the toothed section 104 of the peel driving ratchet wheel 48. The tab 154 of the slider 58 is engaged with the recess 88 of the index driving ratchet wheel 46 to prevent its rotation, so that no indexing of either index wheel 12,14 takes place. The torsion spring 56 is charged by relative rotation between the peel driving ratchet wheel 48 and the index driving ratchet wheel 46.

Figure 18:
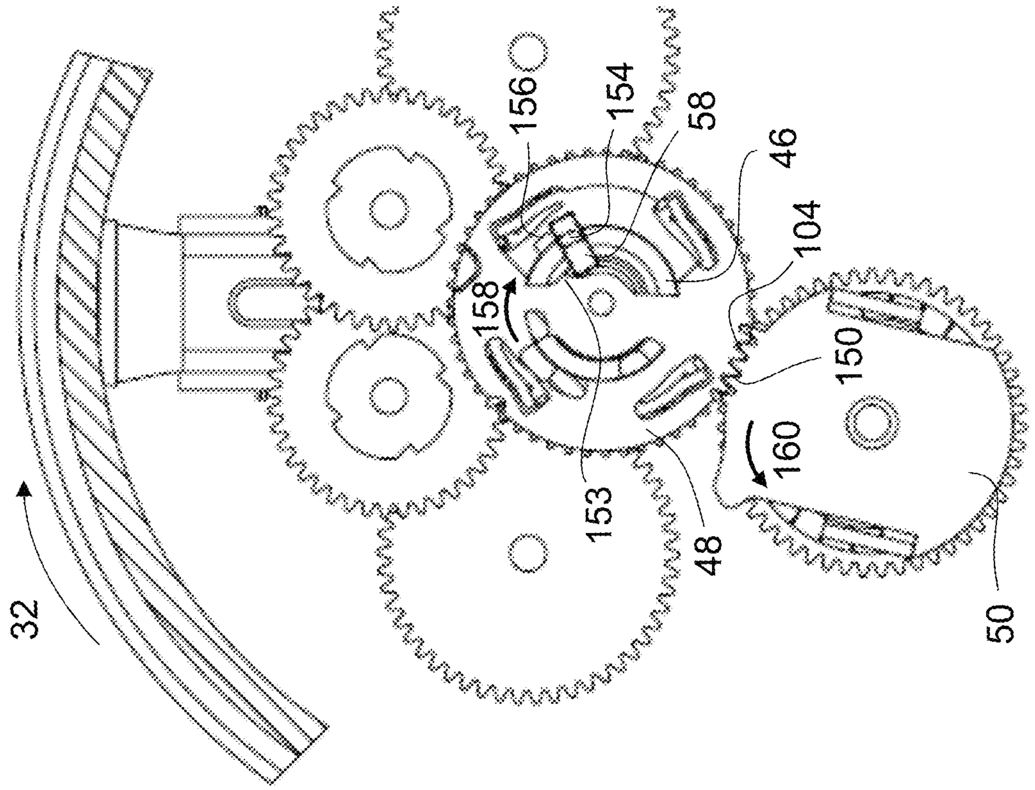
FIGS. 17 to 22 show the operation of the mechanism shown in FIG. 16.

The next stage in operation is shown in FIG. 18. Continued closing 32 of the mouthpiece cover 10 causes further anticlockwise rotation 158 of the peel driving ratchet wheel 48, engaging the toothed section 104 with the gear teeth 150 on the take-up drum ratchet wheel 50. This results in clockwise rotation 160 (when viewed from the front) of the take-up drum ratchet wheel 50, and the associated take-up drum 30, which reduces the tension in both lidding foils as the mouthpiece cover 10 is closed. The tab 154 is still preventing rotation of the index driving ratchet wheel 46, but is now adjacent an edge of the recess 156 provided in the peel driving ratchet wheel 48. A radial protrusion 153 on the peel driving ratchet wheel 48 is also adjacent the radially inner end of the slider 58.

Figure 19:
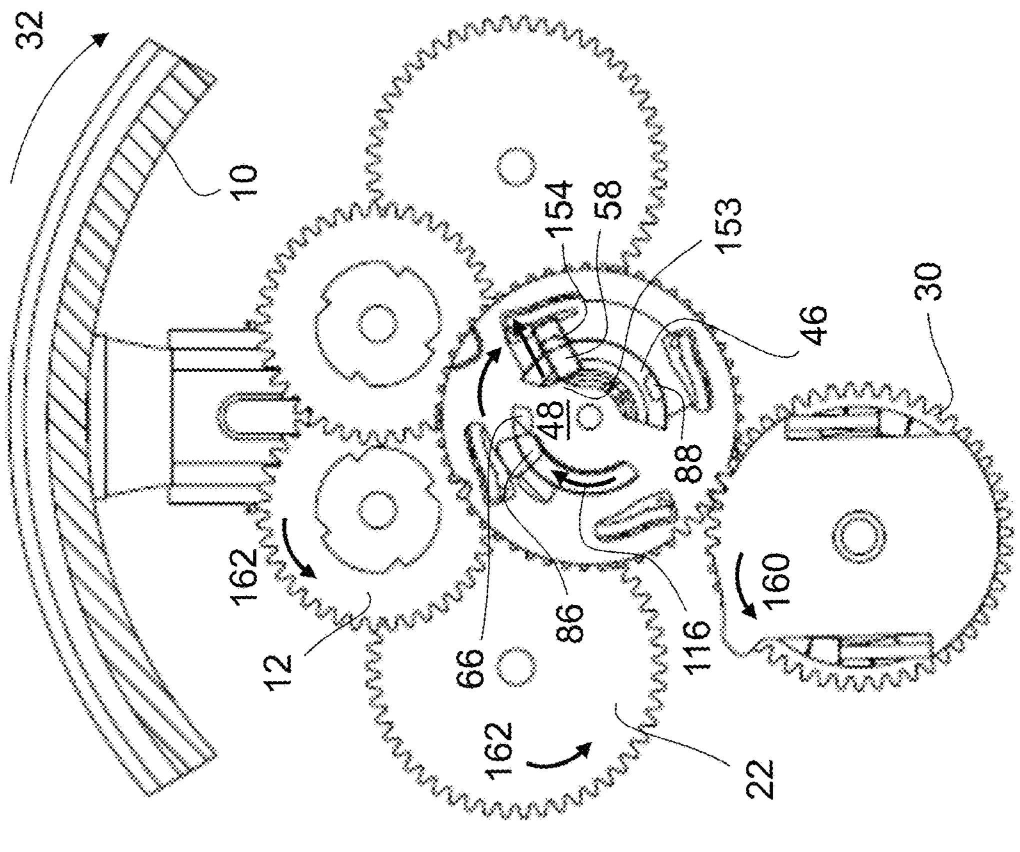

FIG. 19 shows that mouthpiece cover 10 in the fully closed position. The continued movement 32 of the mouthpiece cover 10 has further rotated the take-up drum 30 clockwise 160 to further reduce the tension on the lidding foils, and provide slack in the lidding foils between the take-up drum 30 and the first and second index wheels 12,14.

The peel driving ratchet wheel 48 has also been further rotated, past a commitment point where the radial protrusion 153 and angled surfaces provided on the recess 88 of the index driving ratchet wheel 46 and the recess 156 provided in the peel driving ratchet wheel 48 guide/urge the slider 58 radially outwards to move the tab 154 from the recess 88 into the recess 156. The now freed index driving ratchet wheel 46 has been driven by the torsion spring to 'catch up' with the peel driving ratchet wheel 48 by rotating in an anticlockwise direction until the projection 86 of the index driving ratchet wheel 46 abuts the inner protrusion 66 of the mouthpiece cover 10. As described in relation to FIG. 8 above, this anticlockwise rotation 116 of the index driving ratchet wheel 46 is transmitted through the first index wheel drive train 52 to advance or index the first index wheel 12, in a clockwise direction 162, by one recess 13 or one dose, and to similarly drive the first spool wheel 22 to take up the base foil. The pair of notches 106 in the peel driving ratchet wheel 48 are located to align with the ratchet pawls 72,74 on the rear chassis 6, allowing the ratchet pawls 72,74 to deflect so that the first ratchet pawl 72 does not inhibit rotation of the first index wheel.

The indexing operation also applies tension to the first used lidding foil, but this only serves to take up the slack created by the clockwise rotation 160 of the take-up drum 30. As a result, the lidding foil is not peeled from the blister strip, but is instead doubled back over the unopened blister strip in a space provided between the first index wheel 12 and openings 16 in the airway manifold 8. This is shown in greater detail in FIG. 23A.

Figure 20:
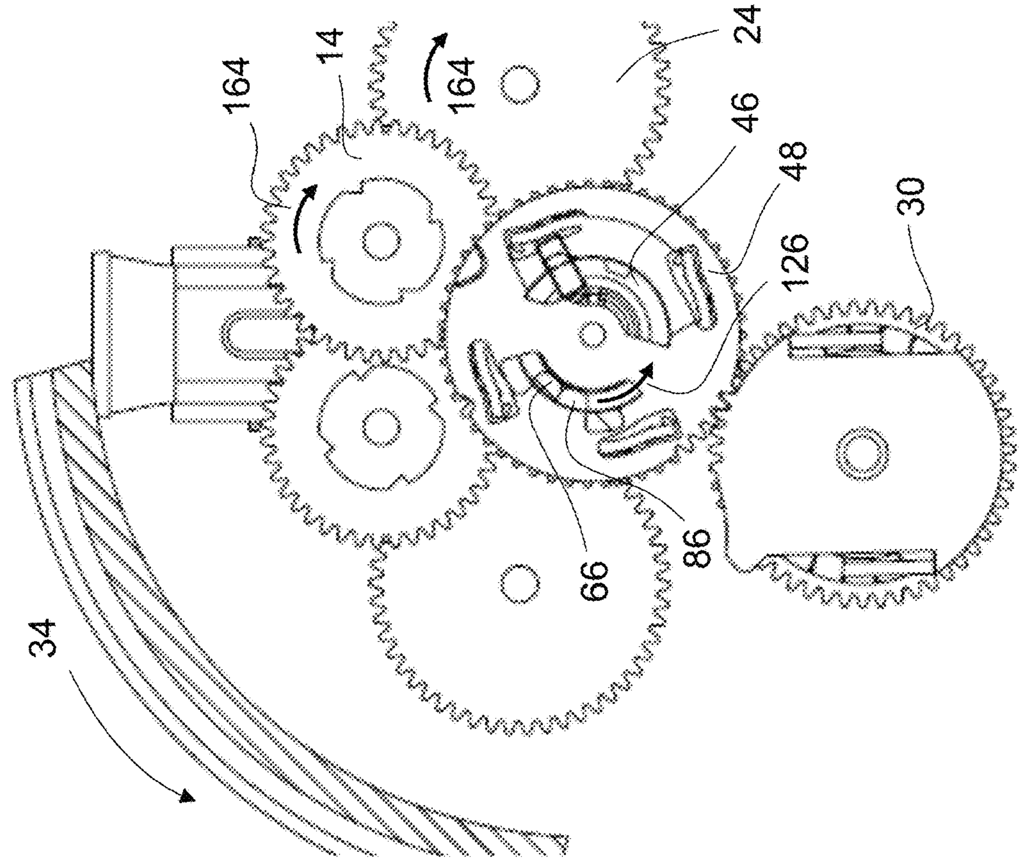

FIG. 20 shows the initial stage of opening the mouthpiece cover 10. The opening movement 34 of the mouthpiece cover 10 causes clockwise rotation 126 of the index driving ratchet wheel 46 through engagement of the inner protrusion 66 of the mouthpiece cover 10 with the projection 86 of the index driving ratchet wheel 46. This clockwise rotation 126 drives the second index wheel 14 and second spool wheel 24 as described in FIGS. 9 and 10 above, so that both rotate in an anticlockwise direction 164 to start advancing/indexing the second blister strip. The peel driving ratchet wheel 48 remains locked against rotation, so that no drive is provided to the take-up drum 30 and so that the notches 106 continue to allow movement of the ratchet pawls 72,74 so that the second ratchet pawl 74 does not impede anticlockwise rotation 164 of the second index wheel 14.

Figure 21:
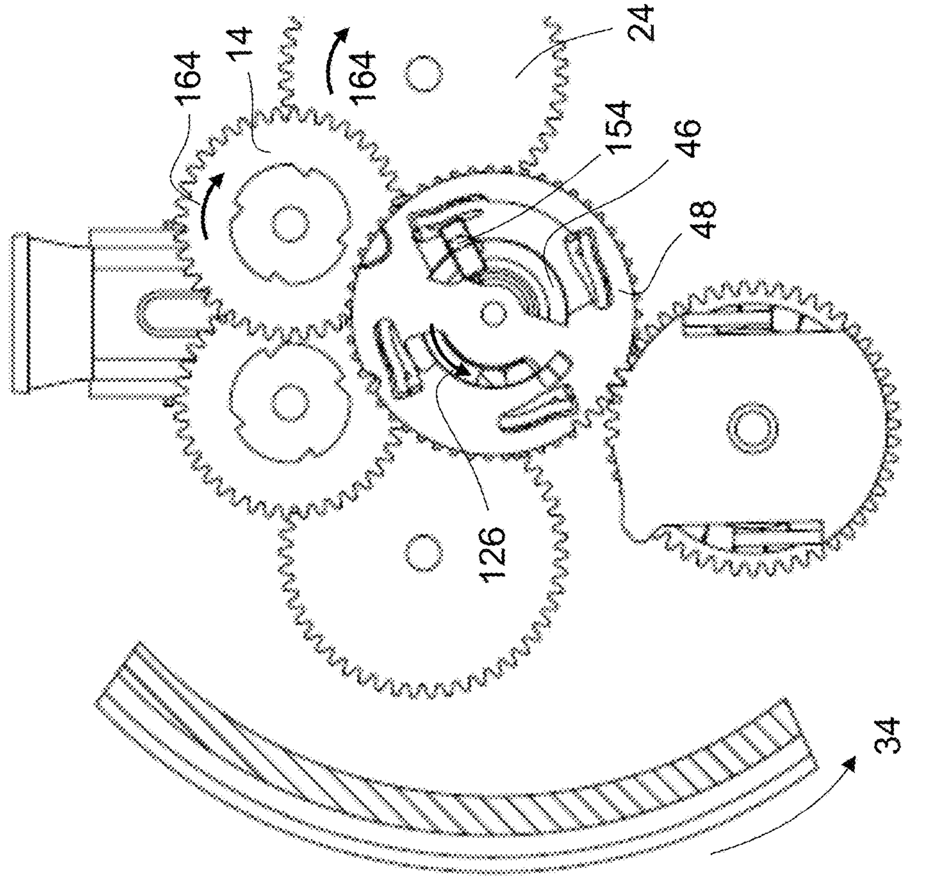

FIG. 21 illustrates further opening 34 of the mouthpiece cover, and the resulting further clockwise rotation 126 of the index driving ratchet wheel 46 and resulting anticlockwise rotation 164 of the second index wheel 14 and second spool wheel 24. The second index wheel 14 has now been advanced or indexed by one recess 15, or one dose, from the position shown in FIG. 19. As before, the slack created in the lidding foils during mouthpiece closure avoids peeling of the lidding foil a from the second blister strip during indexing. The tab 154 is adjacent the recess 88 in the index driving ratchet wheel 46 in FIG. 21, so that any further movement will urge the tab 154 from the into the recess 156 in the peel driving ratchet wheel 48 into the recess 88 in the index driving ratchet wheel 46.

Figure 22:
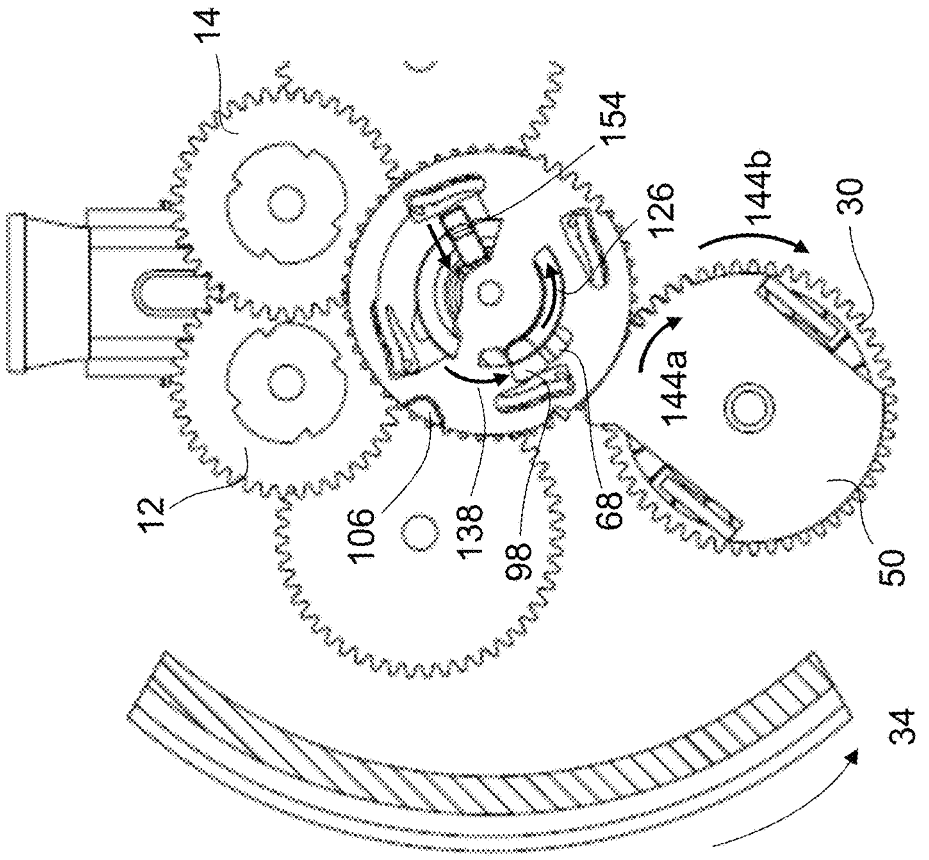

In FIG. 22, the mouthpiece cover has been moved 34 to its fully open position, through/past a further commitment point. The final clockwise rotation 126 of the index driving ratchet wheel 46 allows the tab 154 to move radially inwards from the recess 156 in the peel driving ratchet wheel 48 into the recess 88 in the index driving ratchet wheel 46. This frees the peel driving ratchet wheel 48 to rotate clockwise 138 under the drive of the torsion spring 56, and the rotation is transferred to both the take-up drum ratchet wheel 50 and the take-up drum 30.

The sudden rotation **144*b* of the take-up drum applies tension to both lidding foils simultaneously, to expose the next dose in each blister strip for inhalation. As described in relation to FIGS. 12 to 15 above, the anticlockwise rotation 144*b* of the take-up drum 30 will be greater than the anticlockwise rotation 144*a* of the take-up drum ratchet wheel 50. This allows the take-up drum 30 to release tension in the lidding foils on mouthpiece closure after a dose is dispensed, while still effectively peeling the lidding foils from the next dose on mouthpiece opening. The sudden rotation of the peel driving ratchet wheel 48 also moves the notches 106 out of alignment with the ratchet pawls 72,74 on the rear chassis 6, effectively locking the first and second index wheels 12,14** against rotation.

Once a user has inhaled the exposed dose, the inhaler is back in the configuration shown and described in FIG. 16.

Figure 23A:
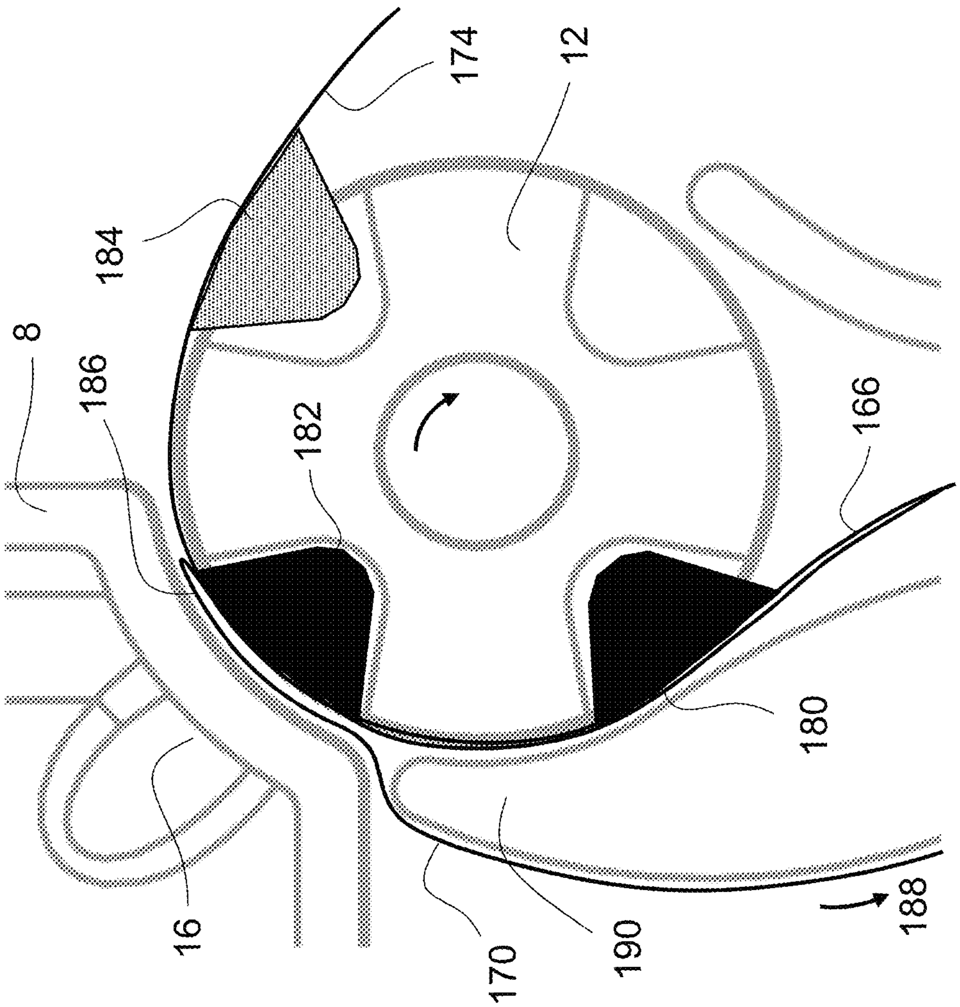
FIG. 23A shows a detail view of the area marked 'A' in FIG. 23.
Figure 23:
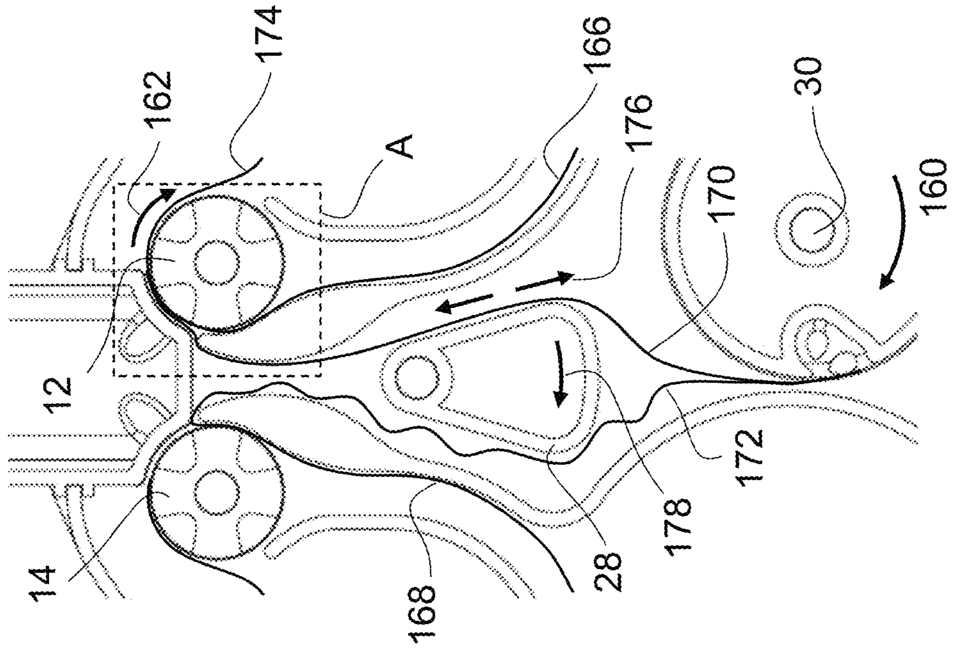
FIG. 23 shows a front view of the mechanism, illustrating the paths of the blister strip, lidding foil and base foil.

FIG. 23 schematically shows a front view of part of the inhaler mechanism, illustrating the paths of first and second blister strips 166,168 through the inhaler device 2. The mouthpiece cover 10 of the inhaler is fully closed, as described in relation to FIG. 19, so the take-up drum 30 has been rotated clockwise 160 to actively release tension in the separated first and second lidding foils 170,172. However, the clockwise rotation 162 of the first index wheel 12 has advanced the base foil 174 of the first blister strip 166, dragging the first lidding foil 170 around the first index wheel. The clockwise rotation 160 of the take-up drum 30, as previously described, creates slack equivalent to one index distance in each lidding foil 170,172, so there is little or no tension in the first lidding foil 170 as a result of advancing/indexing the first index wheel 12.

The second index wheel 14 has not been rotated at this stage, so the second lidding foil 172 remains slack. As such, any excess tension 176 that may be generated in the first lidding foil 170 by sudden movement of the first index wheel 12 can be accommodated by movement 178 of the tension balancer 28 towards the second lidding foil 172. The tension balancer 28 can thus acts as a further means to release or manage tension so that minimal tension is maintained in both lidding foils 170,172 with the mouthpiece cover 10 closed, even though the first index wheel 12 has already been advanced/indexed in this position.

FIG. 23A shows an enlarged view of the are marked 'A' in FIG. 23. The first blister strip 166 is shown passing around the first index wheel 12, with first and second full blister pockets 180,182 and an empty blister pocket 184 illustrated. The second full blister pocket 182 has been advanced to a position under an opening 16 in the airway manifold 8. The first lidding foil 174 has been doubled back 186 over the second full blister pocket 182, in a space between the first index wheel 12 and the airway manifold 8. When tension 188 is applied to the lidding foils 170,172 by anticlockwise rotation **144*b* of the take-up drum 30, the first lidding foil 170 will be pulled around a static peel-beak or end-stop 190 provided on the mid chassis 4 and peeled from the second full blister pocket 182**.

It will be understood, from the foregoing description, that the operation of the mechanism of the inhaler device 2 comprises several separate actions that arise from a single actuation of the mechanism (movement of the mouthpiece cover 10), and that these actions encompass a number of commitment-points. Potential problems that may arise if some commitment points are passed while others remaining unreached during include, for example:

- over-charging and under-charging springs;
- forcing the device out of sync;
- failing to peel blisters or adequately present the formulation for inhalation;
- incorrect dose-counting; or
- over-stressing of components leading to failure.

It is therefore beneficial for such actions to be tied or linked together, so that they are no longer separable and have to occur with sufficient synchronisation to avoid these issues.

This inhaler device 2 described above uses a 'catch-up' mechanism. As the mouthpiece cover 10 is opened it drives the index driving ratchet wheel 46, which rotates by the opening-angle before releasing the slider 58. The slider 58 releases the peel driving ratchet wheel 48 to rotate until peeling is complete. During closure of the mouthpiece cover 10, the peel driving ratchet wheel 48 is driven back until it resets the slider 58. This in turn releases the index driving ratchet wheel 46 to rotate back until the first index wheel 12 has indexed.

Ratchets/pawls link the index driving ratchet wheel 46 to both first and second index wheels 12,14, as well as linking both index wheels 12,14 to the rear chassis 6, and the take-up drum 30 to the take-up drum ratchet wheel 50. The inhaler device 2 aims to ensure that all of these ratchet reset points are 'slaves' to the commitment points at which the slider 58 is released.

At the commitment point on mouthpiece opening, the slider 58 is forced down, or radially inwards, into the index driving ratchet wheel 46 by the peel driving ratchet wheel 48 by the angled surfaces provided on recesses 88,156. This results in a small final rotation in the index driving ratchet wheel 46 when the slider 58 is released and the peel driving ratchet wheel 48 is allowed to rotate. This final rotation provides a window for the resetting of ratchets, specifically those associated with the movement of the second index wheel 14 and the movement of the index driving ratchet wheel 46 relative to the first index wheel drive gear 42. Since they occur in that final section of movement of the index driving ratchet wheel 46, they will be tied to the movement of the peel driving ratchet wheel 48, and will be impossible to actuate separately.

On the return stroke, as the mouthpiece cover 10 is closed, the commitment point occurs when the peel driving ratchet wheel 48 has been rotated enough to push the slider 58 back out of engagement with the index driving ratchet wheel 46, causing it to rotate and effect the indexing of the first index wheel 12, with its associated ratchet-pawl reset. This indexing is thus tied to the commitment point, and neither can be actuated separately.

Various modifications to the described inhaler device are possible without departing from the scope of the overall inventive concept. For example, rotation of the first and second index wheels 12,14 may be selectively prevented by interacting curved Geneva lock surfaces provided on the first and second index wheels 12,14 and on the peel driving ratchet wheel 48, rather than by the first and second pawls 72,74 as described.

The peeling of the lidding sheet/foil may also be achieved by alternative means. For example, the index wheel may be arranged to move linearly while it turns and indexes the strip, effectively causing it to roll along the strip by one blister-pocket, before locking its rotation and translating its axle back to its original position. This would allow the lidding foil take-up system to peel the lidding foil as the index wheel translates. Alternatively, a movable peel beak may be provided to rotate with one of both of the first and second index wheels 12,14 during indexing, before being released to allow peeling of the lidding foil. These arrangements both essentially provide a moving peel front location, which avoids the need to actively back off the lidding foil tension and provide slack, and subsequently reapply tension to perform the peeling operation. This potentially allows a less complex overall mechanism to be provided.

Figure 24:
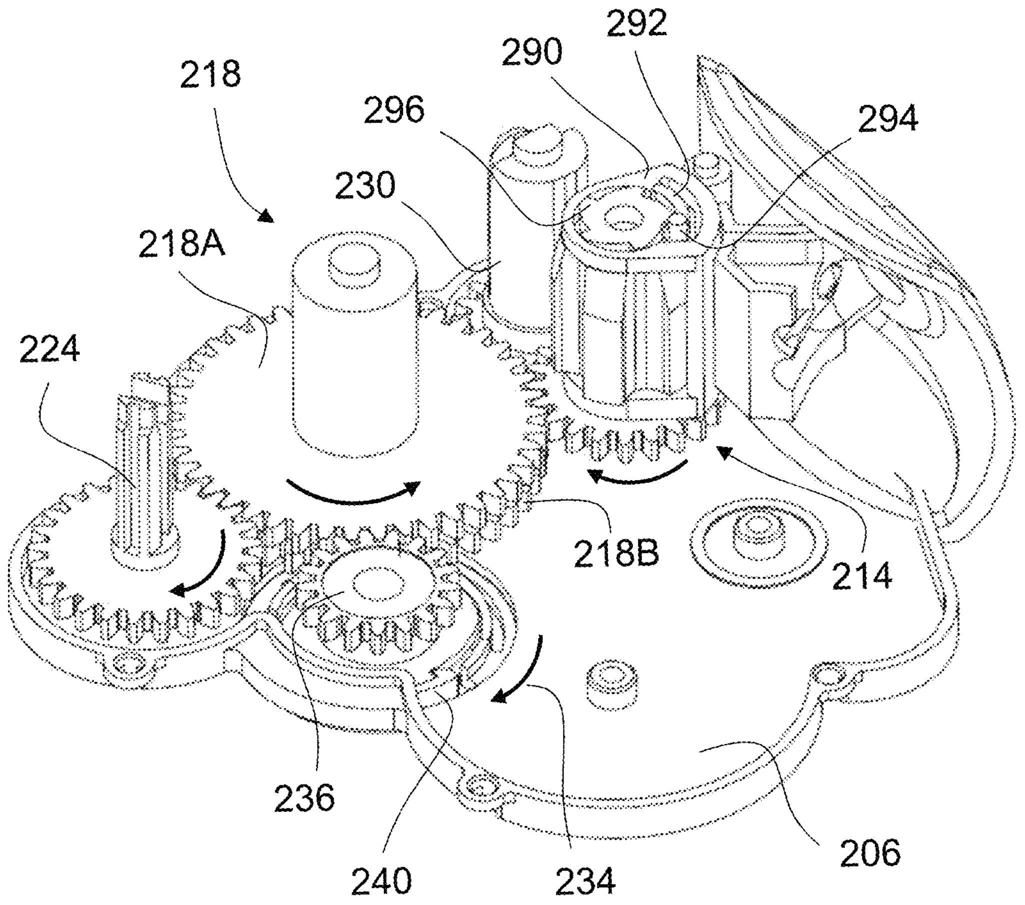
FIG. 24 shows an example of an alternative peel mechanism.

An example of a moving peel-beak arrangement is shown in FIG. 24. Briefly, the Figure shows one side of a mechanism for an alternative inhaler device, with a single index wheel 214 visible. The illustrated mechanism also includes a central input hub gear 236, a take-up drum/hub 230 for used lidding sheet or foil, and a spool wheel 224 for receiving used base/base foil.

A moving peel-beak component 290 is provided around the index wheel 214. The moving peel-beak component 290 defines the peel front, and comprises a ratchet pawl 292, which is shown in engagement with ratchet teeth 296 provided on or associated with the indexing wheel 214. A pin 294 is provided on the ratchet pawl 292 so that a sprung peel actuator (not shown) can disengage the ratchet pawl 292 from the ratchet teeth 296 when required.

A storage hub 218, for storing the unused blister strip, is also shown. The storage hub 218 comprises front, or inner, and rear, or outer, gears 218A,218B with a torsion spring arranged therebetween. The inner gear 218A is driven by rotation of the input hub gear 236 as shown, and this drive is directly transferred to the index wheel 214 and spool wheel 224 to advance the blister strip. The take-up drum/hub 230 is, instead, engaged with the outer gear 218B. As the moving peel-beak 290 rotates with the index wheel 214, the tension generated in the lidding foil rotates the take-up drum/hub 230 against the take-up direction, driving the outer gear 218B in the opposite direction to the inner gear 218A and charging the torsion spring in the storage hub 218.

When a dose is to be opened, the peel actuator (not shown) engages with the pin 294 to release the ratchet pawl 292 from the ratchet teeth 296. This frees the moving peel-beak component 290 to rotate relative to the index wheel 214. The charged torsion spring then drives the rear/outer gear 218B to take up the lidding foil and peel the dose open as the index wheel 214 is held stationary.

The moving peel-beak component 290 also includes an extra section of airway (not shown) to provide a passageway between a peeled dose/blister on the index wheel 214 and the mouthpiece of the inhaler device.

The mechanism shown in FIG. 24 is shown assembled against a rear plate 206 of an inhaler to make up the left-hand side of a complete mechanism. The input hub gear 236 is surrounded by a rear ratchet ring 240 which is connected through the rear plate 206 to a mouthpiece cover (not shown), so that the mechanism is only driven in the direction of arrow 234. This drive occurs when the mouthpiece is moved from a closed position to an open position.

Figure 25:
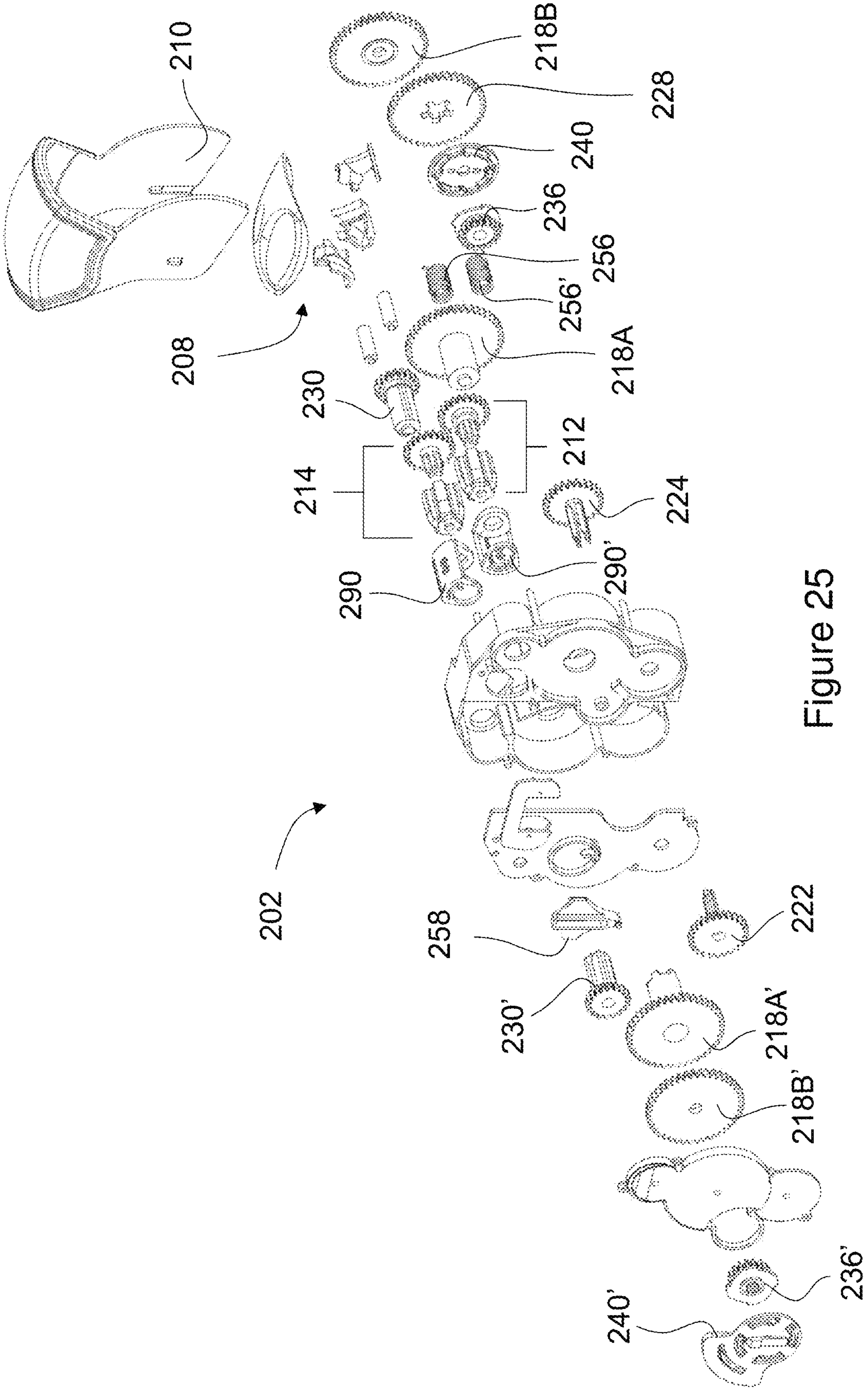
FIG. 25 shows an exploded view of an inhaler according to a second embodiment of the present invention, incorporating the alternative peel mechanism of FIG. 24.

An exploded view of a complete inhaler 202 incorporating the moving peel-beak component 290, is shown in FIG. 25. The rear plate 206 is omitted from the exploded view, but the remaining components discussed in FIG. 24 are shown, along with the torsion spring 256 provided between the front and rear gears 218A,218B of the storage hub 218. Also shown are the mouthpiece and airway manifold 208, the mouthpiece cover 210, and a linearly moving peel actuator 258.

Equivalent components making up the right-hand side of the mechanism are also shown in FIG. 25. The right-hand side of the mechanism is driven by a front input hub gear 236', which is surrounded by a front ratchet ring 240'. The right-hand index wheel is given the reference 212, and the right-hand spool wheel 222, with other components given equivalent reference numerals to those on the left-hand side, distinguished with a prime symbol. The left and right halves of the mechanism are generally similar, but an additional gear 228 is provided towards the rear of the assembly to form part of the right-hand storage hub 218'.

Briefly, this second embodiment of an inhaler according to the invention comprises a moving mouthpiece cover connected to a central hub comprising a pair of unidirectional ratchet wheels each associated with a separate gear train. This allows the action of closing the mouthpiece cover to advance a first index wheel, while opening the mouthpiece cover advances a second index wheel. The central hub also incorporates a cam track for controlling movement of the spring peel actuator. The peel actuator is released to free a pair of peel-beak components as described above when the mouthpiece cover is opened beyond an intermediate position or commitment point, and is reset on mouthpiece closure. The peel actuator is constrained to a linear motion.

After a dose is inhaled, the right-hand side of the mechanism is the first to advance, so the right-hand side components will hereafter be referred to as the first index wheel 212, first spool wheel 222 etc.

Figure 26:
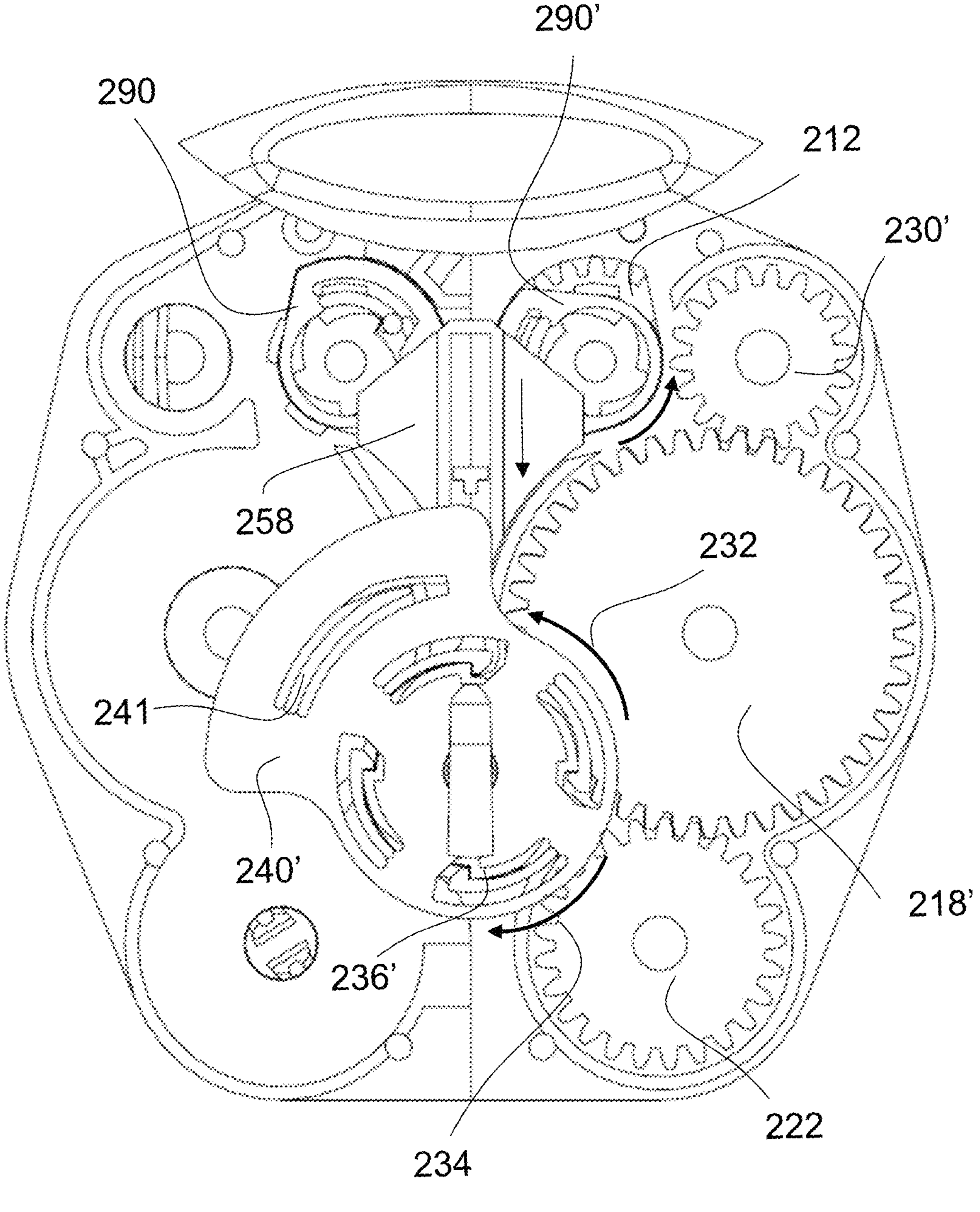
FIG. 26 shows a front view of the mechanism of the inhaler of FIG. 25.

A front view of the assembled mechanism is shown in FIG. 26. As shown the mouthpiece cover has been closed after a dose has been inhaled. The front ratchet ring 240' has rotated the front input gear 236' in the direction of arrow 232 as the mouthpiece was closed, advancing the right-hand side of the mechanism to rotate the first index wheel 212 by a single step/dose and rotating the first peel beak component 290' to the position shown.

During closure of the mouthpiece cover 210, the input gear 236' directly drives inner gear 218A' of the storage hub 218', and this direct drive is transferred to the first index wheel 212 (via the additional gear 228—see FIG. 27) and first spool wheel 222 to advance the blister strip. The first take-up drum/hub 230' is engaged with the outer gear 2186'. As the moving peel-beak 290' rotates with the index wheel 214, the tension generated in the lidding sheet/foil rotates the take-up drum/hub 230 against the take-up direction, driving the outer gear 2186' in the opposite direction to the inner gear 218A' and charging the torsion spring 256' in the first storage hub 218. A peel actuator cam track 241 provided in the front ratchet ring 240' also moves the peel actuator 258 vertically downwards to the position shown, against the force of a biasing spring, so that the first peel-beak 290' is not disengaged from the first index wheel during rotation.

When the mouthpiece cover 210 is opened, the front ratchet ring 240' is rotated in the direction of arrow 234. This causes the ratchet pawls 250' to deflect, so that no drive is transmitted to the mechanism during mouthpiece opening.

Figure 27:
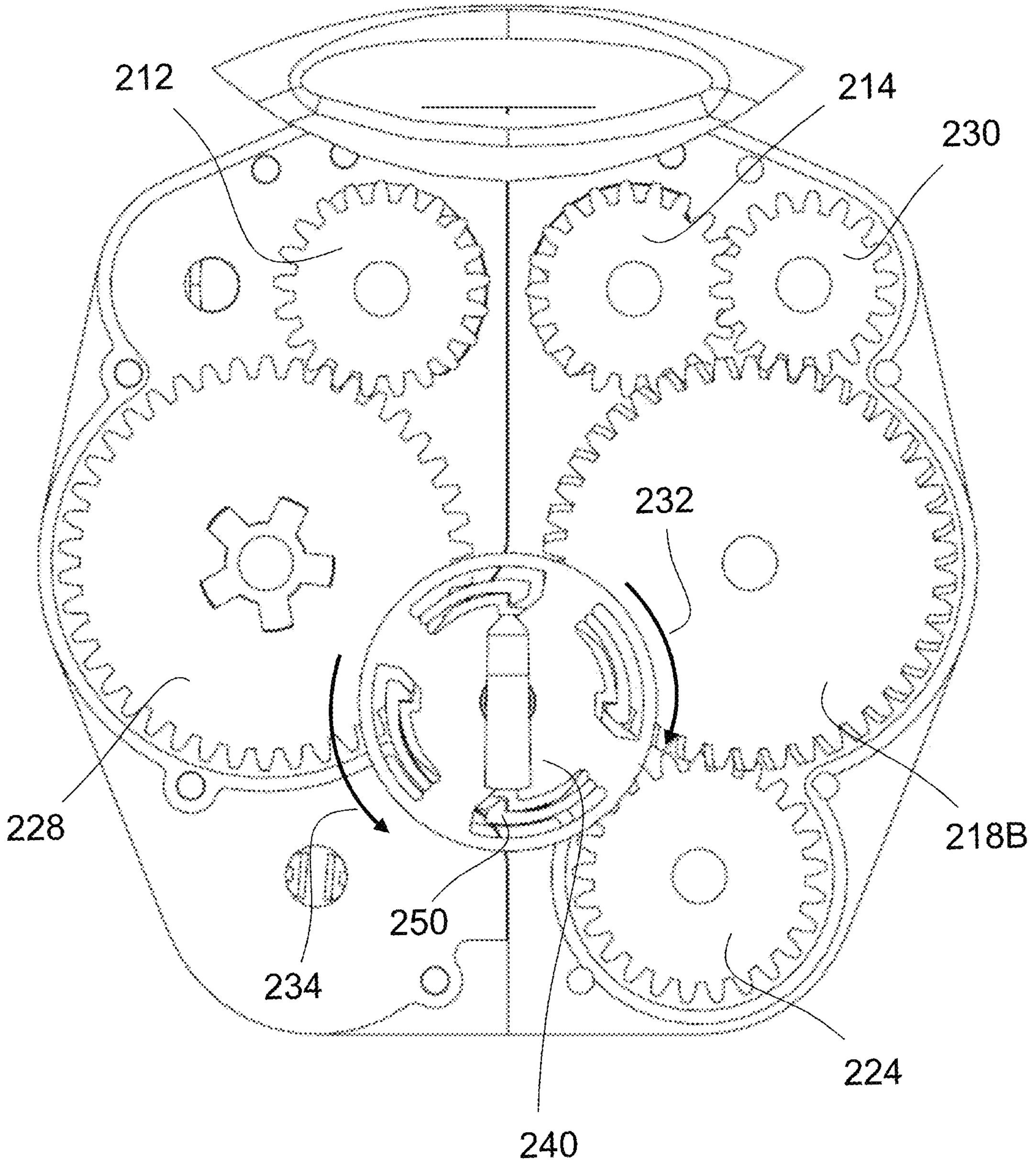
FIG. 27 shows a rear view of the mechanism of the inhaler of FIG. 25.

FIG. 27 shows a rear view of the assembled mechanism. The rear faces of the components shown in FIG. 25 are visible, along with the additional gear 228 which is engaged with the first index wheel 212. The additional gear 228 is directly connected to the inner gear 218A' of the first storage hub 218', so that rotation of this as the mouthpiece cover is closed directly drives the first index wheel 212 as described in FIG. 26. Rotating the rear ratchet ring 240 in the direction 234 by opening the mouthpiece cover drives the second index wheel 214, second spool wheel 224, etc as described in FIG. 25. The ratchet pawls 250 deflect to allow rotation of the rear ratchet ring 240 in the direction of arrow 234 without advancing the mechanism during mouthpiece closing. The additional gear 228 is not engaged with the rear input gear 236, and so is not driven by any movement of the rear ratchet ring 240.

It will be understood, therefore, that the two unidirectional ratchet rings 240,240' drive different halves of the mechanism on closing and opening of the mouthpiece. In particular, the first index wheel 212 is driven only during closure of the mouthpiece 210 and the second index wheel 214 is driven only during mouthpiece opening.

Figure 28:
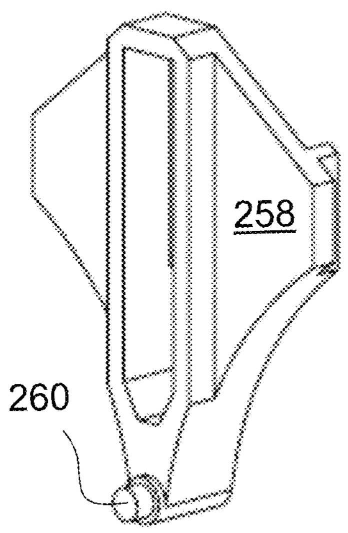
FIGS. 28 and 29 show a peel actuator component from the inhaler of FIG. 25.
Figure 29:
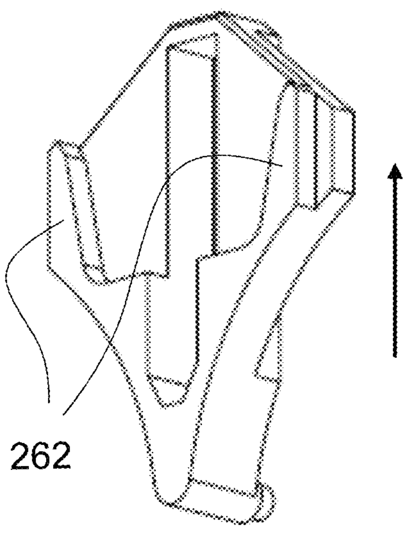

The peel actuator 258 is shown in isolation in FIGS. 28 and 29. The front view of FIG. 28 shows a pin 260 at the lower end of the peel actuator 258 for engagement with the cam track 241 in the front ratchet ring 240'. FIG. 29 shows a pair of prongs 262 on the rear of the peel actuator 258. In use, the prongs 262 simultaneously engage with the pins 294 of the ratchet pawls 292 of both peel-beaks 290,290' to release the peel-beaks 290,290' and allow the take-up drums/hubs 230,230' to rotate and withdraw the lidding foil from each of two blister strips, exposing a dose for inhalation.

Figure 30:
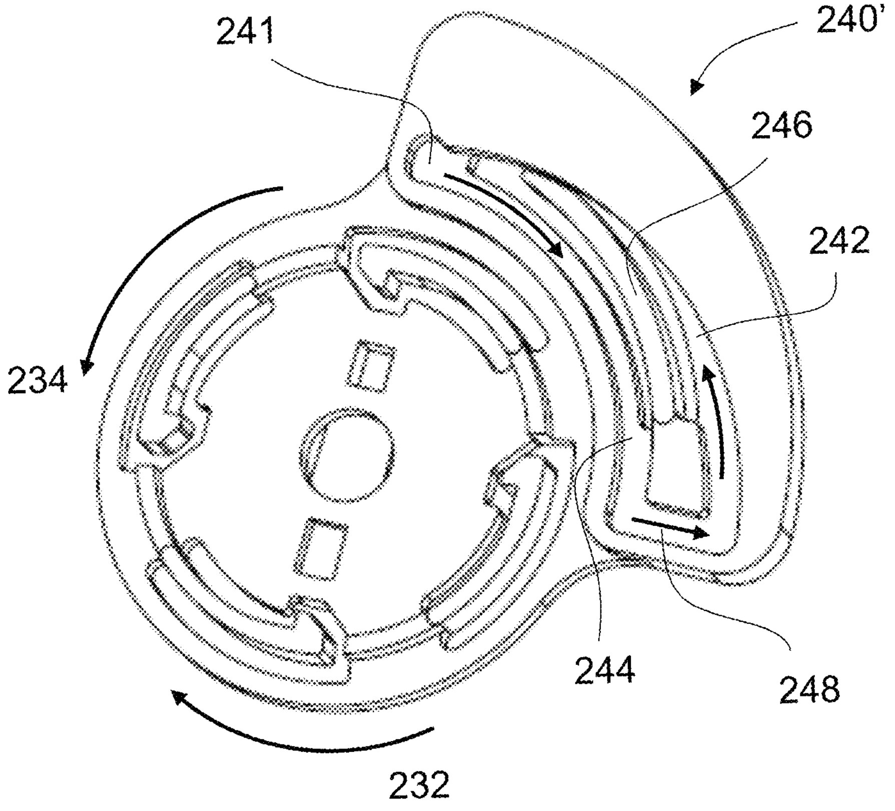
FIG. 30 shows a ratchet component from the inhaler of FIG. 25.

FIG. 30 shows the rear side of the front ratchet ring 240', providing detail of the cam track 241 for guiding the pin 260 of the peel actuator 258. The path of the pin 260 through the cam track is illustrated with arrows. When a dose has been released from the inhaler, an outer track 242 urges the pin 260 inwards relative to the front ratchet ring 240' during rotation 232 caused by closure of the mouthpiece cover 210. This moves the peel actuator 258 downwards against the force of a spring until the mouthpiece cover 210 is fully closed. During opening 234 of the mouthpiece cover 210 the pin 260 is instead constrained by an inner track 244, which holds the peel actuator 258 in a withdrawn position. A resilient divider 246 is provided between the outer and inner tracks 242,244 to provide the outer wall of the inner track 244. The divider 246 deflects as the pin 260 approaches the left end (as shown) of the cam track 241 during closure of the mouthpiece cover to allow the pin 260 to move from the outer track 242 to the inner track 244. This is the position shown in the front view of FIG. 26. The divider 246 then returns to the position shown in FIG. 30 to prevent the pin 260 returning to the outer track 242 during subsequent opening of the mouthpiece cover.

When the mouthpiece cover 210 is fully open, the pin 260 reaches the right end (as shown) of the cam track 241, and can then move into a straight part 248 of the cam track 241, which is arranged substantially vertically relative to the inhaler body in the fully open position. This provides a commitment point, occurring shortly after the second index wheel 214 has been advanced by one step/dose, at which the peel actuator 258 is freed to move vertically, under the force of its spring, and release the peel-beaks 290,290' to uncover a dose for inhalation by a patient.

A further embodiment of the present invention is illustrated in FIGS. 31-35. This embodiment comprises a single double-height index wheel for receiving two blister strips, although it should be clear that the mechanism could be provided for a single blister strip if desired. A unidirectional ratchet wheel drives the indexing system as the mouthpiece cover is opened. A sprung idler comprising a torsion spring, and having a similar construction to the storage hub 218 described in FIG. 24, is provided in a drivetrain between the mouthpiece cover and a lidding sheet take-up component, and a moving peel-beak component similar to that described above is included. A cam track provided on the chassis of the inhaler engages with a pin on the ratchet pawl of the moving peel-beak component to free it when the index wheel and peel-beak component to rotate past a commitment point corresponding with an intermediate position of the mouthpiece cover during opening.

Figure 31:
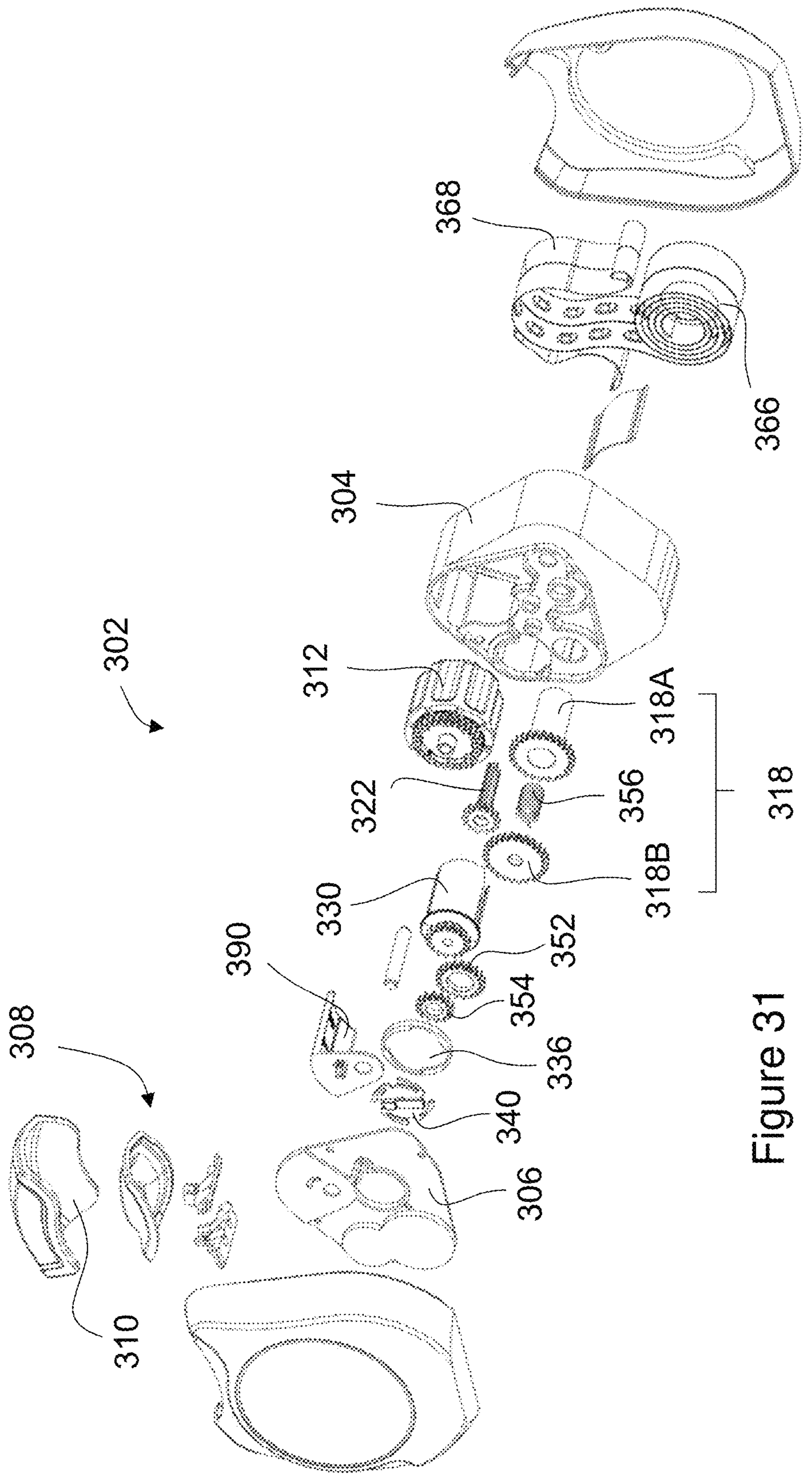
FIG. 31 shows a rear exploded view of an inhaler according to a third embodiment of the invention.

FIG. 31 shows an exploded view of this third embodiment. The exploded view is taken from the rear, and therefore shows the rear sides of the various components of the inhaler device 302 as they are arranged within an outer housing.

The mechanism is formed from several geared components are held in place by a mid chassis 304 and a rear plate 306.

Two blister strips 366,368 are also shown side by side so that the individual pockets of medicament in each strip sit side by side in recesses in an indexer 312 in the form of a double-height index wheel located towards the top of the inhaler. A moving peel-beak component 390 is also provided.

Also shown are a spool wheel 322, for advancing and receiving the used base sheets/foils of the blister strips 366,368, and a take-up drum 330 for receiving used lidding sheet/foil. A sprung idler 318, formed from front and rear gears 318A,318B with a torsion spring 356 arranged therebetween, along with first and second idler gears 352,354.

A rear ratchet component 340 provides a connection to the mouthpiece cover 310, and fits within a cavity on the rear of a central input hub gear 336 to provide drive to the input hub gear 336 in only one direction.

Figure 32:
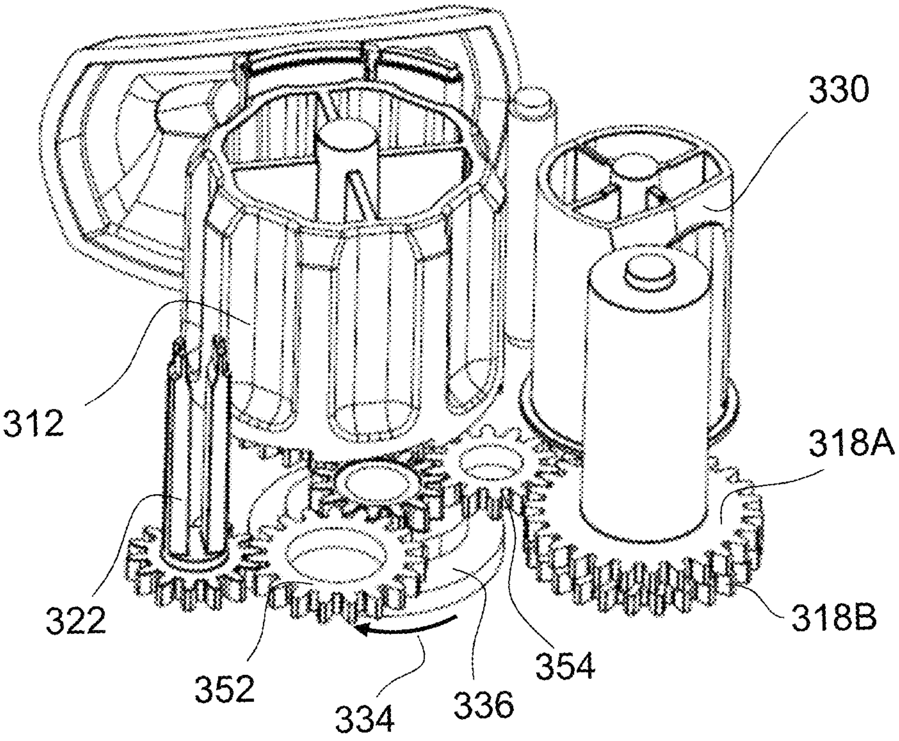
FIG. 32 shows a front perspective view of the mechanism of the inhaler of FIG. 31.

FIG. 32 shows the assembly of the mechanism within the inhaler device 302. The input hub gear 336 is driven in the clockwise direction 334 when the mouthpiece cover 310 is opened, and directly drives the index wheel 312 and first and second idler gears 352,354. The first idler gear 352 transmits drive to the spool wheel 322, and the second idler gear 354 transmits drive to the front gear 318A of the sprung idler.

Figure 33:
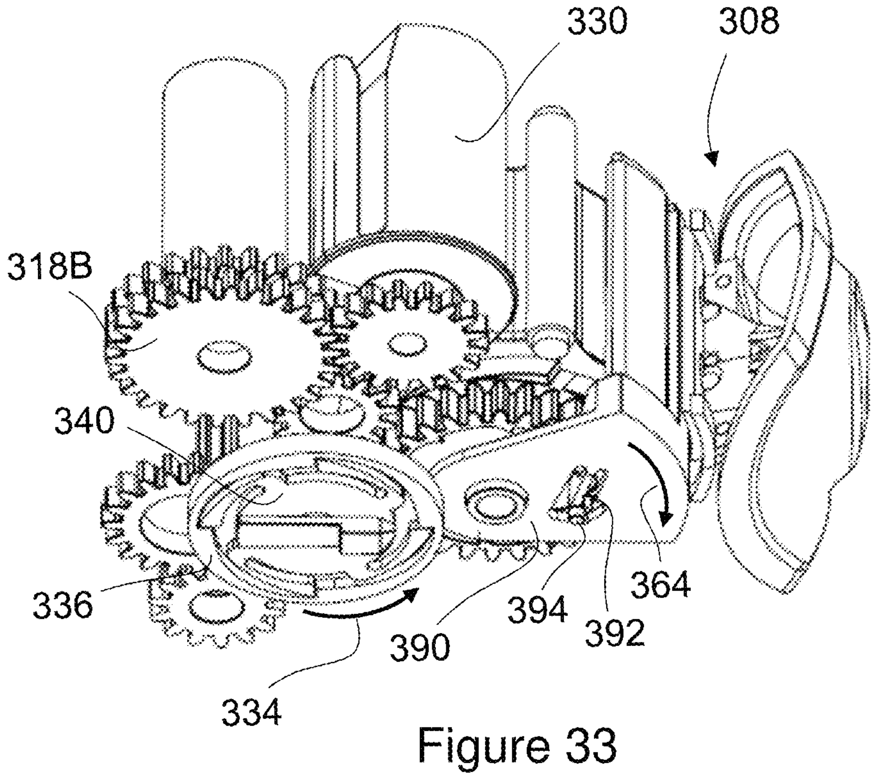
FIG. 33 shows a rear perspective view of the mechanism of the inhaler of FIG. 31.

FIG. 33 shows a rear view of the inhaler mechanism. The moving peel-beak component 390 can be seen surrounding part of the index wheel 312, occupying a space between the index wheel 312 and the mouthpiece and airway manifold 308. The rear gear 318B of the sprung idler 318 is shown engaged with the take-up hub 330, so that the torsion spring 356 can accommodate required differences in rotation of the take-up hub 330 and other components in the mechanism.

The engagement of the rear ratchet component 340 with the input hub gear 336 can be seen, and it will be understood that the ratchet component 340 will drive the hub gear 336 when rotated in the direction or arrow 334 during mouthpiece cover opening, but can rotate relative to hub gear 336 the when rotated in the opposite direction as the mouthpiece cover 310 is closed.

It will also be understood that the clockwise rotation 334 (as viewed from the front of the inhaler) of the input hub gear 336 caused by opening the mouthpiece will be transferred to anticlockwise rotation 364 of the index wheel 312 as shown. A hook or pawl 392 can also be seen on the rear of the peel-beak component 390, and a pin 394 is shown proud of the remainder of the pawl 392.

Figure 34:
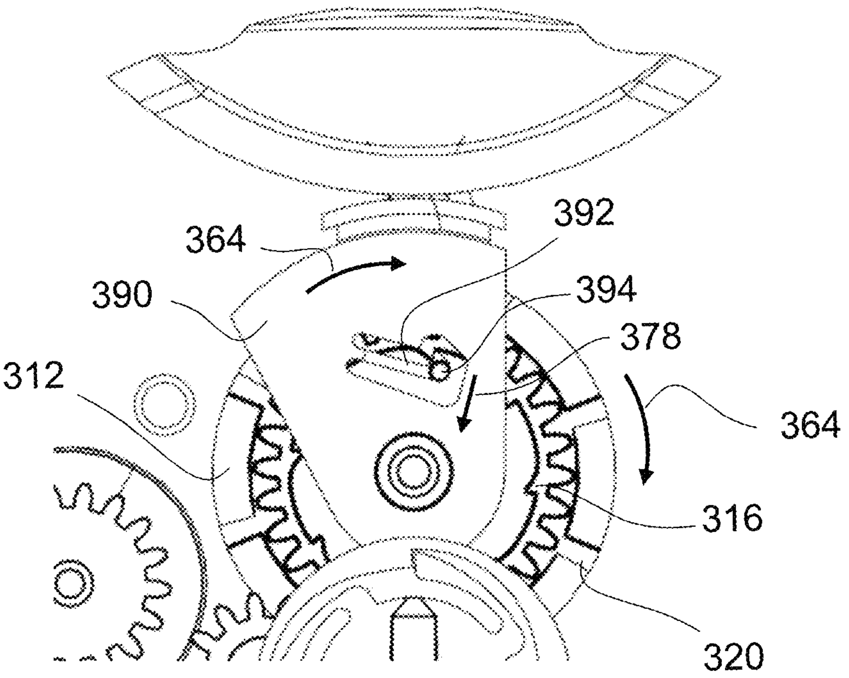
FIG. 34 shows a rear detail view of the mechanism in FIG. 33.

FIG. 34 shows a rear plan view of the index wheel 312 and moving peel-beak component 390 from the mechanism shown in FIG. 33. The pawl 392 on the peel-beak component 390 is shown engaged with one of a series of radially inwardly extending ratchet teeth 316 provided on the rear side of the index wheel 312, so that the peel-beak 390 rotates with the index wheel 312 in the direction of arrow 364 during cap opening. As the index wheel 312 and peel-beak component 390 rotate together, the peel front of the blister strips 366,368 moves with the index wheel. This generates tension in the lidding sheet/foil, which results in reverse rotation of the take-up hub 330 and charges the torsion spring 356 in the sprung idler 318.

Figure 35:
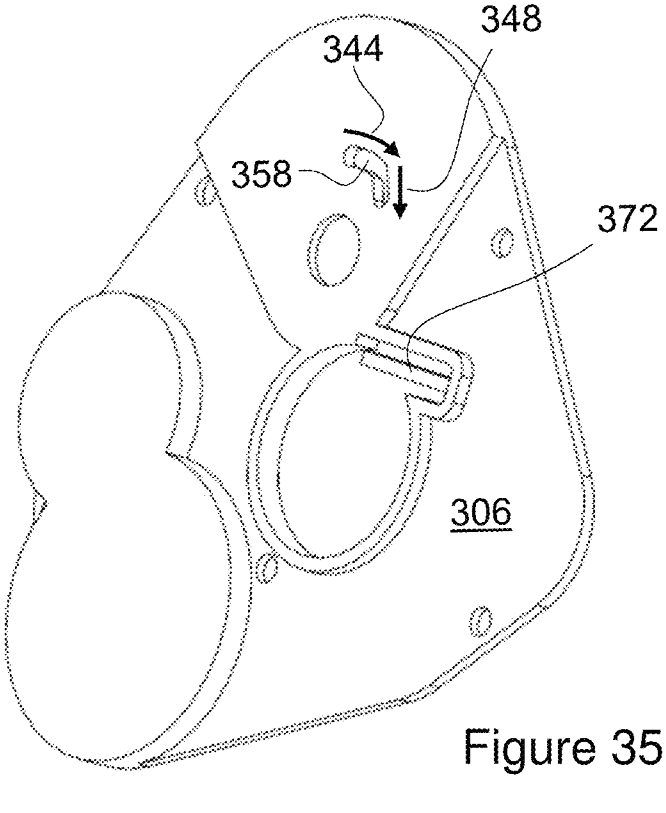
FIG. 35 shows a rear view of a mounting plate from the inhaler of FIG. 31.

FIG. 35 shows the rear plate 306 and the cam track 358 provided therein to act as a peel actuator. As the peel-beak 390 rotates in direction 364 with the index wheel 312, the pin 394 of the pawl 392 passes through the cam track 358 as indicated by arrows 344 and 348. The arc indicated by arrow 344 corresponds with the rotation required to advance the index wheel 312 by just less than one dose/step. Further rotation of the mouthpiece cover 310 beyond this commitment point causes the second, angled, part 348 of the cam track 358 to guide the pin 394 so that the pawl 392 on the peel-beak component 390 is moved radially inwards, as shown by arrow 378 in FIG. 34. The index wheel 312 continues to rotate in the anticlockwise direction 364 as the pawl 392 is withdrawn, so that the previously engaged ratchet tooth 316 on the index wheel 312 moves past the pawl 392. This frees the peel-beak component 390 to rotate clockwise relative to the index wheel 312, with the pin passing back through the cam track 358. The charged torsion spring 356 in the sprung idler 318 then rotates the take-up hub 330 to take up the lidding foil and peel a dose open as the peel-beak component 390 rotates.

Because of the counter rotation of the front and rear gears 318A,318B during the indexing operation, the torsion spring 356 is sufficiently charged to drive the take-up hub 330 the equivalent of two steps or doses. This ensures that the take-up hub re-coils the 'released' lidding sheet (necessary to allow movement of the peel-beak component 390) and also to peel open a new dose.

The pawl 392 on the peel-beak component 390 automatically engages with the next ratchet tooth 316 of the index wheel during this movement. The rear plate 306 also provides a pawl 372 is a that engages with axial ratchet teeth 320 on the rear of the index wheel 312 to prevent reverse rotation of the index wheel 312 while a dose is peeled and to provide resistance to the ratchet component 340 as the mouthpiece is closed ready for the next use.

FIGS. 36-46 show another embodiment of the invention. In this fourth embodiment, a concentric pair of timing gear wheels are rotated by opening the mouthpiece cover to successively drive a pair of index wheels, using Geneva locking and intermittent gearing to effect the desired timing. A cam follower, sprung with a torsion spring to effect bistability, transmits the rotation from the mouthpiece cover to the timing gear wheels, and is also advanced along a cam track in the inhaler chassis by this rotation. Once the mouthpiece cover is opened to an intermediate position, or commitment point, the cam track causes the follower to 'flip' and actuate a push rod, which moves linearly to release the ratchet pawls provided on a pair of moving peel-beak components similar to those described above. This 'flipping' disengages the timing gear wheels. Closing of the mouthpiece cover fully resets the cam follower and re-engages it with the timing gear wheels, while a unidirectional ratchet prevents reverse rotation of the index wheels while the cam-follower is disengaged. A further cam track is provided on one of the pair of index wheels to reset the push rod during mouthpiece opening. The drive from the mouthpiece cover is transferred to the lidding sheet take-up components via sprung biased storage hubs, similar to the sprung biased storage hub 218 of FIG. 24.

Figure 36:
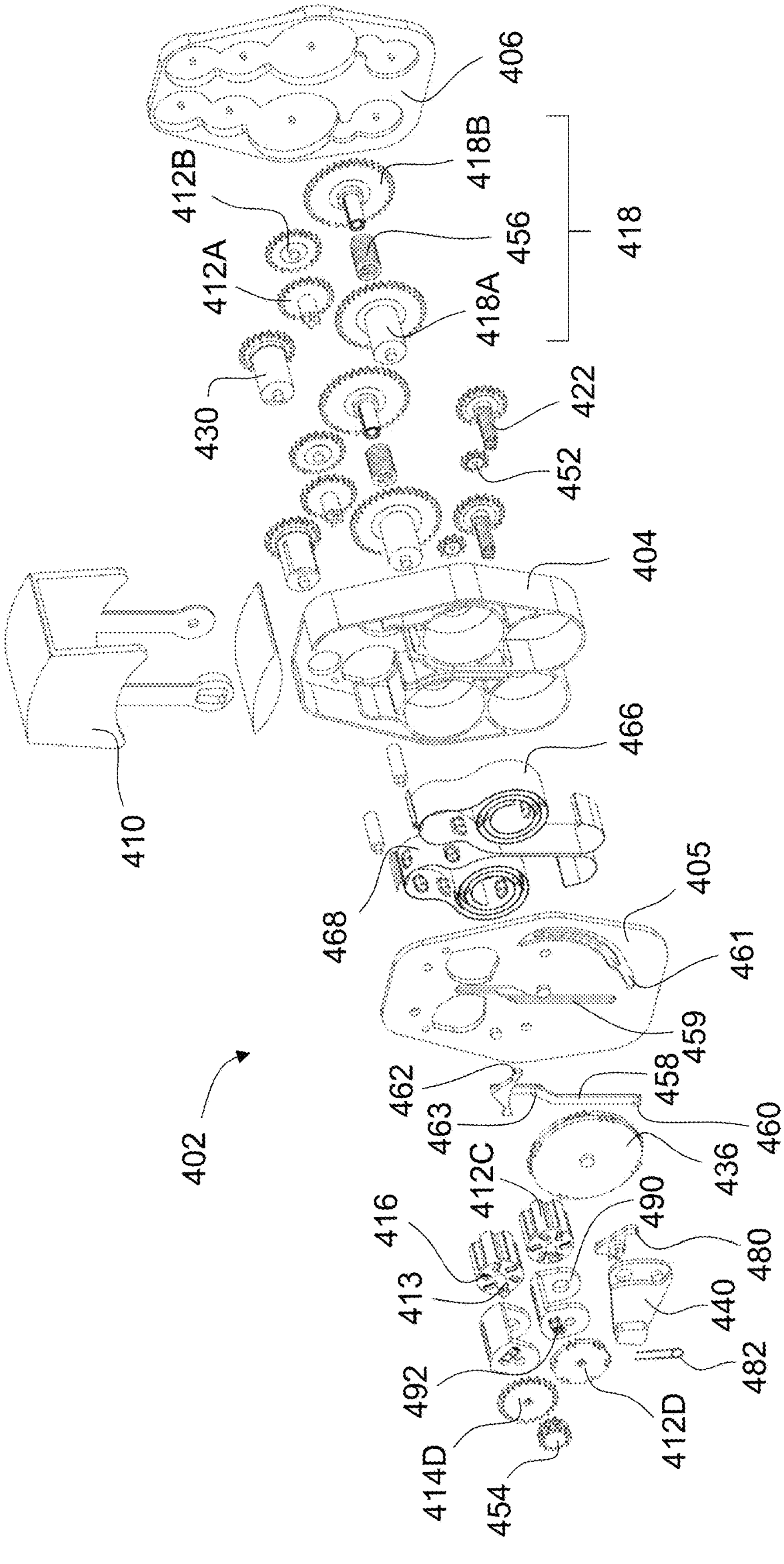
FIG. 36 shows a front exploded view of an inhaler according to a fourth embodiment of the invention.

An exploded view of the inhaler 402, with the outermost housing/body components omitted, is shown in FIG. 36. A mid chassis 404 is shown, along with a front plate 405 and a rear plate 406. Various geared components are assembled between the rear plate 406 and mid chassis 404 to make up separate left-hand and right-hand drivetrains, as indicated by the recesses 407 shown on the rear plate 406.

For clarity, only the components making up the right-hand drivetrain are labelled in FIG. 36. Briefly, these comprise a sprung idler 418 which serves as a storage hub for the unused part of a blister strip 466, a first idler gear 452 and spool wheel 422 to advance the blister strip and coil the used base sheet, and a take-up drum 430 for receiving used lidding sheet/foil. The sprung idler 418 is formed from front and rear gears 418A,418B with a torsion spring 456 arranged therebetween, similar to the equivalent components 218,318 of the second and third embodiments. Also shown are front and rear index output gears 412A,412B which form part of a first indexer 412.

A first index wheel 412C, with pockets for receiving individual blisters of a blister strip 466, and first index drive gear 412D make up the remainder of the first indexer 412, and are shown at the front of the exploded view. When assembled, the rear index output gear 412B is received within the front index output gear 412A but is free to relate relative thereto. The front index output gear 412A is rigidly connected to the first index wheel 412C, and the first index drive gear 412D is rigidly connected to a pin 413 extending from the first index wheel 412C.

A similar arrangement on the left-hand side of the inhaler 402 makes up a second indexer 414 for engagement with a second blister strip 368. As illustrated in FIG. 36, one difference is that the second index drive gear 414D is a simple tooted gear, whereas the first index drive gear 412D provides Geneva locking as will be explained later. A second idler 454 is also associated with the second index drive gear 414D.

A first moving peel peak component 490 is arranged around the first index wheel 412C. The peel-beak component 490 includes a ratchet pawl 492 for selective engagement with recesses 416 in a front face of the first index wheel 412C. When assembled, the front face of the peel-beak component 490 is substantially flush with the front face of the front plate 405.

A central input hub gear 436 is provided in front of the front plate 405. The central hub gear 436 is driven by a cam follower 480 which is moved by an arm 440 connected to the mouthpiece cover 410. A curved cam track 461 is provided in the front plate 405 to control movement of the cam follower 480 relative to the arm 440, as will be described later, against the force of a stabilising spring 482 provided between the cam follower 480 and a further part of the arm 440.

A further guide channel 459 in the front plate 405 receives a peel actuator 458, in the form of a push rod, and constrains it to a linear movement. The peel actuator 458 has a drive pin 460 at its lower end and a pair of prongs 462 at its upper end. The prongs 462 are positioned just proud of the front face of the front plate 405 in the assembled inhaler 402 so that each prong 462 can engage a ratchet pawl 492 of a peel-beak component 490 when the peel actuator 458 moves vertically. The peel actuator 458 also has a guide pin 463 for engagement with a generally circular cam track 441 provided on the rear surface of the hub gear 436.

Figure 37:
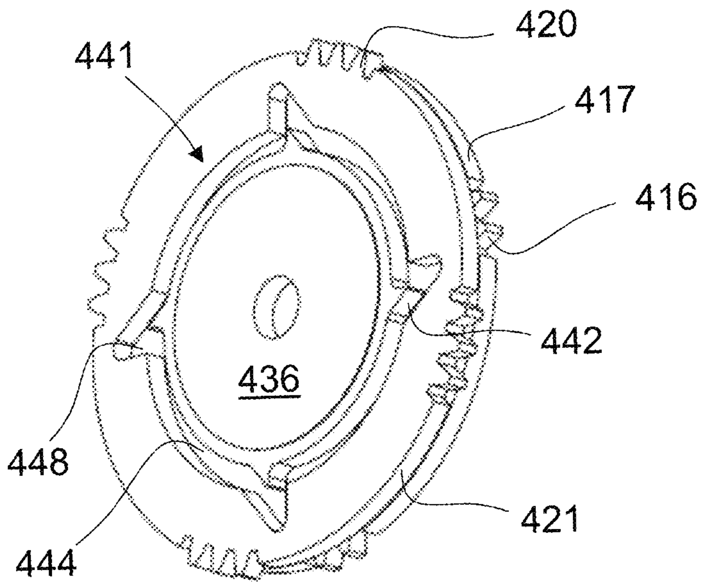
FIGS. 37 to 40 show perspective views of components from the inhaler of FIG. 36.

FIG. 37 shows a rear view of the central hub gear 436, which can be considered to comprise front and rear halves, each in the form of a generally circular plate. Four pairs of teeth 416 are provided at 90 degree spacings around the periphery of a front half, and four groups of three teeth 420 are provided at 90 degree spacings around the periphery of the rear half. Each half of the hub gear 436 therefore provides four isolated geared portions 416,420 separated by smooth radiused sections 417,421. The groups of gear teeth 416,420 on the front and rear halves are offset from one another circumferentially.

A generally circular cam track 441 is also provided on the rear of central hub gear 436. The cam track 441 forms a closed loop with four quarters each having a straight angled section 442, a constant radius section 444 and a straight radially outwardly extending section 448. Each radially outwardly extending section 448 is located between the offset groups of teeth 416,420 on the front and rear halves of the central hub gear 436.

Figure 38:
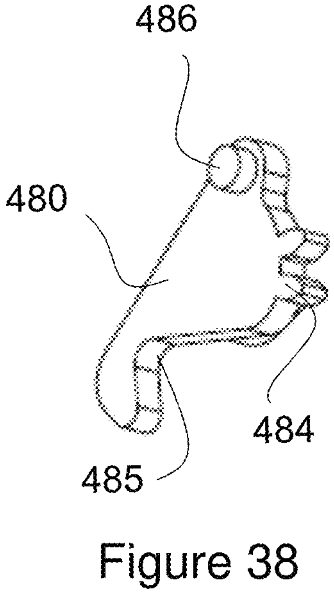

FIG. 38 shows detail of the cam follower 480. A pair of teeth 484 are provided for engagement with the groups of three teeth 420 on the rear half of the hub gear 436. A pin 486 is also provided for engagement with the curved cam track 461, and a recess 485 to engage with the peel actuator 458.

Figure 39:
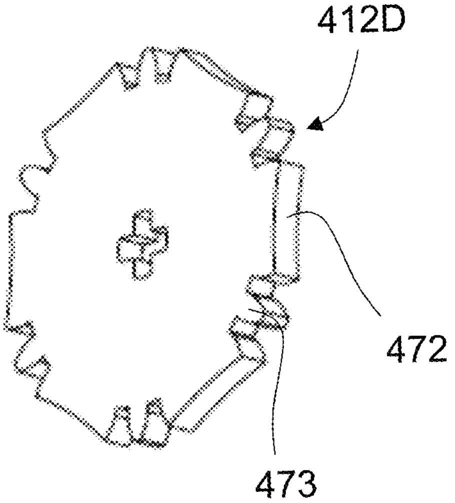
Figure 40:
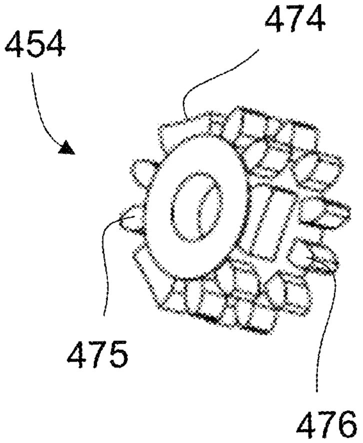

The first index drive gear 412D and second idler 454 are shown in FIG. 39 and FIG. 40 respectively. The first index drive gear 412D has six isolated gear teeth 473, for engagement with the pairs of gear teeth 416 provided on the front half of the hub gear 436, separated by inwardly curved sections 472 around the periphery of the first index drive gear 412D. The radius of each curved section 472 matches the radius of the smooth sections 417 of the hub gear 436. In use, rotation of the central hub gear 436 will advance the first index drive gear 412D when the teeth 416,473 of the components are in engagement, but when the curved sections 417,472 are in engagement the first index drive gear 412D will be held against rotation. Drive gear 412D therefore provides a Geneva lock with the hub gear 436.

The second idler 454 comprises front and rear gear wheels separated by a reduced diameter central section and is shown from the rear in FIG. 40. The rear gear wheel comprises three pairs of gear teeth 475, for engagement with the groups of three teeth 420 on the rear of the central hub, and three inwardly curved sections 474 each having a radius equal to the curved section 421 of the central hub gear 436. The front gear wheel is a standard gear 476 with teeth for engagement with the second index drive gear 414D. The second idler gear 454 therefore provides a similar intermittent drive and locking function for the first index drive gear 414D as that provided by the first index drive gear 412D.

Figure 41:
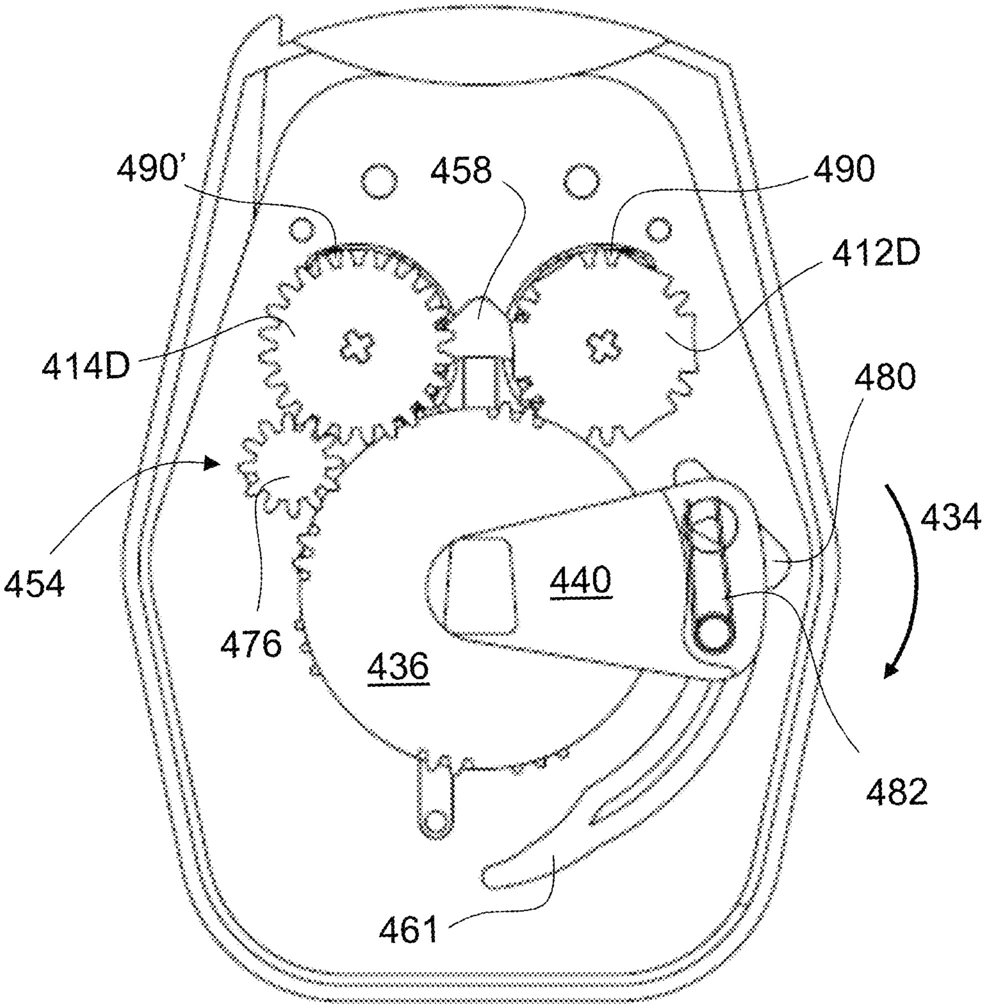
FIG. 41 shows a front view of the assembled mechanism of the inhaler of FIG. 36.

A front view of the assembled mechanism is shown in FIG. 41. As illustrated, the first index drive wheel 412D, and hence the first index, is being held against rotation by the central drive hub. The front gear 476 of the second idler gear 454 sits proud of the central hub gear 436 and is engaged with the second index drive wheel 414D while the rear gear wheel (not shown) engages with the rear half of the central hub gear 436. The reduced diameter central portion of the second idler gear 454 spaces the front and rear gears so that no part of the second idler gear 454 engages with the front half of the central hub gear 436.

The peel actuator 458 is at the top of the guide channel 459, with the prongs 462 sandwiched between the first and second index drive wheels 412D,414D and the first and second moving peel-beak components 490,490'. The cam follower 480 and spring 482 are assembled with the arm 440, which is moved in a clockwise direction 434 when the mouthpiece cover is opened, moving the cam follower 480 along the curved cam track 461. This movement will be explained in the following Figures, where hidden parts of the mechanism are shown in broken lines.

Figure 42:
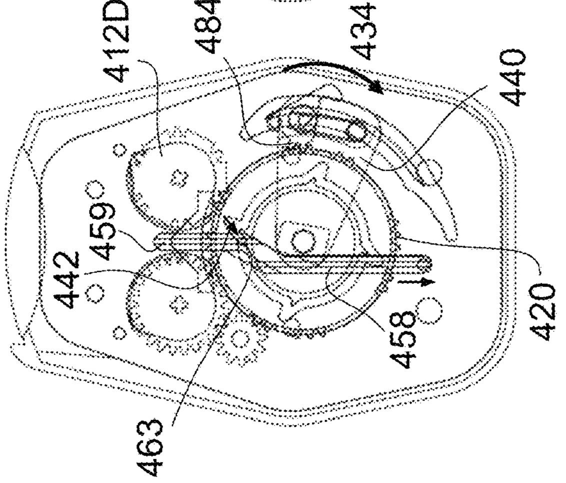
FIGS. 42 to 45 show the operation of the inhaler of FIG. 36.

FIG. 42 shows a view of the mechanism with the mouthpiece cover opened slightly from the position shown in FIG. 41. The arm 440 has rotated clockwise 434, which rotates the central hub gear 436 due to the engagement of the pair of teeth 484 on the cam follower 480 with a group of three teeth 420 on the rear half of the central hub gear 436. The path of the guide pin 463 of the peel actuator 458 along the angled section 442 of the generally circular cam track 441 during this rotation is indicated, and results in a downward movement of the peel actuator 458, away from the top of the guide channel 459. A gear tooth 473 of the first index drive wheel 412D is engaged with a pair of teeth 416 on the hub gear 436 so that further rotation will drive the first indexer 412.

Figure 43:
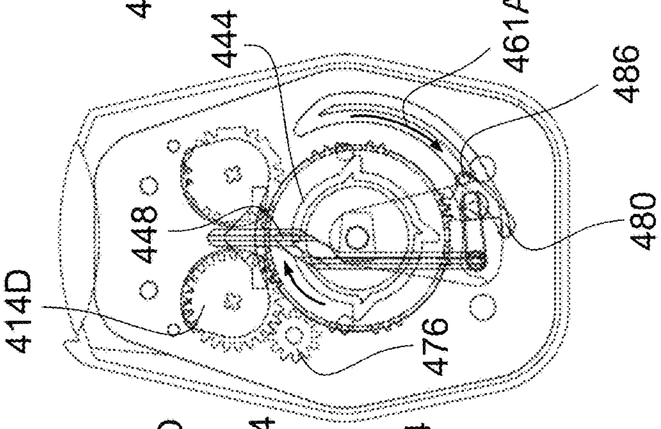

The mechanism is shown after further rotation in FIG. 43. The guide pin 486 of the cam follower 480 has moved through an inner part 461A of the curved cam track 461 as indicated, continuing to drive the hub gear 436. As a result of this rotation, the first index drive wheel 412D has been advanced by one step. A set of three teeth 420 on the front half of the hub gear 436 has moved into and out of engagement with a pair of teeth 475 on the second idler 454, rotating the second idler 454 to drive the second index drive wheel 414D, and thus the second indexer 414, one step. The first and second peel-beak components 490,490' rotate with their respective indexers 412,414 to provide a moving peel front during use, as previously described.

The spacing of the groups of teeth 416,420 on the central hub gear 436 ensures that the second index drive wheel 414D is only advanced after the first after the index drive wheel 412D has been advanced by one step. The peel actuator 458 has been maintained in a withdrawn position during the rotation by engagement of its guide pin 463 with the constant radius section 444 of the generally circular cam track 441.

As shown in FIG. 43, the first and second index drive wheels 412D,414D have both been advanced one step from the position shown in FIG. 42. Both are held against rotation by the engagement of inwardly curved sections 472,474 of the first index drive wheel 412D and the second idler 454 respectively with a curved outer surface of the hub gear 436. The pin 463 of the peel actuator 458 is abutting a radially extending part 448 of the generally circular guide track 441 to resist further rotation of the hub gear 436.

Figure 44:
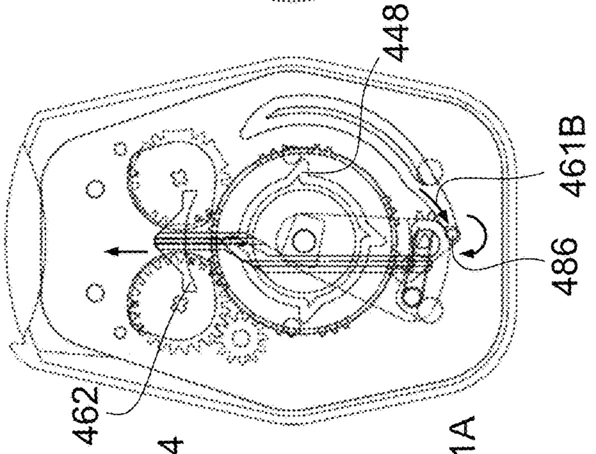

Further rotation of the arm 440 from the position shown in FIG. 43, as the mouthpiece is fully opened, therefore results in relative movement of the cam follower 480 and the central hub gear 436. As shown in FIG. 44, an angled section 461B of the curved guide track 461 urges the guide pin 486 of the cam follower 480 radially outwards during this movement. This causes the cam follower 480 to flip from a first stable state, as shown in FIGS. 41-43, to a second stable state which disengages the pair of teeth 484 from the group of three teeth 420 on the rear half of the central hub gear 436. The flipping action allows the cam follower to move past the hub gear 436, and also causes the recess 485 to engage drive pin 460 of the peel actuator 458 and urge it vertically up to the top of the guide channel 459. This releases the ratchet pawl 492 of each peel-beak component 490, peeling both advanced doses of medicament ready for inhalation. The position shown in FIG. 43 can therefore be considered a commitment point, beyond which the peeling operation is performed.

Figure 45:
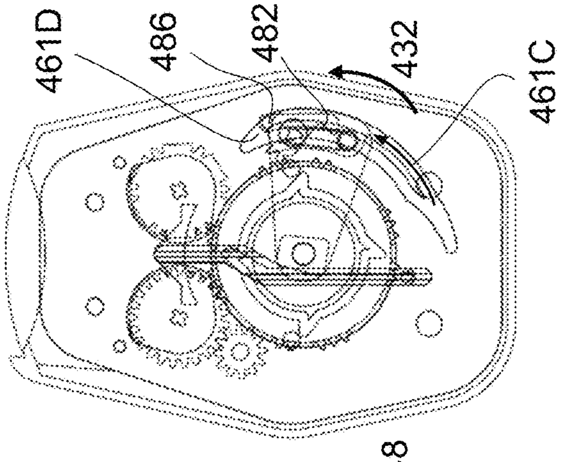

FIG. 45 shows the mechanism being re-set by the movement 432 of closing the mouthpiece cover 410, during which the cam follower 480 is driven by movement of the arm 440. The guide pin 486 of the cam follower 480 passes along an outer part 461C of the curved guide track 461, avoiding any reverse driving of the central hub gear 436. The stabilising spring 482 helps to maintain the cam follower 480 in its second, disengaged, state during this movement.

As shown in FIG. 45, the pair of teeth 484 on the cam follower are adjacent a different group of three teeth 420 on the rear half of the central hub gear 436. Further movement of the arm 440 as the mouthpiece cover 410 is fully closed will move the guide pin 486 of the cam follower 480 through a final straight section 461D of the curved guide track 461. This serves to flip the cam follower 480 back to its first state, engaging the pair of teeth 484 with the group of three teeth 420 on the rear half of the central hub gear 436. The mechanism is thus returned to the position shown in FIG. 41, ready for the next actuation.

Figure 46:
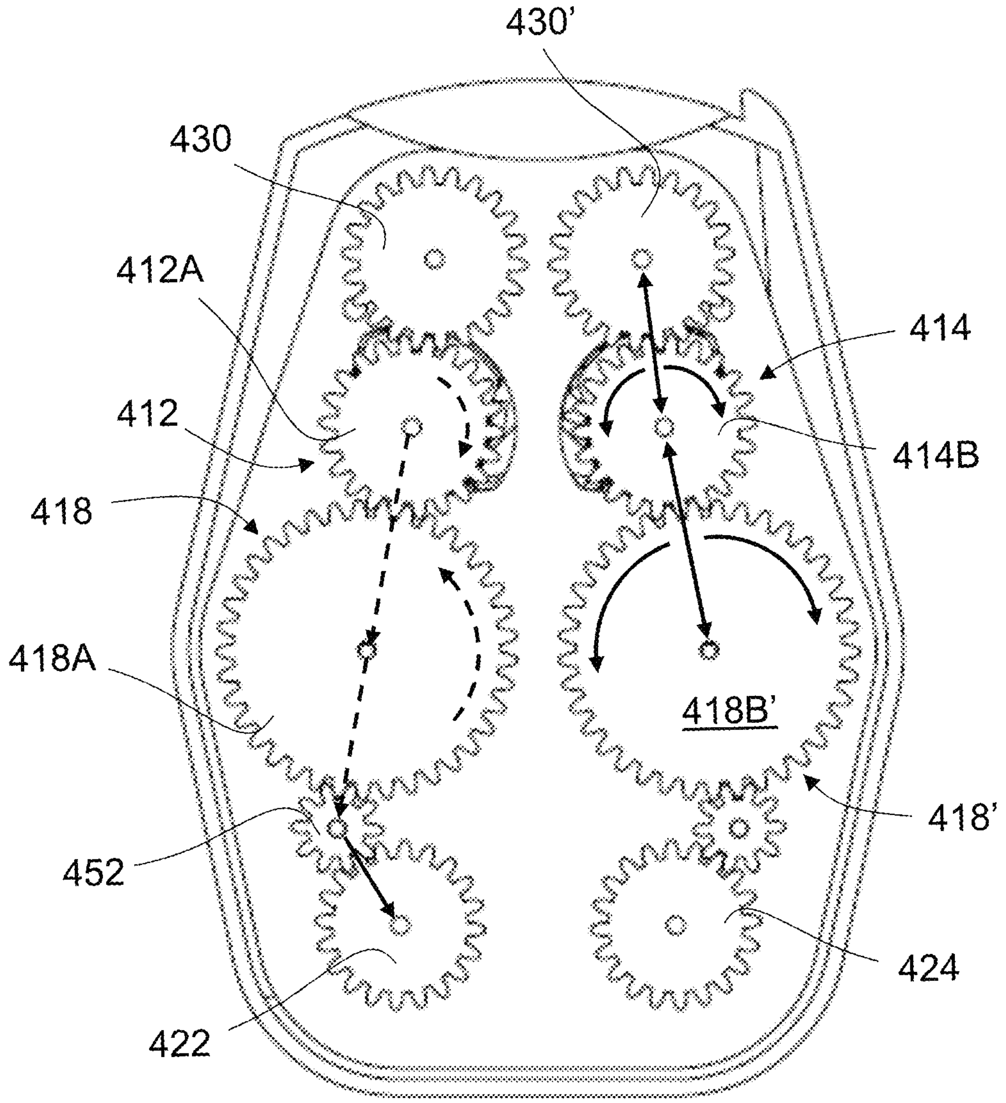
FIG. 46 shows the gearing at the rear of the inhaler of FIG. 36.

FIG. 46 shows the gearing on the rear of the inhaler device 402, ie a view from the rear of the device with the rear plat 406 removed. The first indexer 412 is engaged with the first take-up drum 430 and the first sprung idler 418. The first idler gear 452 is also engaged with the first sprung idler 418 and with the first spool wheel 422 to complete a first drivetrain on one side of the inhaler device 401. A second, separate, drivetrain, incorporating the second indexer 414, is also provided. Arrows have been added to FIG. 46 to illustrate the movement of the drivetrains. For clarity, part of the total movement/drive is illustrated on each of the first and second drivetrains, with broken arrows indicating the engagement and movement of obscured components.

As previously described, the first index drive gear 412D is driven by rotation of the central hub gear 436 during opening of the mouthpiece cover 410. This causes the indicated rotation of the front index output gear 412A, which drives the front gear 418A of the sprung idler 418 as shown. The front gear 418A of the sprung idler 418 is engaged with the first idler gear 452, which in turn is engaged with the first spool wheel 422 to drive and coil the used base sheet. It will be understood that the second drive train operates similarly for the second indexer 414 and second spool wheel 422'.

A strain is applied to the used lidding sheets as the first and second indexers 412,414 are advanced, due to the moving peel beak components 490,490', and this causes rotation of the first and second take-up drums 430,430'. As illustrated on the second drivetrain, the second take-up drum 430' is engaged with the rear index output gear 414B of the second indexer, which acts as an idler transmitting drive to the rear gear 418B' of the second sprung idler 418'. The counter rotation of the front and rear gears 418A',418B' stores energy in the torsion spring 456 during indexing. This energy is released when the peel actuator 458 releases the peel-beak components 490,490', and is sufficient to rotate the second take-up drum 430' to peel a dose.

FIGS. 47-60 show a fifth embodiment of the invention where both the indexing and peeling operations are controlled by a cam plate. A cam track provided on the cam plate engages with pins on a pair of index wheels, and pins provided on the cam plate engage with cam tracks on a pair of moving peel-beak components associated with the index wheels. Torsion springs are provided between the moving peel-beak components and the index wheels. The moving peel-beaks are initially held against rotation while the index wheels are advanced by the cam plate during movement of the mouthpiece cover, and are released only when the mouthpiece cover is opened past an intermediate position or commitment point. No ratcheted components are used anywhere in the fifth embodiment.

Figure 47:
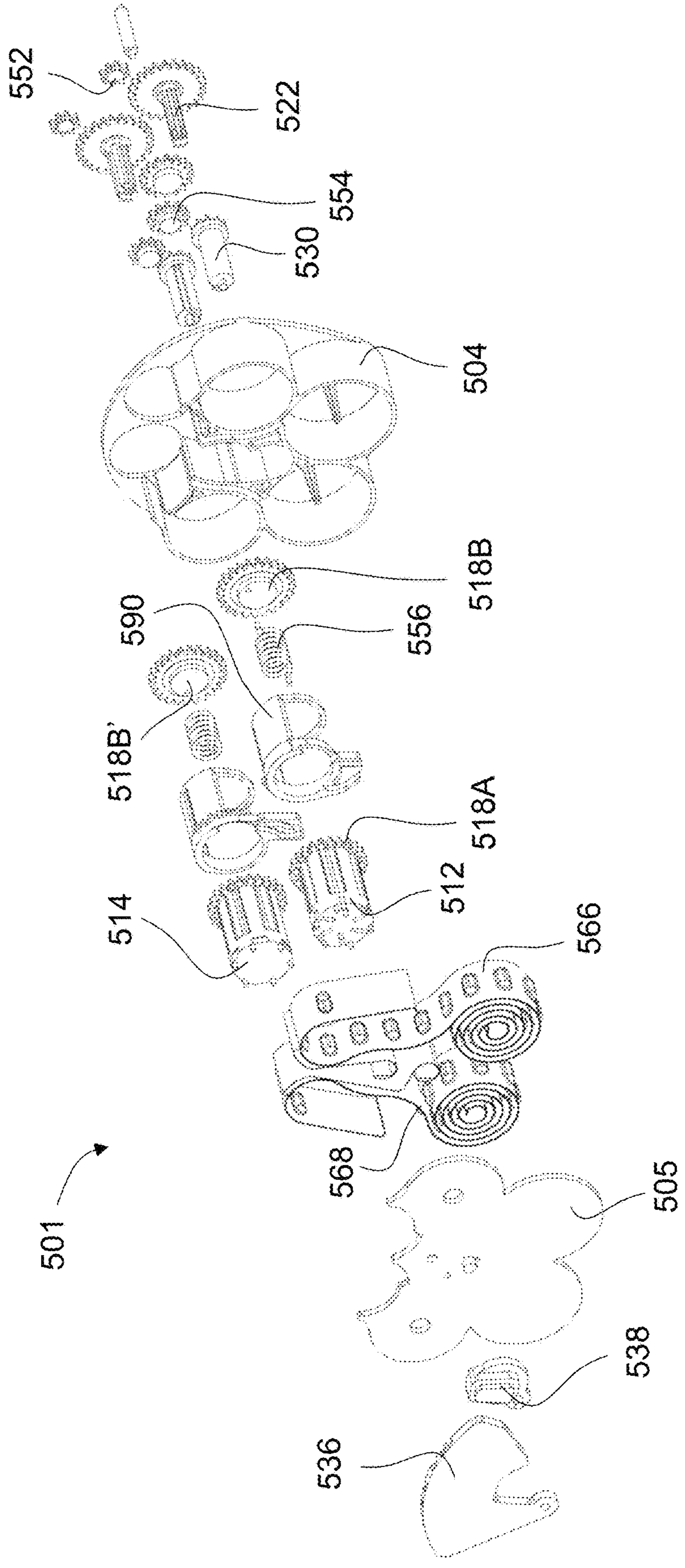
FIG. 47 shows an exploded view of an inhaler according to a fifth embodiment of the invention.

An exploded view of the internal components of an inhaler 501 according to the fifth embodiment is shown in FIG. 47. As in earlier embodiments, a mid chassis 504 and front plate 505 are provided as part of the body of the inhaler 501, and first and second index wheels 512,514 are provided as indexers for first and second blister strips 566,568 respectively. Each of the first and second indexers 512,514 comprises a fixed front gear 518A,518A' and a rear gear 5186, 5186' which is rotatable relative to the front gear 518A, 518A'. A torsion spring 556 is connected between the rear gear 5186,5186' and the remainder of the indexer 512,514. A moving peel beak component 590,590' is provided surrounding each of the first and second indexers 512,514 to vary the position of the peel front, as described in other embodiments.

To the rear side of the mid chassis 504 various geared components are shown which make up first and second geared drivetrains. Only the components making up the first drivetrain, namely a first spool wheel 522, first take-up drum 530 and first and second idlers 552,554 are shown. The geared parts of each of the first and second indexers 512,514 extend past the rear of the mid chassis 504 to engage with the first and second geared drivetrains respectively. Front faces of the first and second indexers 512,514 extend through cut-out sections in the front plate 505, and of the respective moving peel beak components 590,590' are located in front of the front plate 505 so that they are exposed to a cam plate 536. A hub component 538 connects the cam plate 536 to a movable mouthpiece cover (not shown).

Figure 48:
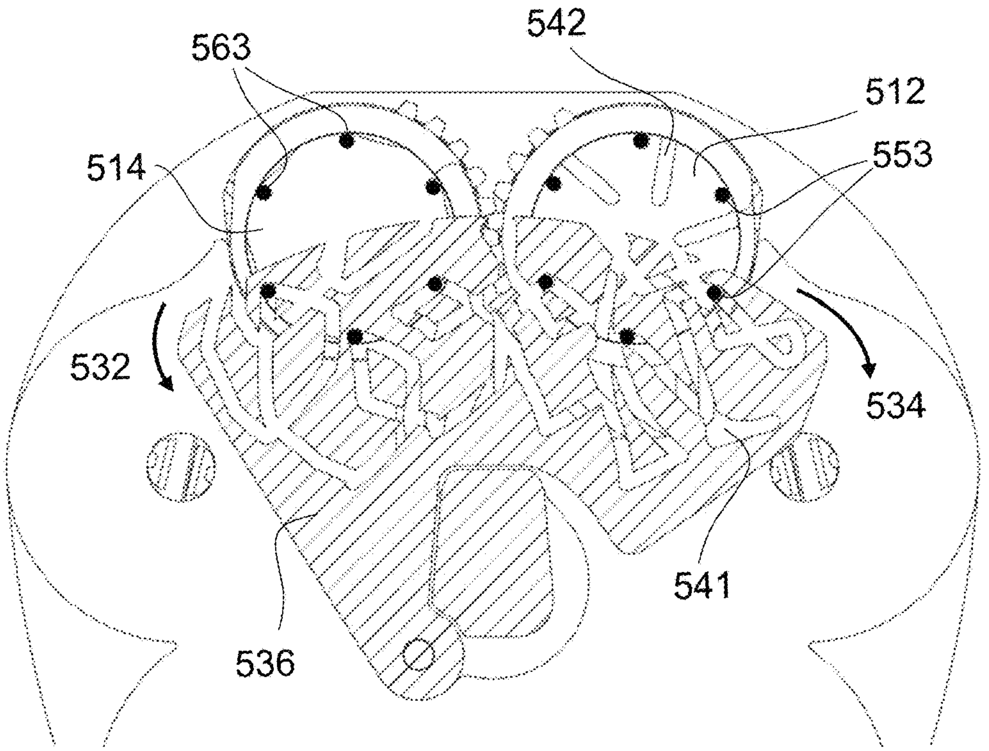
FIG. 48 shows a cross section view of part of the inhaler of FIG. 47 in a first configuration.

FIG. 48 shows a cross section taken through a convoluted cam track 541 provided in the cam plate 536 to illustrate the engagement of the cam plate 536 with the first and second indexers 512,514. A first ring of six pins 553 is provided around the edge of the front face of the first indexer 512, and a second ring of six pins 563 is provided around the edge of the front face of the second indexer 514. The configuration shown in FIG. 48 is where the mouthpiece cover of the inhaler device 501 has been fully closed, moving the cam plate in a generally anticlockwise direction as indicated by arrow 532. Three of each group of six pins 553,563 are engaged with the cam track 541, holding both the first and second indexers 512,514 against rotation.

Figure 49:
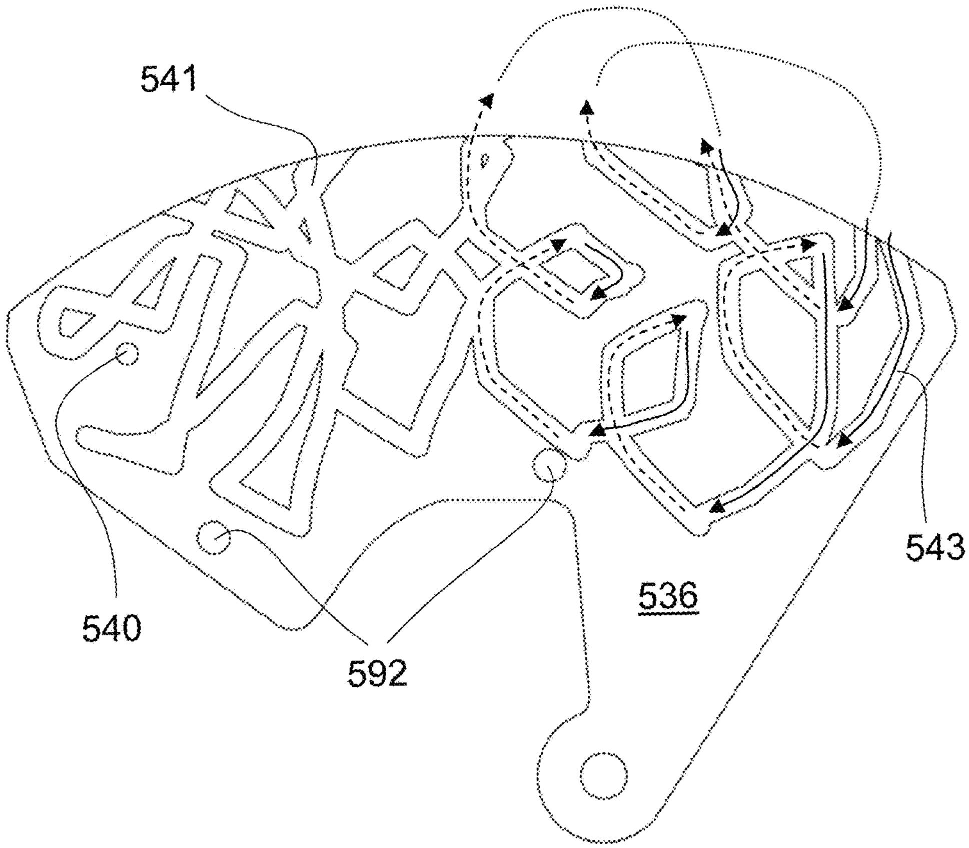
FIG. 49 shows a rear view of a cam plate from the inhaler of FIG. 47.

FIG. 49 shows the path 543 taken by a pin 563 of the second indexer 514 through the cam track 541 during use of the inhaler device 501. The solid arrows indicate the path taken during movement of the cam plate 536 during opening 534 of the mouthpiece cover from the position shown in FIG. 48. This serves to drive the second indexer 514 during opening of the mouthpiece cover. The broken arrows indicate the path taken by the same pin 563 as the mouthpiece cover is closed 532, holding the second indexer 514 against rotation. Each pair of arrows relates to a single opening and closing of the mouthpiece cover.

The rear surface of the cam plate 536 also comprises a driving pin 540 which engages with one of six slots 542 provided on the front face of the first indexer 512 to drive rotation of the first indexer 512 during closure 532 of the mouthpiece cover. Also provided are a pair of peel-beak pins 562 to control movement of the moving peel-beak components 590,590' during use of the inhaler device 501.

Figure 50:
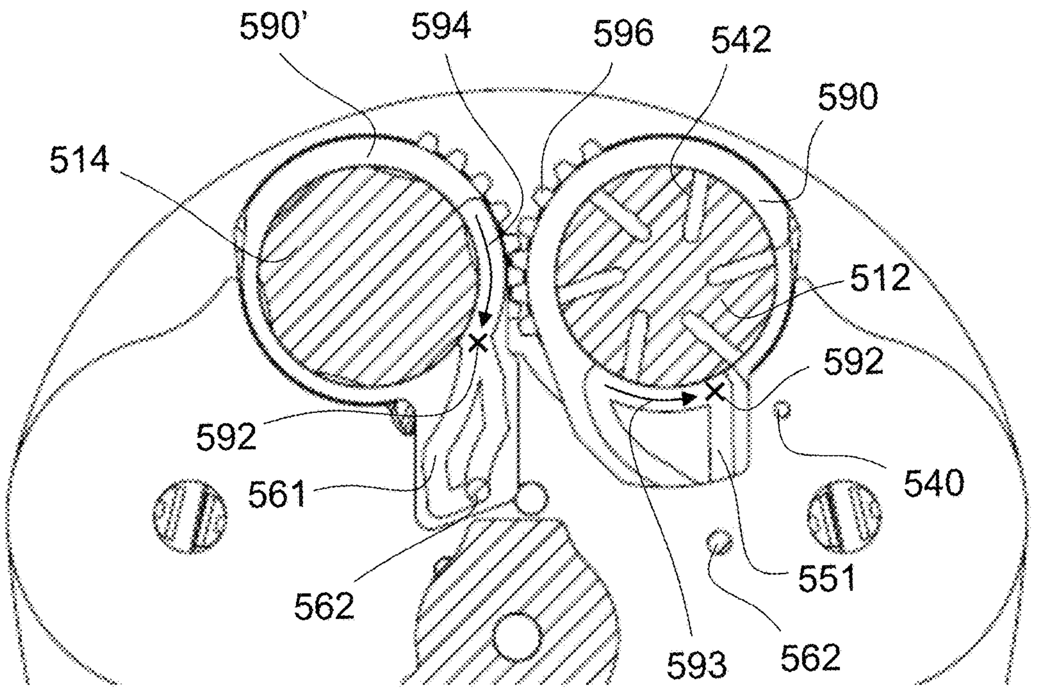
FIG. 50 shows a further cross section view of the inhaler of FIG. 47 in a first configuration.

FIG. 50 shows a further cross section of the device, similar to that of FIG. 48, taken through a plane that intersects the six slots 542 in the first indexer 512. Also shown are first and second peel-beak cam tracks 551,561 in the first and second moving peel-beak components 590,590' respectively. Cross sections of the driving pin 540 and peel-beak pins 562 are also visible.

The first and second moving peel-beak components 590, 590' are free to rotate relative to the first and second indexers, with no engaging latch or ratchet pawl provided. Their movement is instead regulated by the engagement of the peel-beak pins 562 with the first peel-beak cam track 551 or second peel-beak cam track 561. Meshing gear teeth 596 provided on each of the moving peel-beak components 590,590' ensures that their movement is coupled, such that engagement of a peel-beak pin 562 with either peel-beak cam track 551,561 will control movement of both peel-beak components 590,590'.

For example, as shown in FIG. 50, one peel-beak pin 562 is disengaged from the first peel-beak cam track 551, but movement of both peel-beak components 590,590' is still controlled by the engagement of the other peel-beak pin 562 with the second peel-beak cam track 561. Indeed, in most positions of the cam plate 536, one or both of the peel-beak pins 562 is engaged with a peel-beak cam track 551,561 in such a way as to either drive the peel-beak components 590,590' or hold them against rotation. The exception is where the peel-beak pins 562 are in actuation positions marked 592, when the moving peel-beak components 590, 590' are free to rotate as shown by arrows 593 and 594, allowing a dose to peel.

Figure 51:
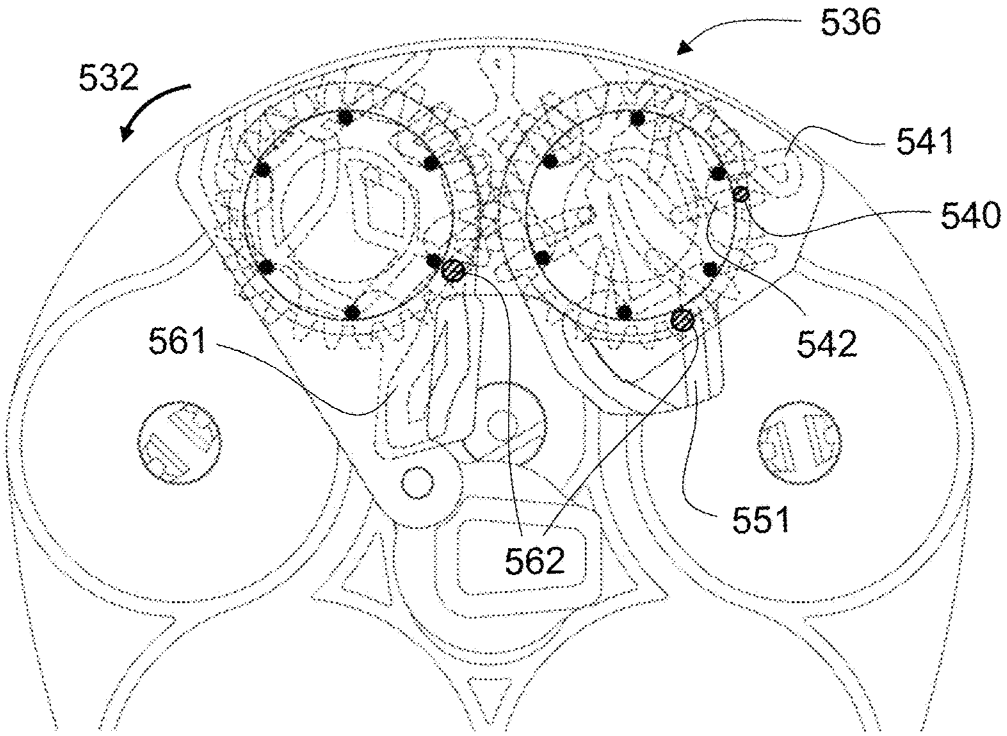
FIG. 51 shows a front view with the inhaler FIG. 47 in a second configuration.

FIG. 51 shows the cam plate 536 in position when the mouthpiece cover is in a fully open position. The peel-beak pins 562 are in the actuation positions 592 shown in FIG. 50, so the moving peel-beak components 590,590' are free to rotate as described above. The convoluted cam track 541 of the cam plate 536 is shown in broken lines, as are various features of the first and second indexers 512,514 obscured behind the cam plate 536. The driving pin 540 is positioned at the end of one of six slots 542 in the front face of the first indexer 512 so that movement of the cam plate 536 in the direction of arrow 532, during closing of the mouthpiece cover, will first move the driving pin 540 into the slot 542 and then advance the first indexer 512.

Figure 52:
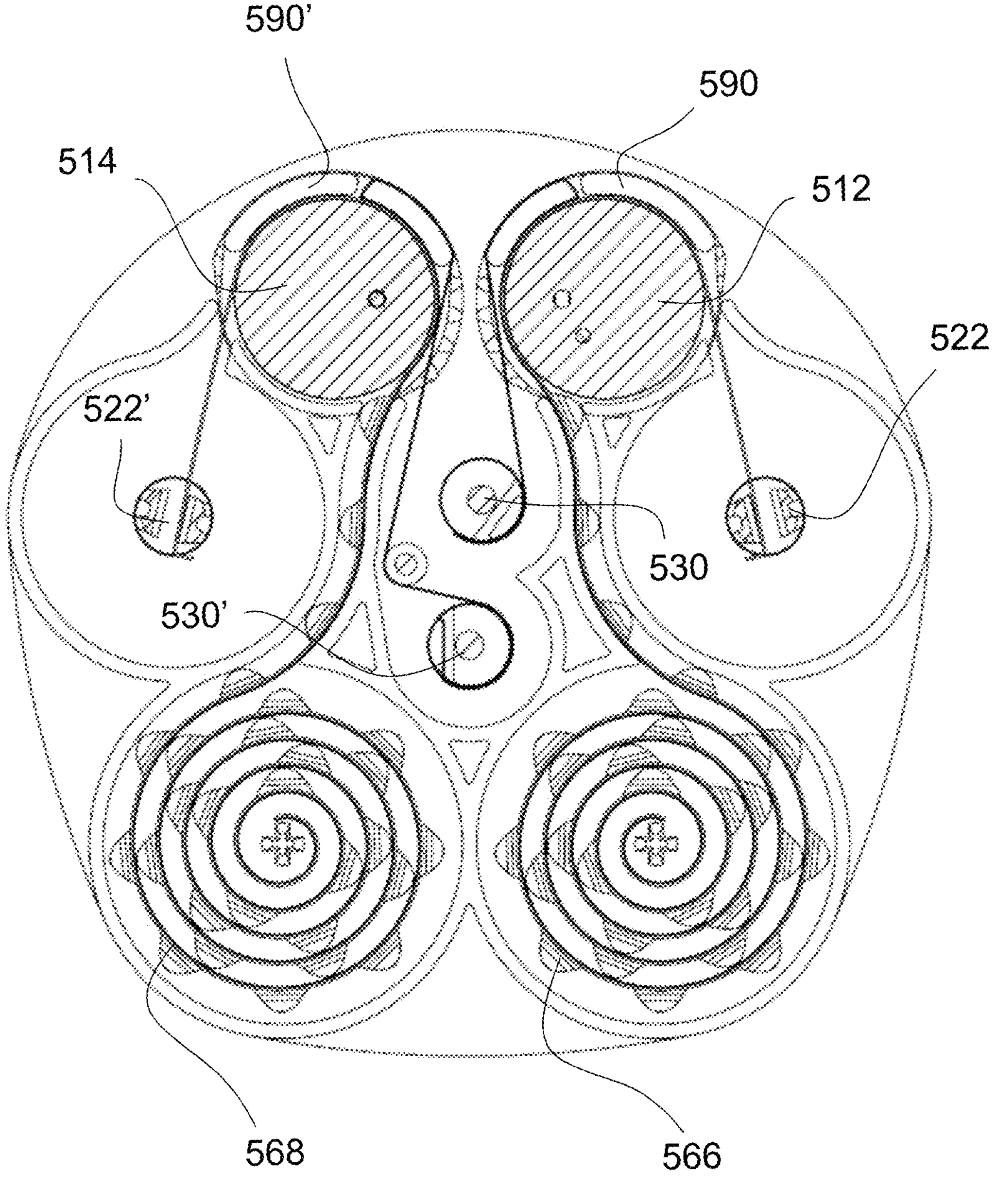
FIG. 52 shows the paths taken by a pair of blister strips through the inhaler of FIG. 47.

FIG. 52 shows the paths of the two blister strips 566,568 through the inhaler device. The first blister strip 566 runs around the first indexer 512, before the base used base sheet is taken up by the first spool wheel 522 and the used lidding sheet is taken up by the first take-up drum 530, having first passed around a peel-beak in the first moving peel-beak component 590. The second blister strip 568 takes a similar path around the second indexer 514, second spool wheel 524 and the second moving peel-beak component 590' and take-up drum 530'.

Figure 53:
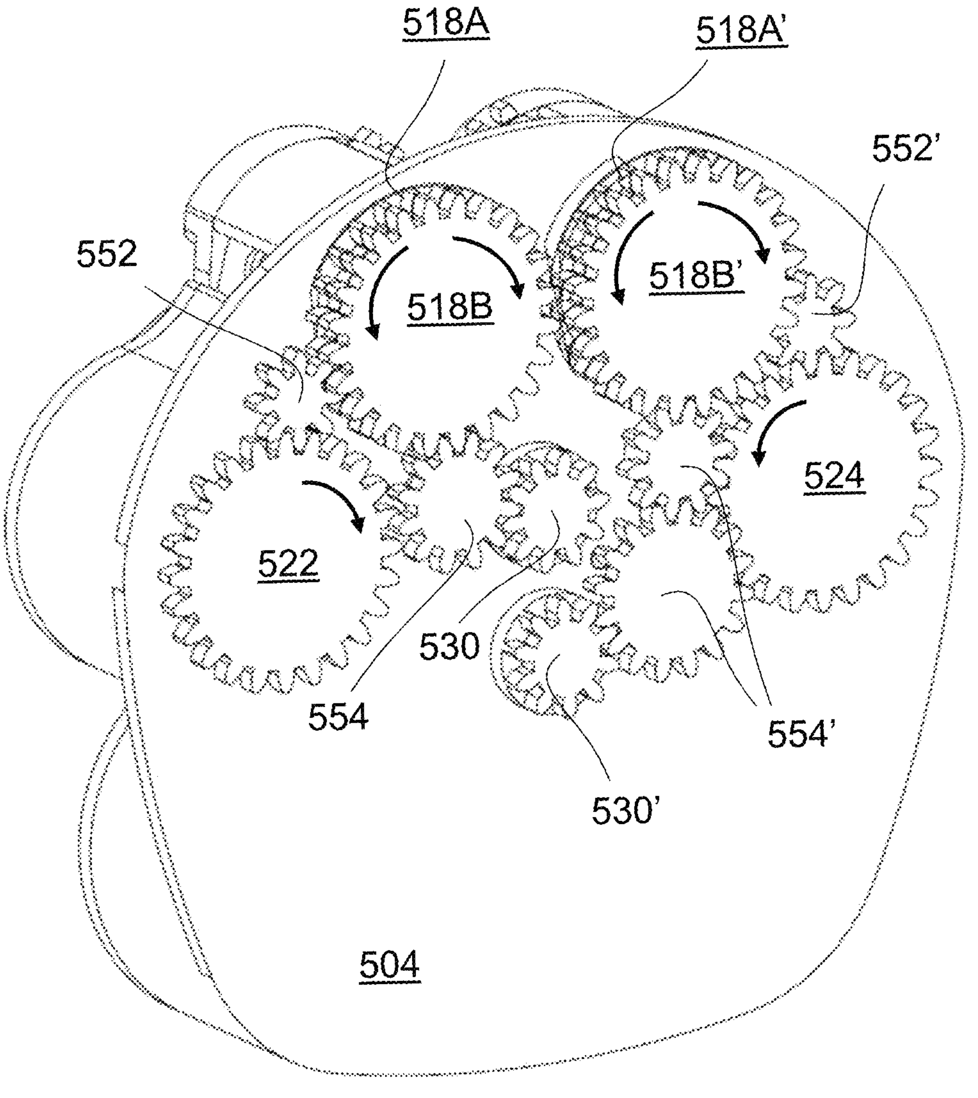
FIG. 53 shows the gearing at the rear of the inhaler of FIG. 47.

The gearing on the rear of the inhaler device is shown in FIG. 53. In a first drivetrain, the front gear 518A of the first indexer 512 drives the first spool wheel 522 via a first idler 552. Since the front gear 518A rotates with the first indexer 512, the first spool wheel 522 is driven as the first indexer is advanced by the cam plate 536. The first take-up drum 530 is driven, via a second idler 554, by the rear gear 518B of the first indexer 512. The torsion spring 556 between the front and rear gears 518A,518B accommodates changes of tension in the lidding sheet during operation, as described in previous embodiments, allowing movement of the peel fronts to control the peeling operation.

A second similar drivetrain is provided for the second indexer 514, although a pair of second idlers 554' are provided between the rear gear 518B' of the second indexer 514 and the second take-up drum 530'.

Figure 54:
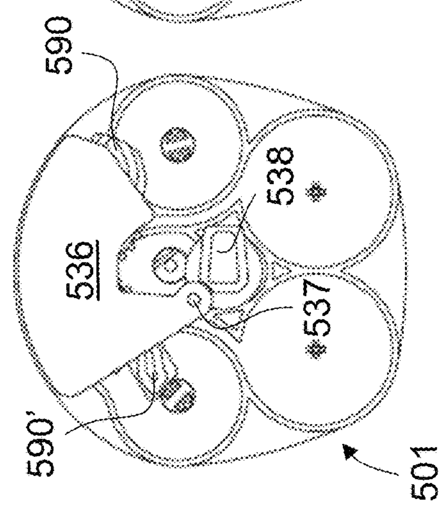
FIGS. 54 to 60 show the operation of the inhaler of FIG. 47.

Movement of the various components is illustrated in FIGS. 54 to 60. FIG. 54 shows the inhaler 501 immediately after a dose has been released. The cam plate 536 is connected to the hub component 538 by a pin 537 which is offset from the axis of rotation of the hub component 538. The mouthpiece cover (not shown) is fully open at this point, and the first and second peel-beak components 590,590' are in an outwardly rotated position. The remaining FIGS. 55 to 60 show movement of the cam plate 536 as the central hub component 538 rotates during opening 532 and closing 534 of the mouthpiece cover.

Figure 55:
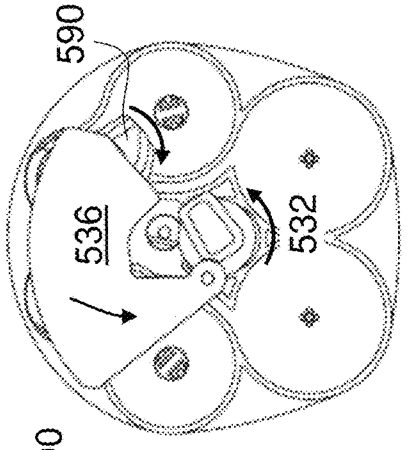
Figure 56:
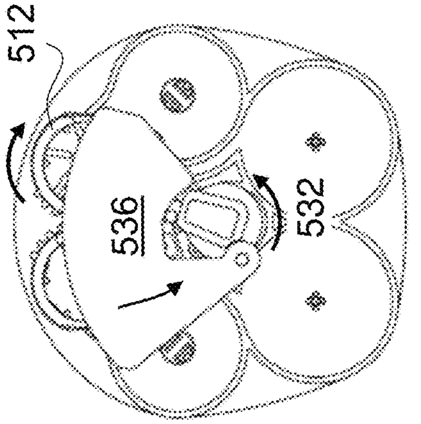
Figure 57:
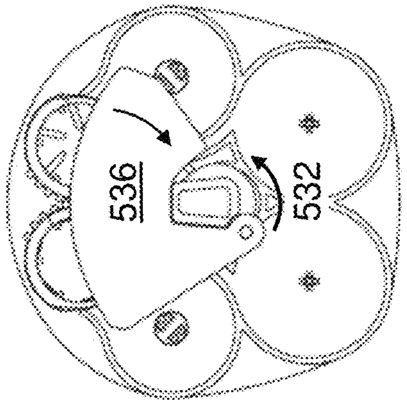

The initial stage of closing the mouthpiece cover, from FIGS. 54 to 55, starts to rotate the peel-beak components 590,590' inwards, and the rotation continues as the first indexer 512 is advanced from FIGS. 55 to 56. In the final part of closing, to the position shown in FIG. 57, tension generated in the lidding sheets by the charged torsion spring 556 biases the peel-beak components 590,590' to rotate outwards slightly, in the direction of arrows 593,594 in FIG. 50, as peel-beak pin 562 moves through lowest part of the cam track 561 in second peel-beak 590'.

Figure 58:
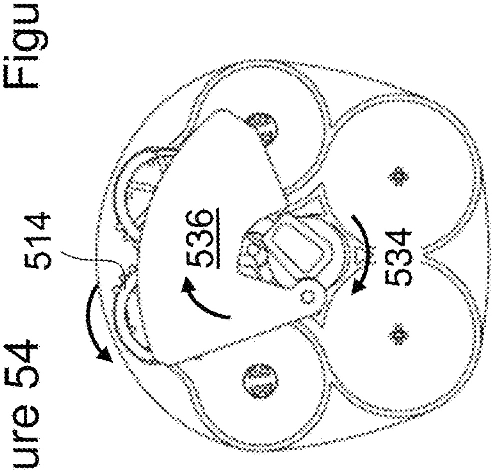
Figure 59:
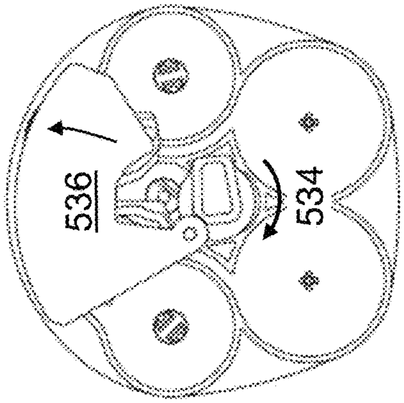
Figure 60:
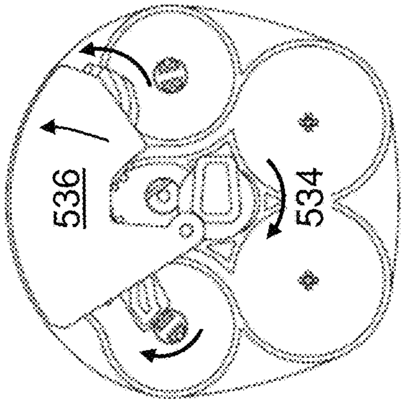

Subsequent opening of the mouthpiece cover, as shown in FIGS. 58 and 59, advances the second indexer 514 as the hub component 538 is rotated as indicated at 534. In the position shown in FIG. 59, both indexers 512,514 and both moving peel-beak components 590,590' are held in position by the cam plate 536. During the final opening movement, as shown in FIG. 60, the convoluted cam track 541 in the cam plate 536 continues to hold the indexers 512,514 stationary, while the peel-beak pins 562 move to the positions actuation positions 592 shown in FIG. 50, allowing outward rotation of the peel-beak components 590,590'.

It will be understood that the peel-beak components 590,590' move first after actuation of the inhaler device 501, so that the peel front is always ahead of the next dose to be peeled from the inhaler device. No peeling action is then performed until a set commitment point, when the peel-beak pins 562 are in the actuation positions 592 within the cam tracks 551,561 of the first and second peel-beak components 590,590'.

FIGS. 61-65 show an embodiment of the invention where the indexing and peeling operations are controlled by an intermittent ring-gear with a cam-track cut into it. The embodiment also features a split airway, half of which can reciprocate up and down (and also functions as a moving peel-beak) while the other half remains stationary. Torsion springs are provided between the take-up drum drive-gears and the take-up drums. Turning the intermittent ring-gear (via a cap-input-wheel with pawls that drive an input ratchet-wheel) rotates the first index wheel and thus indexes the first strip, while also translating the moving half of the airway/the moving peel-beak to maintain the position of the peel-front relative to the strip. This pulls the corresponding take-up drum round against its torsion spring to release lidding sheet, allowing the movement of the peel-front. Continuing to turn the intermittent ring-gear then turns the second index-wheel and the second take-up drum, peeling the second strip. The second take-up drum is geared to the first take-up drum, which further charges its torsion spring. The cam-track then releases the moving airway/peel-beak, which allows it to be pulled back down by the tension in the first lidding sheet effecting peeling of the first strip. Closing the cap again resets the ratcheted drive gear. The position of the pin on the moving airway/peel-beak prevents the intermittent ring-gear, and thus the input ratchet-wheel, from rotating backwards.

Figure 61:
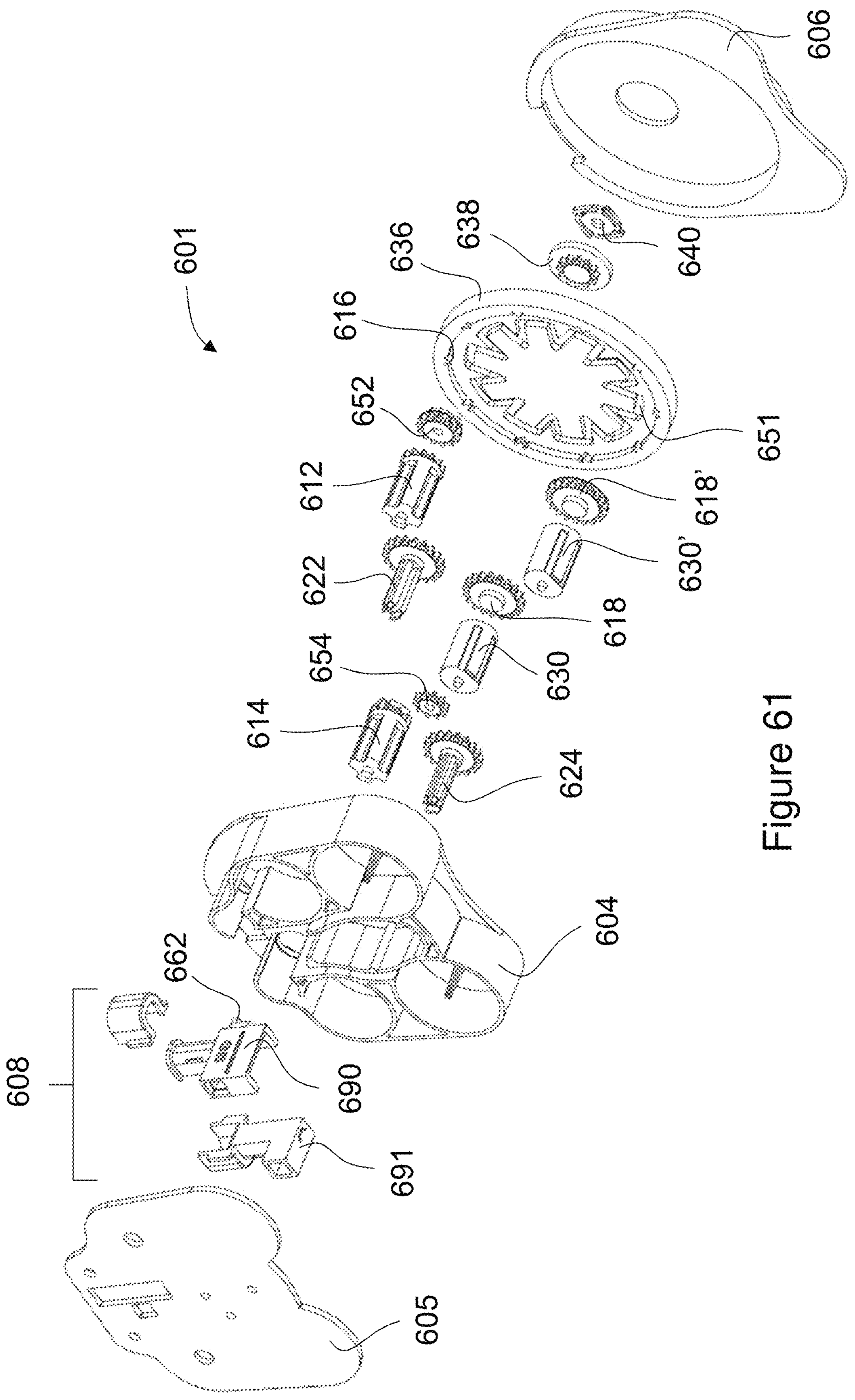
FIG. 61 shows an exploded view of an inhaler according to a sixth embodiment of the invention.

An exploded view of an inhaler 601 according to the sixth embodiment is shown in FIG. 61. A mid chassis 604, front plate 605 and rear chassis 606 are provided as part of the body of the inhaler 601. First and second index wheels 612,614 are provided to the rear of the mid chassis 604, and extend through the mid chassis 604 as indexers for first and second blister strips (not shown). First and second spool wheels 622,624, first and second take-up drums 630,630' and first and second idlers 652,654 are also provided. A drive gear 618,618' is provided for each of the first and second take-up drums 630,630', such that each drive gear 618,618' is rotatable relative to its respective take-up drum 630,630'. A torsion spring (not shown) is connected between each drive gear 618,618' and the respective take-up drum 630, 630'.

A mouthpiece and airway manifold 608 is provided in front of the mid chassis 604, and comprises a split airway with a first half 690 that can reciprocate vertically during use while a second half 691 remains stationary.

A ring gear/cam plate 636 is provided as a means to control/drive the movement of all components of the inhaler device 601, and can therefore be considered a central logic hub. Inwardly extending gear teeth 616 on a ring gear drive the indexers 612,614, spool wheels 622,624 and take-up drums 630,630'. A cam track 651 is also provided to engage a pin 662 on the first half 690 of the airway to control its vertical movement.

A unidirectional ratchet component 640 provides a connection to the mouthpiece cover (not shown) and fits within a cavity on the rear of a central input hub gear 638 to provide drive to the input hub gear 638 in only one direction. The hub gear 638 engages, in turn, with the rear of the ring gear/cam plate 636, so that movement of the mouthpiece cover is transmitted to the ring gear/cam plate 636.

Figure 62:
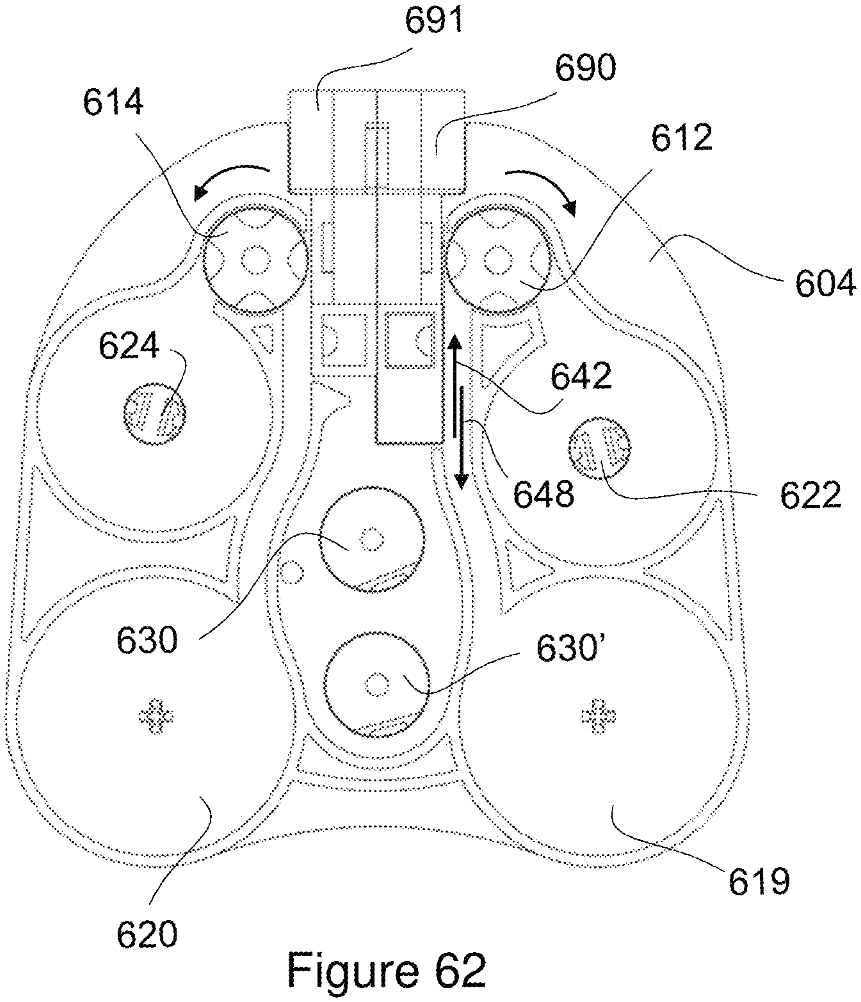
FIG. 62 shows a front view of the assembled inhaler of FIG. 61.

FIG. 62 shows a front view of the assembled components. First and second storage chambers 619,620 are provided at the lower end of the mid chassis 604 to contain first and second peelable blister strips of medicament (not shown). From a storage chamber 619,620 each blister strip is fed over an indexer 612,614 before the lidding sheet is passed through a half of the airway 690,691 to a take-up drum 630,630', and the base sheet is coiled round a spool wheel 622,624.

The vertical movement of the first half of the airway 690 is indicated by arrows 642 and 648. As will be described more fully with reference to later figures, the first and second indexers 612,614 are rotated sequentially in the directions indicated during use. As the first indexer 612 is advanced, the first half 690 of the split airway is moved upwards 642, moving the peel front in the same direction as the blister strip to delay the peeling operation. Subsequent downward movement 648 then serves to peel the lidding sheet from the base sheet to peel a dose of medicament. The linear movement of the first half 690 of the split airway therefore provides a moving peel beak component 690 to regulate the peeling operation as in other embodiments.

Figure 63:
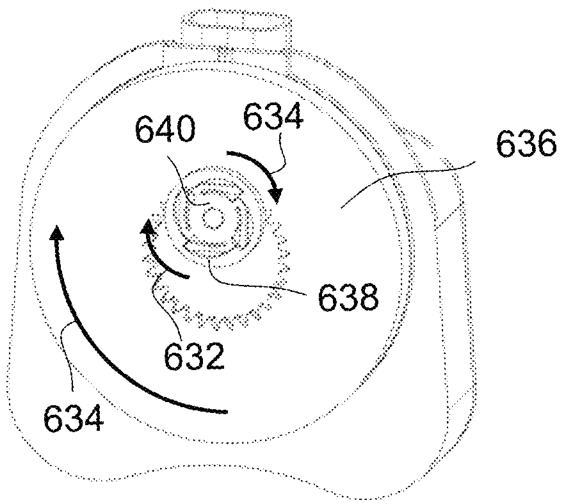
FIG. 63 shows a rear view of the inhaler of FIG. 62.

The rear view of FIG. 63 shows the interaction of the ratchet component 640, central input hub gear 638 and ring gear/cam plate 636. It should be clear that rotational drive in the direction of arrow 634, as would be caused by opening of a mouthpiece cover, will be transmitted to the ring gear/cam plate 636, but that drive in the opposite direction 632, caused when closing a mouthpiece cover, would not be transferred.

Figure 64:
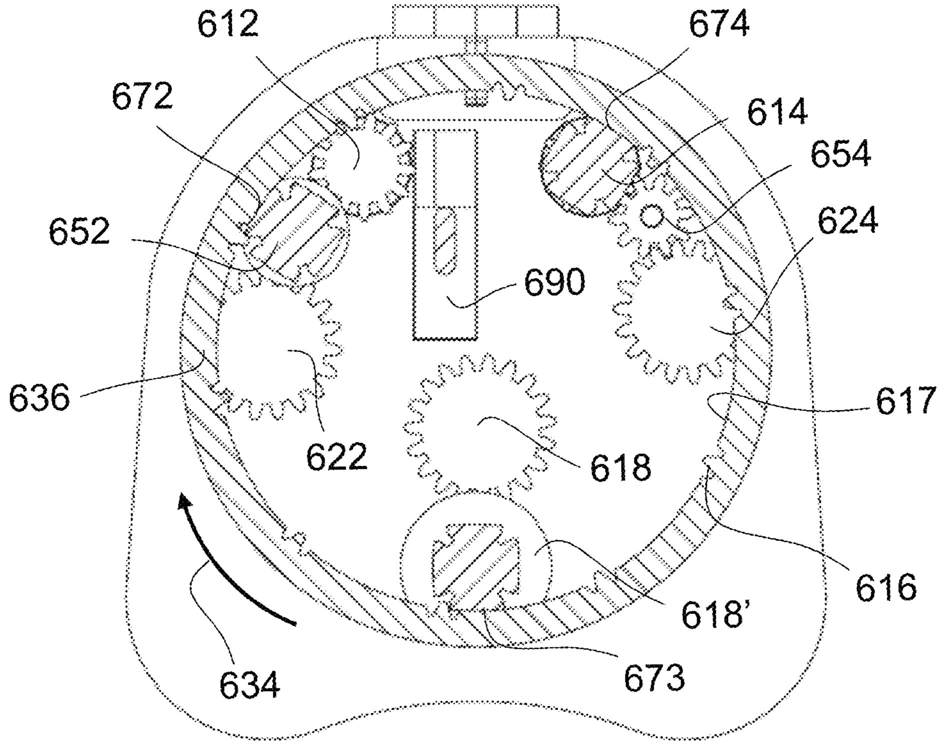
FIG. 64 shows a first rear cross section view of the inhaler of FIG. 62.

A first cross section of the inhaler device, looking from the rear side, is shown in FIG. 64. The cross section passes through the inwardly extending gear teeth 616 and through the components that these teeth 616 engage, namely the first idler 652, the drive gear 618' of the second take-up drum 630' and the second indexer 614. As shown in FIG. 64, a curved surface 672,673,674 of each of these components is engaged with a smooth sections 617 of the ring gear/cam plate 636 to provide a Geneva lock, holding each of the components against rotation. The first idler 652 is engaged with the first indexer 612 and first spool wheel 622, the second idler 654 is engaged between the second indexer and the second spool wheel 624, and the second take-up drum drive gear 618' is engaged with the first take-up drum drive gear 618. The Geneva lock described thus holds all these components against rotation as shown in FIG. 64.

Figure 65:
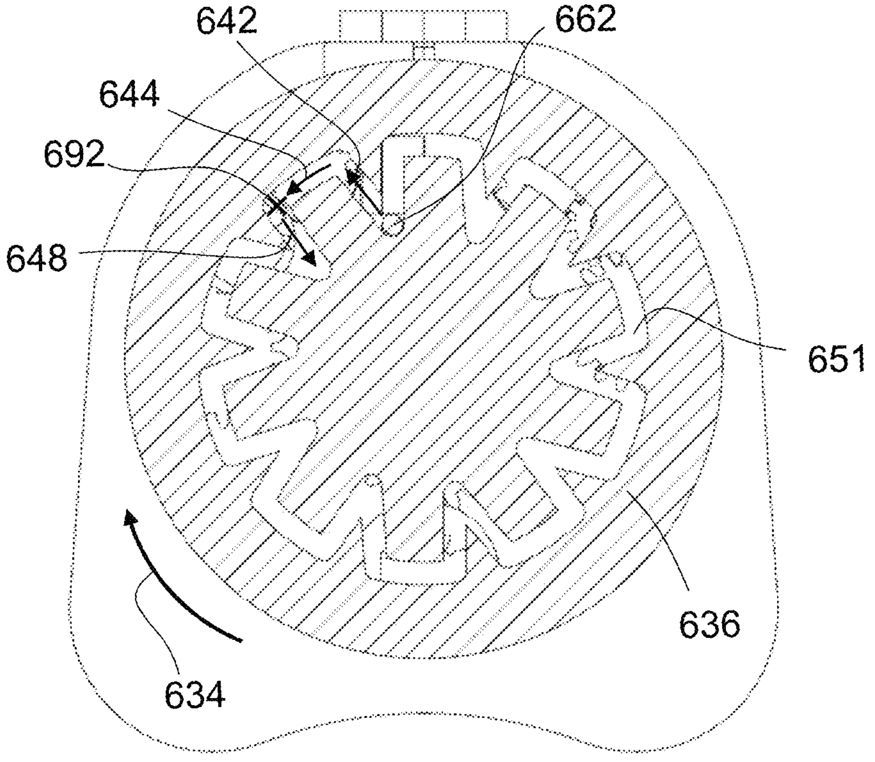
FIG. 65 shows a further rear view of the inhaler of FIG. 62.

FIG. 65 shows a further cross section, again from the rear of the inhaler device 601, taken through the cam track 651 in the ring gear/cam plate 636, and through the pin 662 of the first half 690 of the split airway.

The operation of the inhaler device will be described with reference to both FIG. 64 and FIG. 65.

As the ring gear/cam plate 636 is rotated in the direction of arrow 634, during opening of a mouthpiece cover, the inwardly extending teeth 616 first engage with the first idler 652 to drive the first indexer 612 and the first spool wheel 622 to rotate. The cam track 651 simultaneously guides the movement of the pin 662 in as shown by arrow 642, which causes a vertical upwards movement of the first half 690 of the split airway during rotation. The first indexer 512 therefore advances a dose, while the upwards movement of the split airway 690 adjusts the peel front location so that a dose is not peeled. This creates tension in the lidding sheet of a first blister strip, which in turn rotates the first take-up drum 630 relative to its drive gear 618, storing energy in the torsion spring provided therebetween as the necessary length of lidding strip is released.

When the first indexer 612 has been advanced by one step/dose, the curved surface 672 of the first idler 652 again engages with a smooth section 617 of the ring gear/cam plate 636 to hold the first indexer stationary as the rotation 634 of the ring gear/cam plate 636 continues. Further inwardly extending teeth 616 then engage first with the second indexer 514 and then with the drive gear 618' of the second take-up drum 630' to advance these components and to index and peel a second blister strip as the mouthpiece cover continues to open. During advancement of the second indexer 614 the split airway 690 is maintained in a raised position as the pin 662 moves through a section of the cam track 651 indicated by arrow 644. Gearing between the drive gear 618' of the second take-up drum 630' and the drive gear 618 of the first take-up drum 630 further charges the torsion spring of the first take-up drum 630.

When both indexers have been advanced by one step/dose, the curved surfaces 672,673,674 are again engaged with a smooth sections 617 of the ring gear/cam plate 636 so that both indexers 612,614 are held against rotation. The pin 662 is then at an actuation position or commitment point 692 in the cam track. At this point, the cam track 651 and actuation position 692 will be rotated to a position where movement of the pin 662 in the direction of arrow 648 provides the previously indicated downwards movement of the split airway 690. The torsion spring in the first take-up drum 630 pulls the first lidding sheet and split airway portion 690 downwards, peeling a dose from the first blister strip. Doses from both strips are thus exposed for inhalation once the cap is fully opened, but the second strip is only peeled after half of the opening operation has been completed, and the first strip is only peeled after a defined commitment point close to the end of the opening operation.

Subsequent closing of the mouthpiece cover provides no drive to the mechanism, because of the ratchet component 640. The engagement of the pin 662 with the cam track 651, and the Geneva locks previously described, help to ensure that there is no back rotation of any components so that the next actuation can be reliably performed.

A seventh embodiment of an inhaler 701 according to the present invention is illustrated in FIGS. 66 to 79. Briefly, the inhaler 701 of FIG. 66 separates the actions of index and peel, controlling the indexing and peeling using a geared system designed to function in the same manner as a Geneva mechanism, allowing first and second indexing systems to be advanced separately.

Figure 66:
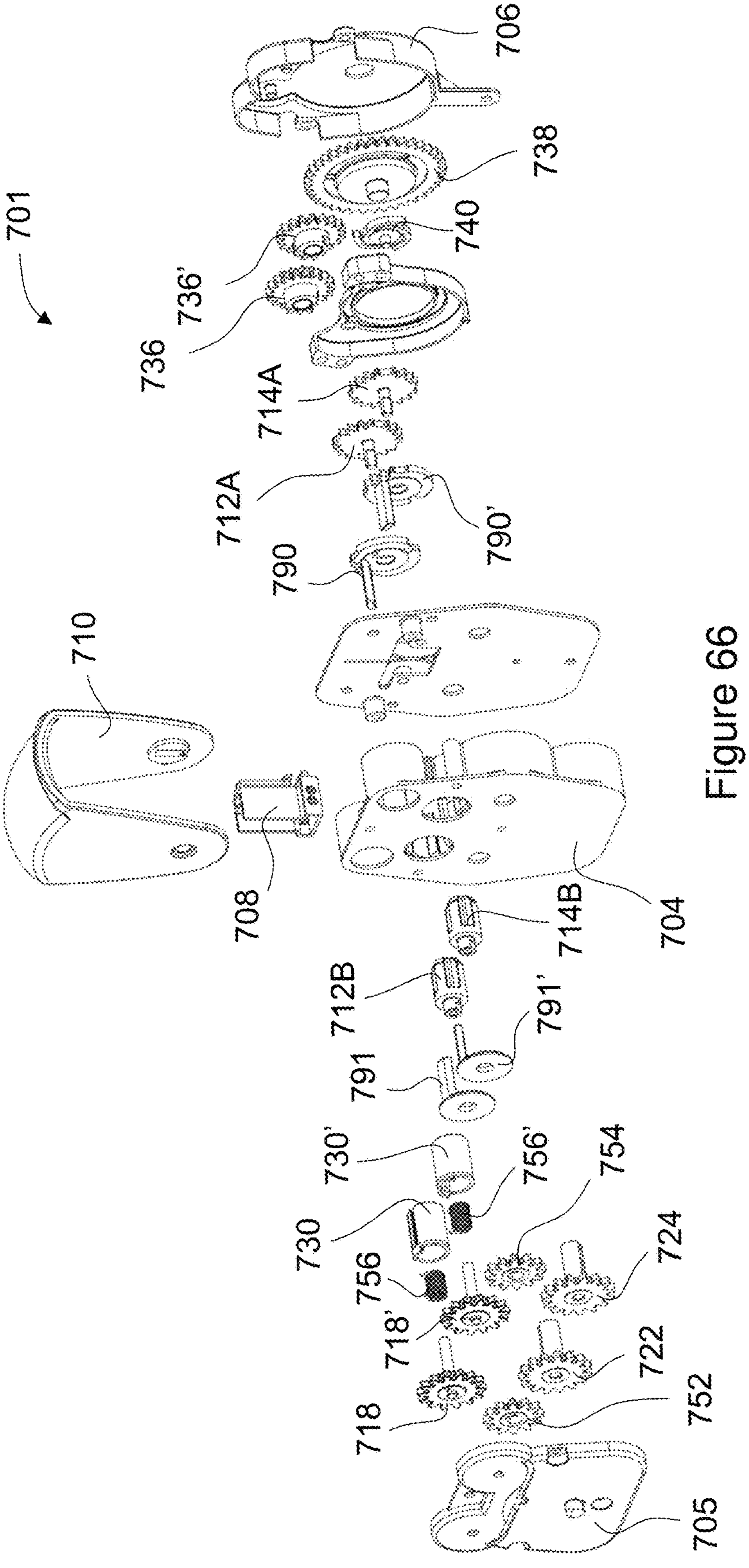
FIG. 66 shows an exploded view of an inhaler according to a seventh embodiment of the present invention.

As shown in the exploded view of FIG. 66, a mid chassis 704, front plate 705 and rear chassis 706 are provided as part of the body of the inhaler 701. The components to the rear of the mid chassis 704, including a moving airway 708 and moving peel beaks 790,790', form an indexing and peeling control mechanism with the movement of the airway 708 driven by the peel beak mechanism and therefore strictly linked to the peel function of the inhaler device 701. The components in front of the mid chassis 704 responsible for blister strip management.

The mechanism of the inhaler 701 is driven by movement of a mouthpiece cover 710 which is connected to a unidirectional ratchet component 740 located in a recess in the rear side of a hub gear 738. The hub gear 738 drives a first input gear 736 which, in turn, drives a second input gear 736'. The first and second input gears 736,736' respectively intermittently drive first and second indexers 712,714 and the first and second peel beak components 790,790'. Each of the first and second indexers 712,714 comprises an index gear 712A,714A and an index drum 7126,7146 assembled around a respective peel beak component 790,790'. The inhaler 701 also includes first and second slave beak components 791,791' which interact with the first and second peel beak components 790,790' as will be explained later.

The remaining components are largely similar to those described in previous embodiments. First and second spool wheels 722,724 are provided for the used base foils, and first and second take-up drums 730,730', each connected to a drive gear 718,718' via a torsion spring 756,756', are provided for the used lidding sheet/foils of a pair of blister strips.

Figure 67:
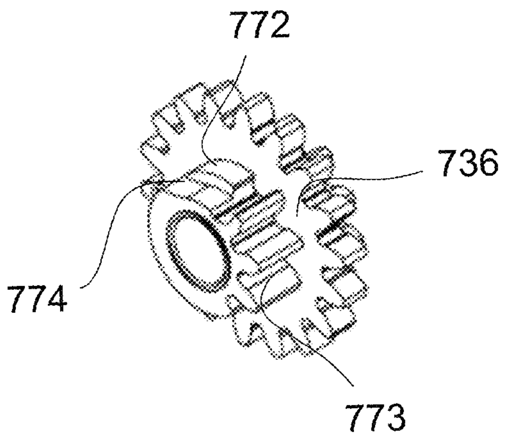
FIG. 67 shows a perspective view of an input gear from the inhaler of FIG. 66.
Figure 68:
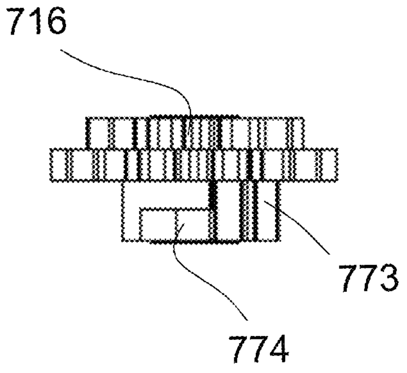
FIG. 68 shows a top view of the drive gear from FIG. 67.

FIG. 67 shows the first input gear 736 in greater detail. A boss 772 extends from a front surface of the input gear 736, and has a toothed section 773 extending the full height of the boss 772. Adjacent one end of the toothed section 773 is a cut-out 774 which extends only halfway down the boss 772 from its free end. A second ring of gear teeth 716 is provided to the rear of the first input gear 736, opposite the boss 772, to engage with the hub gear 738 in use. This can be seen in the top view of FIG. 68, where the cut-out 774 is again shown.

Figure 69:
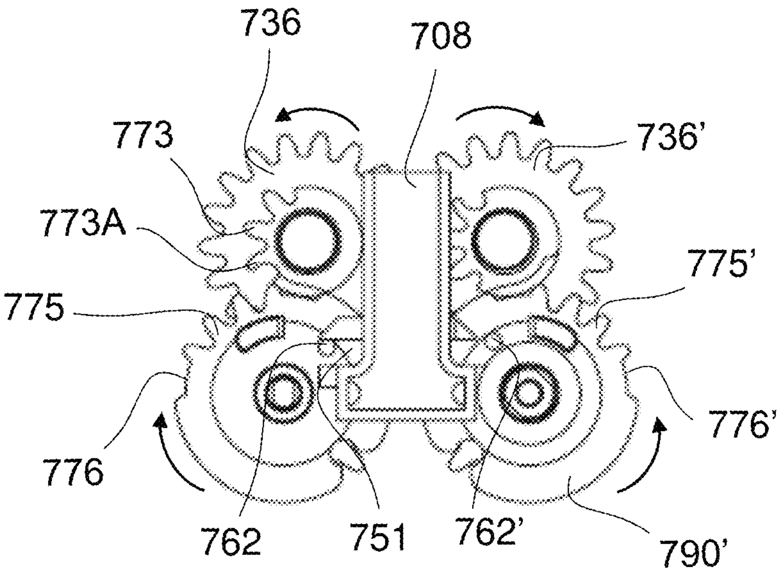
FIG. 69 shows a front view of part of the mechanism of the inhaler of FIG. 66.

FIG. 69 shows the part of the mechanism including the first and second input gears 736,736', the movable airway 708 and the first and second peel beak components 790,790'. The design of the second input gear 736' is similar to that of the first input gear 736, except that it lacks the second ring of gear teeth 716 so is driven solely by engagement with the first input gear 736. The second input gear 736' also has a slightly longer cut-out 774', although the width is still only half the height of the boss on the second input gear 736'.

The first and second peel beak components 790,790' both have toothed input sections 775,775' which engage with the toothed sections 773,773' of the first and second input gears 736,736' adjacent the end of the bosses 772,772'. Small recesses 776,776' are also provided in the outer edge of each peel beak component 790,790' on either side of the toothed input sections 775,775', and drive pins 762,762' for engagement with a slot 751 provided at the rear of the airway 708. Arrows show the rotation direction of the components during use, and it should be noted that the first tooth 773A in the toothed section on the first input gear 736 is sculpted to increase efficiency during initial engagement when the first input gear 736 initially starts to drive the first peel beak component 790. Although not labelled, similar sculpting is provided on a first tooth 773A' on the second input gear for the same reason.

Figure 70:
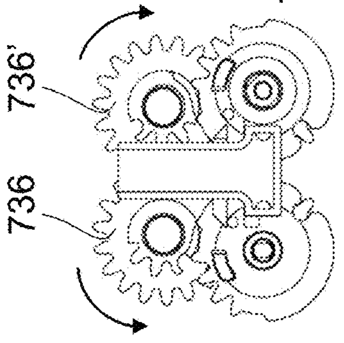
FIG. 70-75 show the movement of one part of the mechanism during opening of the mouthpiece cover.
Figure 71:
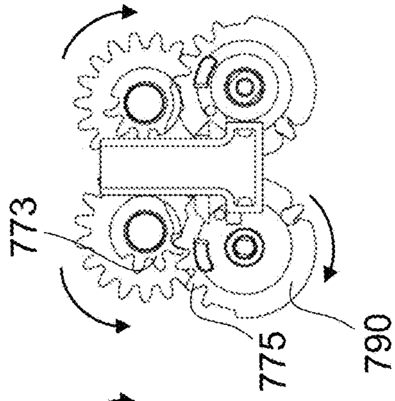
Figure 72:
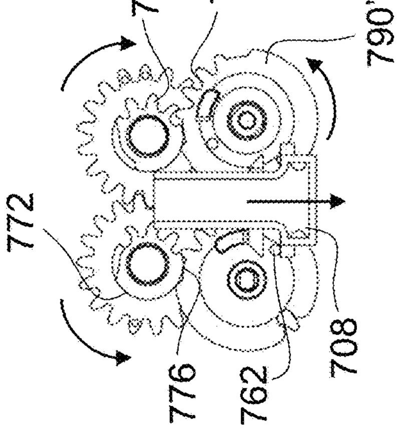

Advancement of the mechanism shown in FIG. 69 during use is illustrated in FIGS. 70-75. Opening of the mouthpiece cover 710 advances both the first and second input gears 736,736' simultaneously in opposite directions as shown in FIG. 70. This rotation initially brings the toothed section 773 of the first input gear 736 into engagement with the toothed input section 775 of the first peel beak component 790 to transmit rotation drive as shown in FIG. 71. The first peel beak component 790 is rotated until the corresponding toothed sections 773,775 come to an end, at which point the recess 776 engages with the outer surface of the boss 772 as shown in Figure. During this rotation the drive pin 762 on the drives down the airway 708 as indicated, to maintain the position of the peel-front relative to a blister strip.

Figure 73:
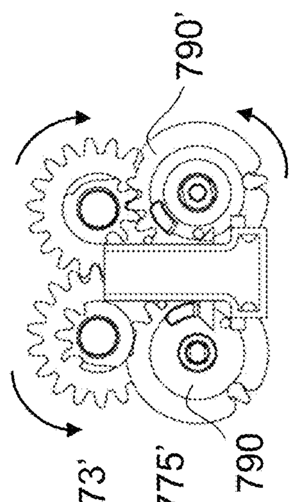

Once the first peel beak component 790 has been advanced as described above, continued movement of the mouthpiece cover 710 then engages the toothed section 773' of the second input gear 736' with the toothed input section 775' of the second peel beak component 790'. The second peel beak component 790' is thus advanced by the further opening movement, while the recess 776 provides a Geneva holding surface for engagement of the with the outer surface of the boss 772 and holds the first peel beak component 790 against further rotation as shown in FIG. 73.

Figure 74:
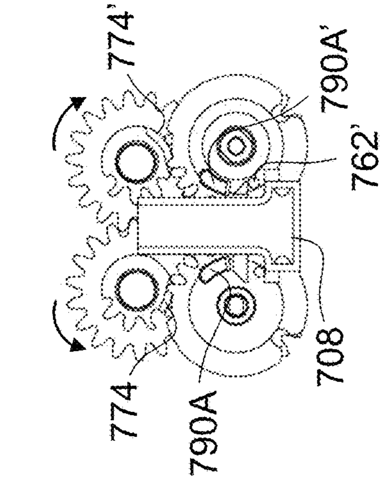
Figure 75:
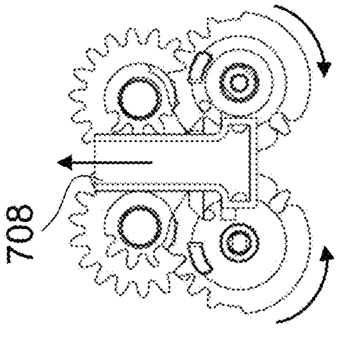

FIG. 74 shows the second peel beak component 790' is thus advanced to the end of the corresponding toothed sections 773',775'. The second drive pin 762' has engaged with the slot 751 of the airway 708 so that both peel beak components 790,790' are linked via the movable mouthpiece 708. Further rotation from the position shown in FIG. 74, which can be considered a commitment point for the mechanism, moves the cut-outs 774,774' of the first and second input gears 736,736' into a position above the first and second peel beak components 790,790'. The cut-outs 774, 774' then provide space for the outer periphery of each peel beak component 790,790' to rotate past the boss 772,772' of its respective input gear 736,736'. As will be explained later, advancing the mechanism also generates a spring biasing through a blister strip, and this drives the first and second peel beak components 790,790' to rotate back to their initial positions. The airway 708 is also moved vertically upwards as shown in FIG. 75. This release performs the peeling operation to open a dose of medicament from each of a pair of blister strips.

FIG. 74 also shows the peel beaks 790A,790A' of the first and second peel beak components 790,790' adjacent the drive pins 762,762'. The first and second slave beak components 791,791' (not shown) have been driven by the peel beaks 790A,790A' during rotation and now lie above the drive pins 762,762'. This allows a larger physical pee front to be provided without interfering with the drive pins 762,762' or the rear of the mouthpiece 708 providing the slot 751.

As described above in relation to FIG. 66, the first index gear 712A and first index hub 712B are assembled around the first peel beak component 790, and the second index gear 712A and index hub 714B are assembled around the first peel beak component 790. Accordingly, the first and second index gears 712A,714A sit behind the first and second peel beak components 790,790' in the assembly shown in FIGS. 69-75.

Figure 76:
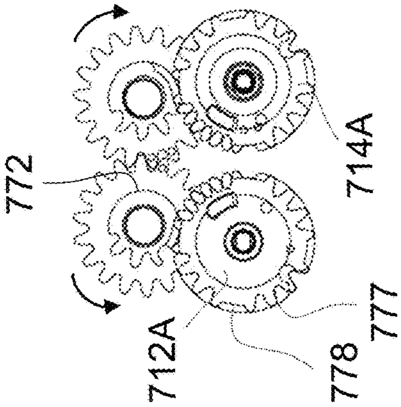
FIG. 76-77 show movement of a further part of the mechanism during opening of the mouthpiece cover.
Figure 77:
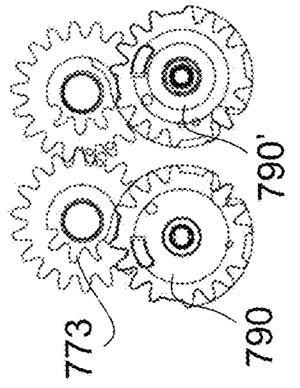

FIGS. 76 and 77 correspond to the mechanism position shown in FIGS. 74 and 75 respectively, and show the first and second index gears 712A,714A in broken lines. Both index gears 712A,714A have a similar form, which will be described only once with reference to the first index gear 712A. Four toothed drive sections 777 are provided around the periphery of the first index gear 712A, each similar to the toothed input section 775 of the first peel beak component 790. Between the toothed drive sections 777 are provided locking recesses 778 similar to the recesses 776 of the first peel beak component 790.

The first and second index gears 712A,714A are initially advanced by the first and second input gears 736,736' along with the first and second peel beak components 790,790' as described in relation to FIGS. 70 to 73. However, because they sit behind the first and second peel beak components 790,790', their peripheries engage with a lower part of each boss 772,772' below the cut-out 774,774'. As such, the bosses 722,722' remain engaged with recesses 778,778' of the first and second index gears 712A,714A to hold them against rotation toward the end of mouthpiece opening. In other words, once a dose is indexed, the first and second indexers 712,714 are held stationary while the peeling operation is conducted.

The mechanism as described provides an oscillating or reciprocating movement of the first and second peel beak components 790,790' and an intermittent rotation of the first and second indexers 712,714 from a common drive. The movement of the components, and of the moving airway 708, can be reliably synchronised. The first and second indexers 712,714 are advanced a quarter of a turn at a time to correspond to the four provided dose pockets for receiving drug pockets of a pair of blister strips.

A similar functionality could be achieved using a pin Geneva mechanism, with both halves of the overall mechanism having a single pin driving a stack of two Geneva wheels with a release area for one of the layers (the peel beak layer) enabling the back-driving of the beaks. However, using a gear drive as described provides a less variable force-profile, and avoids the need for an unsupported pin which may be weak and vulnerable to snapping.

The mechanism indexes a first side and drives the airway 708 down with the peel front, then indexes the second side moving that peel front to an opening of the mouthpiece 708 before both are released. As the peel beak components 790,790' rotate back to their original position they are linked via the airway 708, which ensures simultaneous movement and drives the airway 708 into position in line with a revealed drug pocket of each blister strip.

Figure 78:
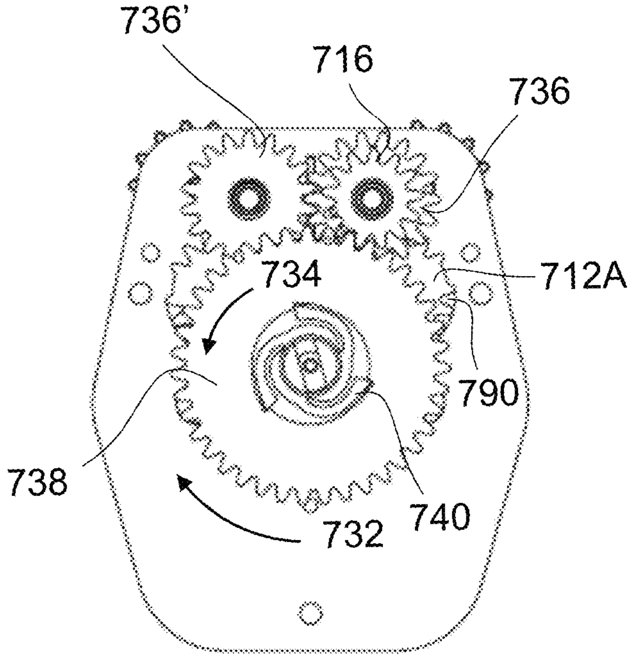
FIG. 78 shows the drive mechanism of the inhaler of FIG. 66.

The input drive to the mechanism is illustrated in the rear view FIG. 78. The ratchet component 740 is shown received in a central recess in the hub gear 738 and is arranged to provide drive to the hub gear 738 during rotation 734 caused by opening of the mouthpiece cover (not shown) but not during closing 732. The hub gear 738 is shown engaged with the second ring of gear teeth 716 on the first input gear 736, and the first index gear 712A is labelled, along with the first peel beak component 790, which is largely obscured by the first index gear 712A from the rear. Since, as already described, the entire indexing and peeling operation is completed during opening of the mouthpiece cover 710, the motion during closing 732 of the mouthpiece cover 710 does not need to be transmitted to the mechanism of the inhaler 701. A non-return ratchet interacts with the gear-train to ensure the drive gearing is not driven backwards when the ratchet component 740 is rotated within the hub gear 738 during closing of the mouthpiece.

Figure 79:
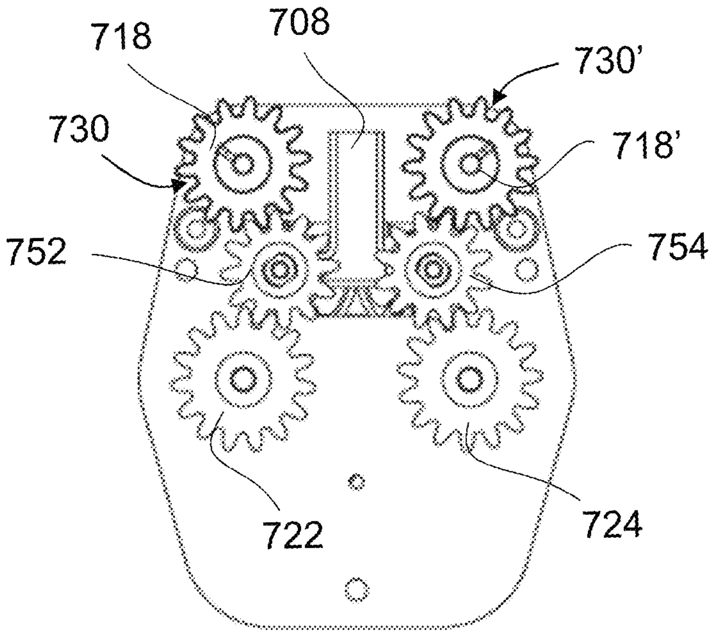
FIG. 79 shows the strip management mechanism of the inhaler of FIG. 66.

FIG. 79 shows the components of the inhaler 701 concerned with strip management. The view in FIG. 79 is a front view, from the opposite side of the mid chassis 704 from FIG. 78. First and second output gears 752,754 are connected to the first and second index hubs 7126,7146 to transfer rotational drive from the first and second indexers 712,714 to first and second spool wheels 722,724 and to the drive gears 718,718' of first and second take-up drums 730,730'.

As in other embodiments the first and second spool wheels 722,724 simply receive and wind in the used base sheets/foils of first and second blister strips, while the first and second take-up drums 730,730' receive the used lidding foils/sheets. The torsion springs 756,756' provided between the drive gears 718,718' and the take-up drums 730,730' act in the same way as in earlier embodiments, to initially allow movement of a lidding foil with an indexer 712,714 and peel beak component 790,790' while storing spring energy to subsequently drive the peeling operation, and to compensate for the increasing diameter of used lidding foil/sheets as the blister strips are used. The first and second take-up drums 730,730' are geared to rotate in the opposite direction to their corresponding indexers 712,714, which further charges the torsion springs 756,756' during indexing. This provides sufficient tension to move the lidding sheet/foils back past their peel-front and open the next dose on the strip when the peel beak components 790,790' are released.

The inhaler 701 according to the seventh embodiment creates design freedom in terms of layout, timings, sequences, forces, torques, displacements, etc. The moving airway does not move on the same path (or offset from) as the blister-strips during use, because its movement is linear rather than rotational. This means that there is less chance of lidding foil being pinched between the moving airway 708 and the first and/or second index wheels 712,714, because they are only close to each other at the end of their travel during a peeling operation.

Unlike in the inhaler 601 of the sixth embodiment, there is just a single moving airway 708, rather than separate moving and sections, which would necessitate a clearance gap between the two sections. A simpler piston-type seal can therefore be used between the airway 708 and a mouthpiece of the inhaler 701.

An eighth embodiment of the invention will now be described with reference to FIGS. 80 to 89. Again, the inhaler 801 of the eighth embodiment provides design freedom in terms of layout, timings, sequences, forces, torques, displacements, etc, and works by using a mouthpiece cover to turn a hub gear, via ratchet drive, against a spring (extension or torsion) to complete the indexing operation. A feature on the chassis releases the ratchet from the hub gear, and the spring returns it to its starting position. In this way, a one-way 120° movement of the mouthpiece-cover is translated into a reciprocating motion of the mechanism input.

Figure 80:
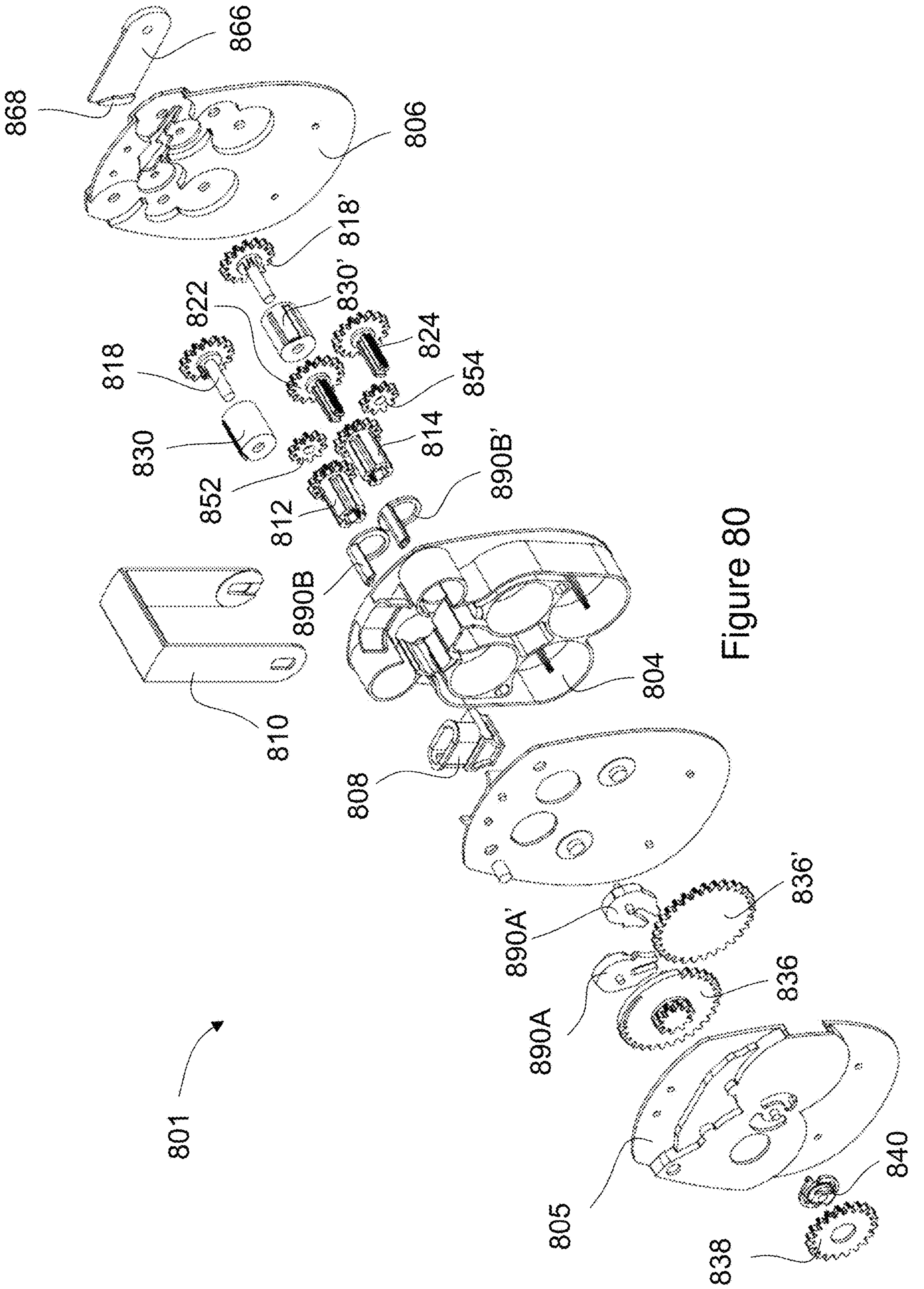
FIG. 80 shows an exploded view of an inhaler according to an eighth embodiment of the present invention.

The exploded view of FIG. 80 shows the components of the inhaler 801. Many of the components are similar to those described in previous embodiments, including the first and second spool wheels 822,824, first and second indexers 812,814, and first and second take-up hubs 830,830' with their respective drive gears 818,818'. First and second idler gears 852,854 are provided to link some of these components into a gear mechanism for strip management. Although not shown in FIG. 80, torsion springs are provided between each of the first and second take-up hubs 830,830' and its respective drive gear 818,818' to provide sprung hubs as described previously.

The mechanism of the inhaler 801 is driven via the mouthpiece cover 810, which is directly coupled to a ratchet component 840 within a hub gear 838. The hub gear 838 permanently engages with and drives a first input gear 836, which extends through a front plate 805. The first input gear 836 engages with and drives a second input gear 836'.

The first and second input gears 836,836' drive first and second peel beak components 890,890'. The peel beak components 890,890' of the mechanism are formed in two parts, so that the first peel beak component 890 comprises a front part 890A and a rear part 890B assembled from opposite sides of a mid chassis 804. Similarly, the second peel beak component 890' comprises a front part 890A' and a rear part 890B' assembled from opposite sides of a mid chassis 804. A locking arm 866 with a projection 868 is also provided behind the rear plate of the inhaler 801.

Figure 81:
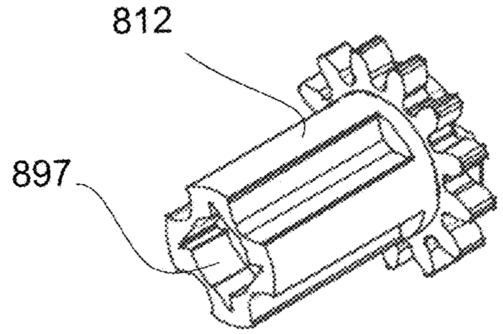
FIG. 81 shows a perspective view of an indexer from the inhaler of FIG. 80.
Figure 82:
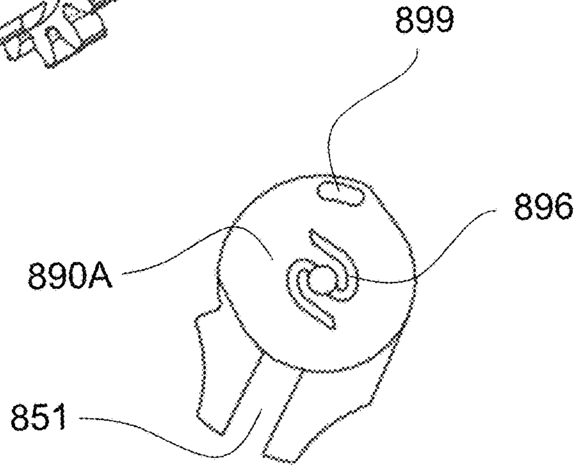
FIG. 82. shows a perspective view of a first part of a peel beak from the inhaler of FIG. 80.
Figure 83:
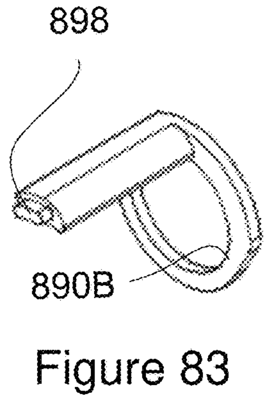
FIG. 83. shows a perspective view of a second part of a peel beak from the inhaler of FIG. 80.

Detail views of the first indexer 812 and front and rear parts 890A,890B of the first peel beak 890 are shown in FIGS. 81-83. A recess 897 is provided in one end of the first indexer 812, shown in FIG. 81, to receive ratchet teeth 896 provided on a face of the front part 890A of the first peel beak component as shown in FIG. 82. The front part 890A of the first peel beak component also provides a drive slot 851 and a recess 899 for receiving a tab 898 provided on the rear part 890B of the peel beak component shown in FIG. 83 during assembly. The second indexer 814 and front and rear parts 890A',890B' of the second peel beak component 890' comprise equivalent features.

Figure 84:
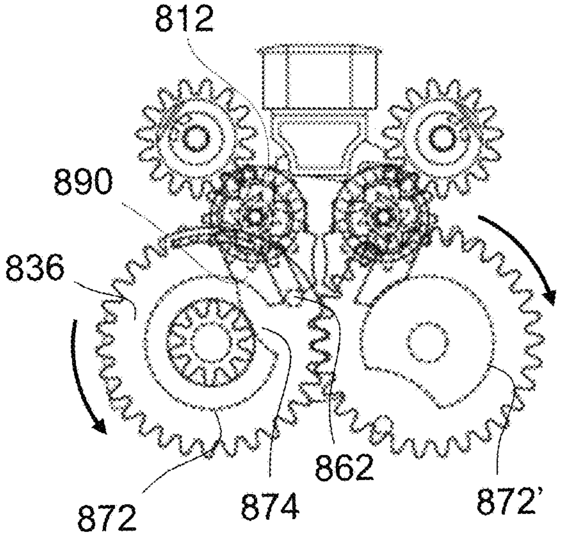
FIG. 84-85 show operation of a locking mechanism of the inhaler of FIG. 80.
Figure 85:
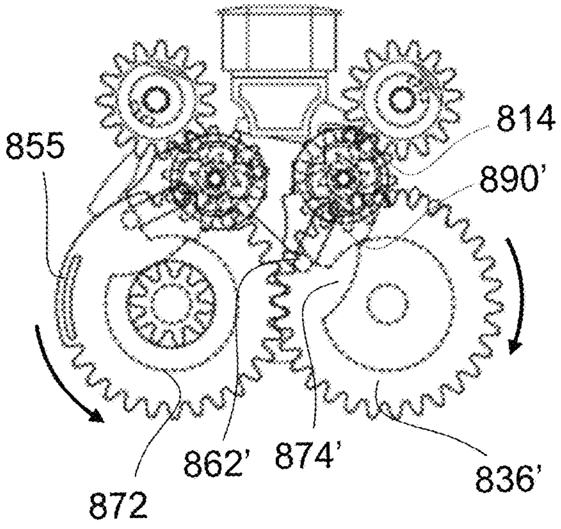
Figure 86:
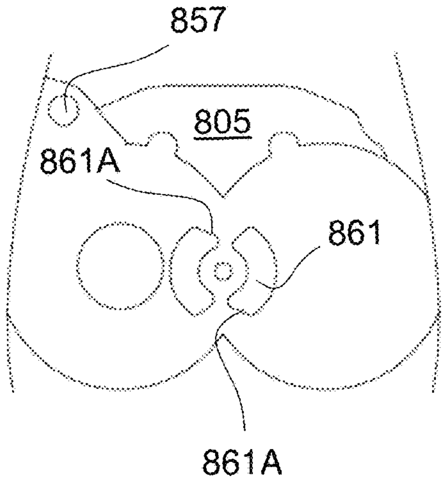
FIG. 86 shows a front view of the front plate from the inhaler of FIG. 80.

Advancement of the mechanism during mouthpiece opening is illustrated in the front view of FIGS. 84 and 85. The rotation direction of the first and second input gears 836,836' is indicated.

FIG. 84 shows the initial stages of opening a mouthpiece cover, with a drive pin 862 provided on the rear surface of the first input gear 836 engaging the drive slot 851 of the first peel beak component 890. The first peel beak component 890 is initially prevented from rotating by a Geneva style locking between the first peel beak component 890 and a boss 872 on the rear of the first input gear 836, before being allowed to rotate by a cut-out 874 on one side of the boss 872 to the position shown in FIG. 85. The ratchet teeth 896 of the first peel beak component 890 engage with the recess 897 of the first indexer so that the first indexer is driven along with the first peel beak to advance a first blister strip. During the described movement of first peel beak component 890, the second peel beak component 890' is held stationary by engagement with an outer surface of a boss 872' provided on the rear of the second input gear 836'.

Once rotation of the first peel beak component 890 is complete, as shown in FIG. 85, it is again held in position by engagement with the outer surface of the boss 872. A drive pin 862' on the rear surface of the second input gear 836' then engages with a drive slot 851' to drive the second peel beak component 890' to rotate in a similar manner via a cut-out 874' in the boss 872' of the second input gear. The second indexer 814 is driven during this movement as described above for the first indexer 812 to advance the second blister strip. The staggered positions of the drive pins 862,862' and cut-outs 874,874' ensure that the two strips are indexed sequentially rather than concurrently.

FIG. 85 also shows a slot 855 in one side of the first input gear 836 for attaching one end of a tension spring (not shown). The other end of the tension spring is connected to a mounting point 857 on the front plate 805 shown in FIG.

Figure 87:
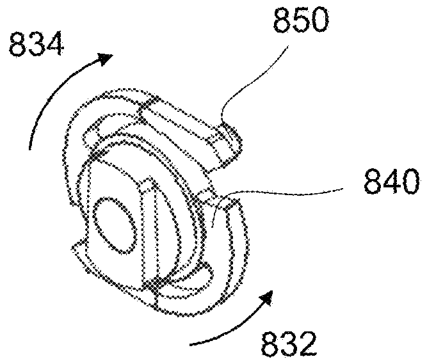
FIG. 87 shows a perspective view of an input ratchet from the inhaler of FIG. 80.

86. The front plate 805 also comprises es a pair of cam slots 861 which receive projections 850 provided on the arms of the ratchet component 840 as illustrated in FIG. 87. One end 861A of each cam slot is angled so that the projections 850 are biased inwards toward the end of rotation 834 of the ratchet component 840 during cap opening. This allows the hub gear 838 to rotate past the ratchet component 840 and re-set to its original position, driven by the tension spring and other spring forces within the system, for example from the sprung take-up drums 830,830'. The first and second peel beak components 890,890' also rotate back to their initial positions during this re-set operation, but the ratchet teeth 896 and recesses 897 ensures that this reverse drive is not transmitted to the first and second indexers 812,814. A peeling operation is therefore achieved once a commitment point (corresponding to the angled ends 861A of the cam slots 861) is reached during opening of the mouthpiece. It will be understood that the ratchet component 840 does not transmit drive during rotation 832 when closing the mouthpiece cover 810.

Figure 88:
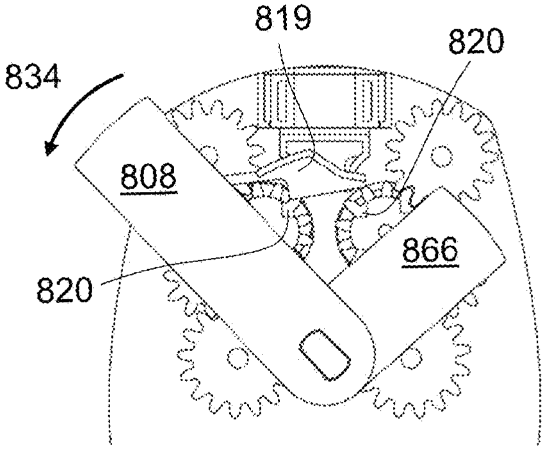
FIG. 88-89 show opening of the mouthpiece of the inhaler of FIG. 80.
Figure 89:
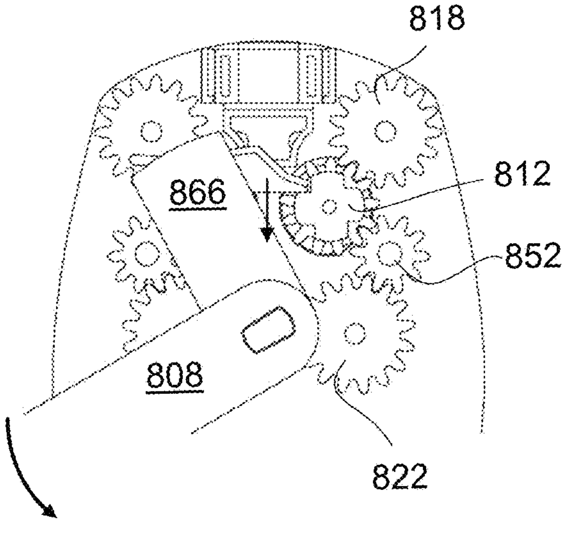

FIGS. 88 and 89 illustrate a locking mechanism to ensure that the first and second indexers 812,814 remain in their advanced positions during the peeling operation. The locking mechanism is shown from the rear of the inhaler 801, with the majority of the rear plate 806 omitted for clarity. A locking arm 866 is connected to the mouthpiece cover 808 to rotate with the mouthpiece cover. As the mouthpiece cover is rotated 834 to the open position, the locking arm is also rotated. Towards the end of this opening movement, a protrusion 886 (see FIG. 80) on the locking arm 866 engages with a latch component 819 to drive it down into locking recesses 820,820' provided at the rear end of the first and second indexers 812,814, as shown in FIG. 89. The first and second indexers 812,814 are released again when the mouthpiece cover is closed.

The engagement of the first indexer 812 with the drive gear 818 for the first take-up drum 830 and, via the first idler 852, the first spool wheel 822 is also shown in FIG. 89. The second side of the mechanism similarly arranged and driven via the second indexer 814. As in other embodiments, the sprung first and second take-up drums 830,830' are driven in the opposite direction to their respective drive gear 818,818' by the lidding-foil during indexing.

Another inhaler 901, according ninth embodiment of the invention, is illustrated in FIGS. 90 to 96. The inhaler 901 uses a mouthpiece cover to turn a hub gear via ratchet component, which translates the reciprocating motion of the cover into single directional drive of the input drive mechanism. The drive of the hub gear results in the intermittent sequential non-concurrent motion of two indexers and therefore two blister strips through a geared Geneva style mechanism, which drives and positions the index wheels. Peel beaks are integrated single linear moving airway, are controlled using a split desmodromic cam, which is synchronised with the motion of the first strip to prevent peeling. This results in overlaying of the lid foil of the second strip.

Figure 90:
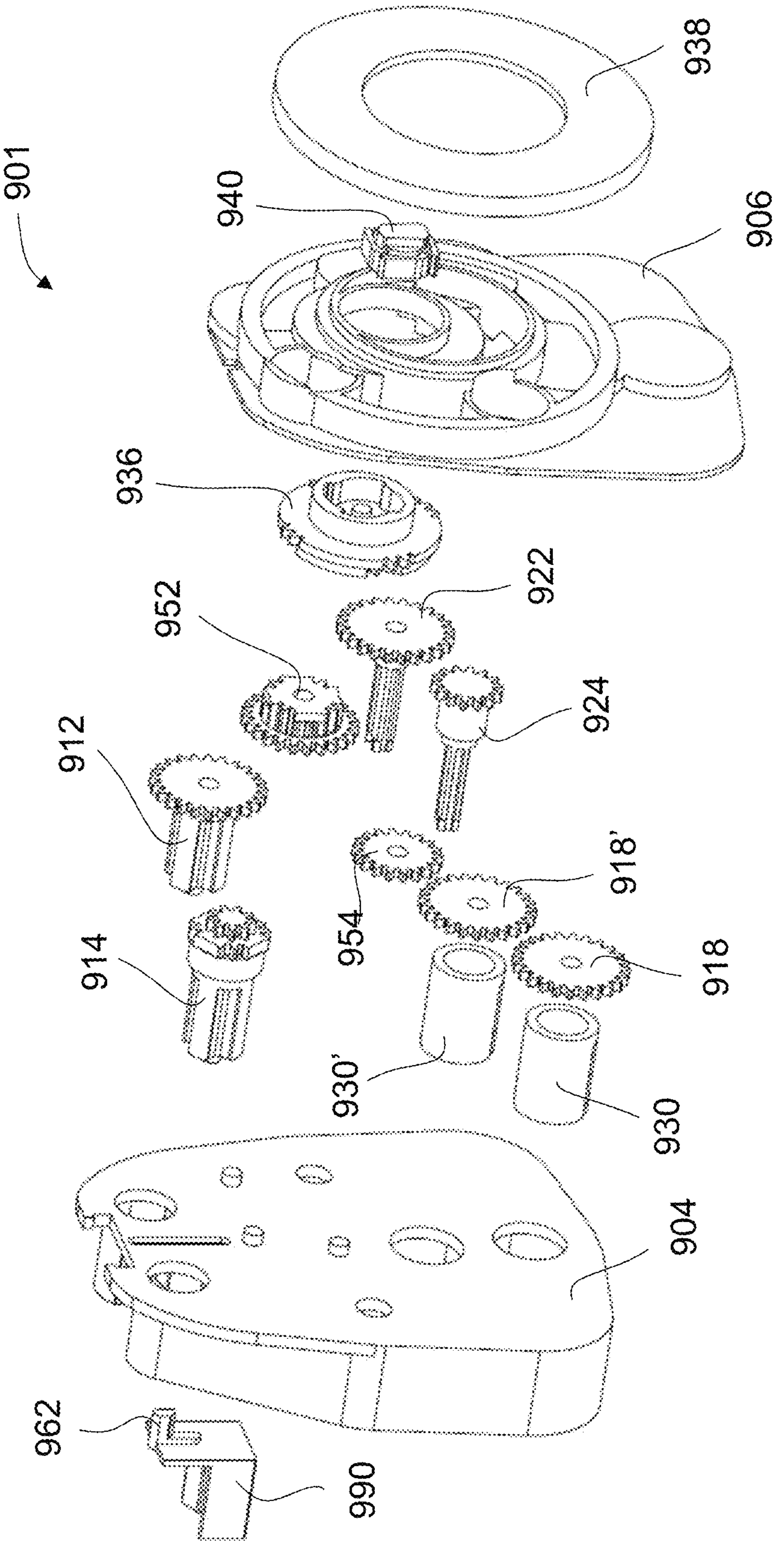
FIG. 90 shows a rear exploded view of an inhaler according to a ninth embodiment of the present invention.

FIG. 90 shows a rear exploded view of the inhaler 901 of the ninth embodiment with some components omitted. A ratchet component 940 is provided to transmit drive from a mouthpiece cover (not shown) to a hub gear 936 through a rear plate 906 of the inhaler body. A ring gear 938 is also provided to the rear of the rear plate 906.

First and second indexers 912,914, spool wheels 922,924 and idler gears 952,954 are located between the rear plate 606 and a mid chassis 904, along with first and second take up drums 930,930' (with associated input gears 918,918'). As in other embodiments, torsion springs (not shown) are provided to create sprung take up drums 930,930' providing the benefits previously described. A moving peel beak component 990 is illustrated in front of the mid chassis 904, and comprises a drive pin 962 which extends through a slot in the mid chassis to constrain the peel beak component 990 to linear motion.

Figure 91:
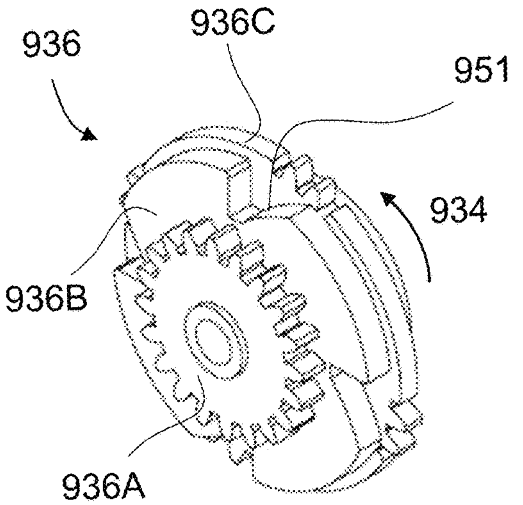
FIG. 91 shows a perspective view of a hub gear from the inhaler of FIG. 90.

A front perspective view of the hub gear 936 is shown in FIG. 91. The hub gear 936 comprises a front drive gear 936A, a central cam plate 936B and a rear intermittent drive gear 936C, and effectively provides a central logic hub for the inhaler 901, advancing the various components of the inhaler 901 in a predetermined sequence. The ratchet component 940 is received in a recess in the rear side of the hub gear 936 so that movement of the mouthpiece cover during opening drives the hub gear 936 in the direction of arrow 934. During this rotation, a cam track 951 on the edge of the cam plate 936B engages the drive pin 962 of the peel beak component 990 to drive it vertically upwards. The engagement of the same drive pin 962 with a lower part of the cam track 951, with the peel beak component in a lowered position, resists counter rotation of the hub gear during closing of a mouthpiece cover.

Figure 92:
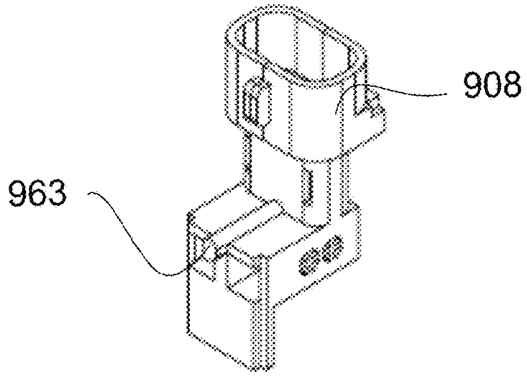
FIG. 92 shows a perspective view of a moving airway component from the inhaler of FIG. 90.
Figure 93:
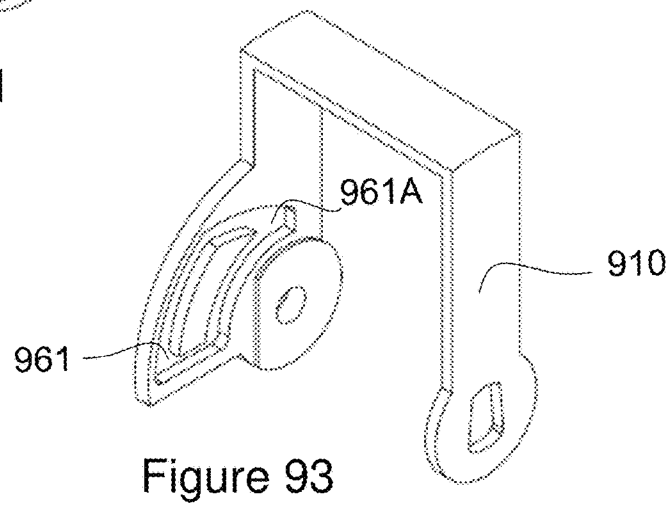
FIG. 93 shows a perspective view of a mouthpiece cover from the inhaler of FIG. 90.

FIG. 92 shows a moving airway 908 which is assembled with the moving peel beak component 990 to move therewith during use of the inhaler 901. The airway 908 comprises a further drive pin 963 which extends in an opposite direction to the drive pin 962 of the peel beak component 990 and engages, in use, with a further cam track 961 provided in an inner surface of the mouthpiece cover 910 shown in FIG. 93. The further cam track 961 includes an enlarged region 961A where the further drive pin 963 is received when the mouthpiece cover 910 is in its closed position.

Figure 94:
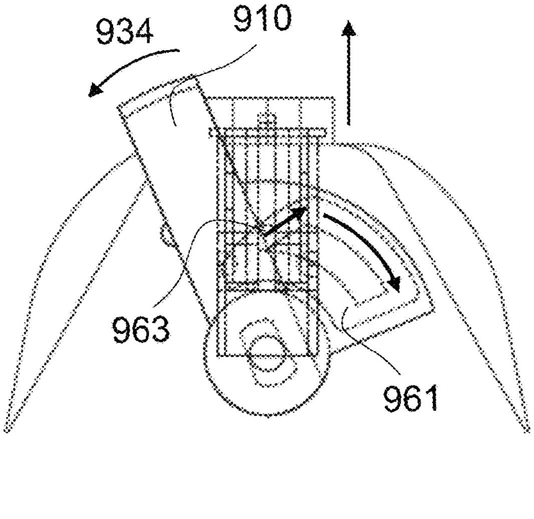
FIG. 94 shows the movement of the mouthpiece during opening of the mouthpiece cover.
Figure 95:
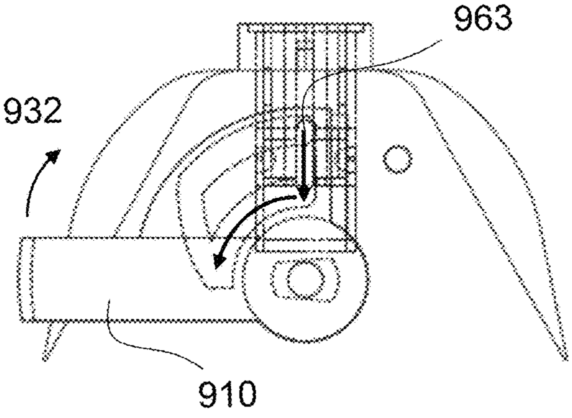
FIG. 95 shows the movement of the mouthpiece during closing of the mouthpiece cover.

The movement of the peel beak component 990 and airway 908 during movement of the mouthpiece cover 910 is further illustrated in FIGS. 94 and 95. FIG. 94 shows a point during the opening movement 934 where, as previously described, the peel beak component 990 (and connected airway 908) have been moved vertically upwards by the cam track 951 on the hub gear 936. Further rotation 934 of the mouthpiece cover 910 during opening causes the illustrated movement of the further drive pin 963 within the further cam track 961. This drives additional upwards movement of the airway 908, which is then held in elevated position as the mouthpiece cove 910 is fully opened.

FIG. 95 shows the mouthpiece cover 910 in a fully open position, at a commitment point for the inhaler device 901. From this position, the further drive pin 963 moves as indicated during rotation 932 of the mouthpiece cover 910 during closing. The airway 908 and peel beak component 990 are initially free to move vertically downwards, under a spring biasing force provided by the sprung take-up drums 930,930' which are charged by rotation of the hub gear 936 during opening, to perform a peeling operation. The peel beak component 990 is then held in a lower position, locking the hub gear against reverse rotation through engagement of its cam track 551 with the drive pin 962 of the peel beak component 990.

Figure 96:
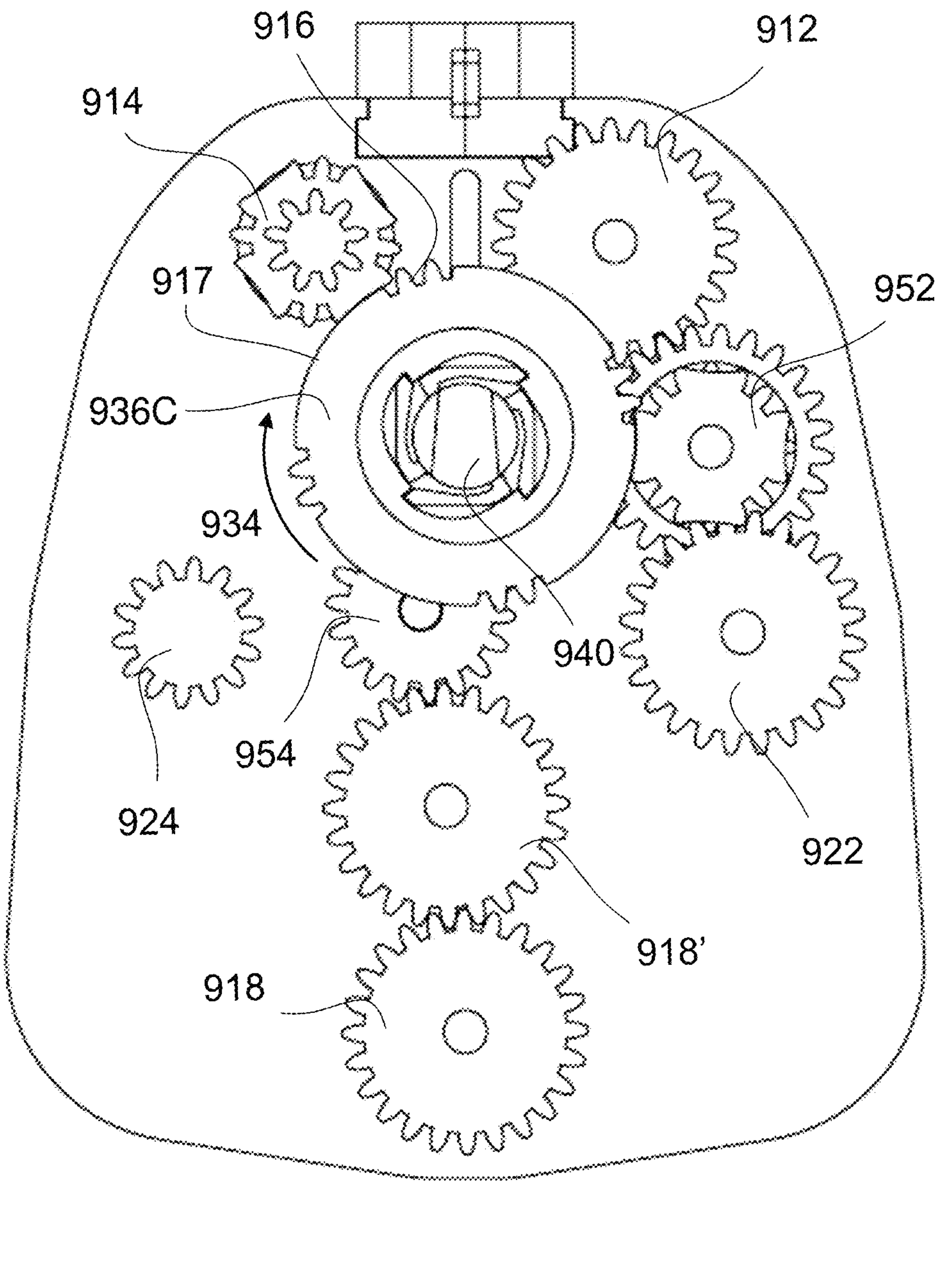
FIG. 96 shows the drive mechanism of the inhaler of FIG. 90.

FIG. 96 shows a rear view of the gearing of the inhaler 901. The ratchet component 940 is shown, and the drive direction 934 during opening of the mouthpiece cover is indicated.

Is should be clear that toothed sections 916 of the intermittent drive gear 936C will first advance the first indexer 912 (via the first idler gear 952) and then subsequently advance the second indexer 914. When the first and second indexers 912,914 are not being advanced, they are held stationary by Geneva style locking between smooth sections 917 of the intermittent drive gear 936C and the first idler 952 or second indexer 914. This is similar to the operation described for the sixth embodiment in FIG. 64. The ring gear 938 (see FIG. 90) transmits drive from the first and second indexers 912,914 to the first and second spool wheels 922,924 respectively via gear teeth provided on the interior of the ring gear 938. The ring gear 938 is indexed a tenth of a rotation per actuation, and could therefore be used as a dose counter or, with further development, the units wheel of the more complex dose counter mechanism. The drive gears 918,918' for the first and second take-up hubs 930,930' are driven constantly via the front drive gear 936A and second idler gear 954. This provides the required tension in a lid foil/sheet at the end of opening the mouthpiece cover 910, before the commitment point, ready for peeling, and spreads the work done by the user throughout the opening operation.

The previously described motion of the airway 908 and peel beak component 990 occurs during advancement of the first indexer 912 to prevent peeling of a first blister strip before a second blister strip is in the indexed position. This results in a lid foil/sheet of the second blister strip being overlaid (unspooled from the second take-up drum 930' prior to its motion and laid back over the base foil/sheet) and then recollected when indexed.

The design of the cam tracks 951,961 ensures that the airway 908 moves synchronously with the first blister strip motion and is held in the forwards position until the second blister strip has been indexed into position, before a simultaneous peeling operation is performed at the commitment point shown in FIG. 95.

The embodiments described above generally enables complex timing and sequencing to be provided with a low part-count, and provide inhalers that are tolerant of/resistant to misuse by a user without the need for a breath actuated mechanism. In many cases, the use of ratchets within the mechanism is largely avoided to minimise complex or confounding ratchet-timing issues that might otherwise prevent the device from recovering from deviations from the expected use-sequence and the concurrent indexing of two strips of medicament (where used) is avoided. The use of commitment points built into the mechanisms helps to address over-compliance issues.

It should be understood that, while the various embodiments described above provide their own individual features and benefits, they all achieve the same overall aim, namely disproportional progression of the opening system and indexing system of a single device during movement of the common actuator.

The invention claimed is:

1. An inhaler device comprising;

a chassis defining an interior chamber and an actuation mechanism within the interior chamber, the actuation mechanism comprising:

an indexing system comprising a first indexer for advancing a first medicament carrier and a second indexer for advancing a second medicament carrier; and a common actuator for controlling movement of the first and second indexers;

wherein the common actuator is movable between a first position, a second position, and an intermediate position between the first and second positions;

wherein the first medicament carrier and the second medicament carrier each separately comprises an elongate blister strip of medicament, and wherein progression of the first indexer is disproportional to progression of the second indexer.

2. The inhaler device according to claim 1, wherein the first indexer and the second indexer are not advanced simultaneously during movement of the common actuator.

3. The inhaler device according to claim 1, wherein movement of the common actuator through a first range of motion results in operation of the first indexer and movement of the common actuator through a second range of motion results in operation the second indexer, and wherein the first indexer is dissociated from the second indexer so that said first range of motion is not the same as said second range of motion.

4. The inhaler device according to claim 1, wherein the indexing system advances one of the first and second indexers as the common actuator is moved from said second position to said first position.

5. The inhaler device according to claim 1, wherein at least one of the first and second indexers comprises an index wheel.

6. The inhaler device according to claim 1, further comprising an opening system is configured to simultaneously peel open a blister on each of said first and second medicament carriers.

7. The inhaler device according to claim 1, wherein said intermediate position of the common actuator is closer to said second position of the common actuator than to said first position of the common actuator.

8. The inhaler device according to claim 7, wherein said intermediate position of the common actuator is adjacent said second position of the common actuator.

9. The inhaler device according to claim 1, wherein the indexing system comprises one or more gears with intermittent drive and/or locking surfaces.

10. The inhaler device according to claim 1, wherein the indexing system comprises a locking system for selectively preventing movement of one or more components of the indexing system.

11. The inhaler device according to claim 10, wherein the locking system comprises one or more gears with locking surfaces.

12. The inhaler device according to claim 10, wherein the locking system comprises one or more pawls.

13. The inhaler device according to claim 1, wherein the actuator comprises a mouthpiece cover.

14. The inhaler device according to claim 13, wherein the first position is a fully closed position of the mouthpiece cover.

15. The inhaler device according to claim 13, wherein the second position is a fully open position of the mouthpiece cover.

16. The inhaler device according to claim 1, further comprising a movable airway component.

17. The inhaler device according to claim 16, wherein the movable airway component comprises a unitary movable airway.

18. The inhaler device according to claim 16, wherein the inhaler comprises a split airway comprising a stationary airway component and the movable airway component.

19. The inhaler device according to claim 16, wherein the movable airway component provides a peel-beak component for regulating separation of a lidding sheet from the medicament carriers.

20. The inhaler device according to claim 16, wherein the movable airway component follows a path that is not substantially coincident with or merely offset from a path of the medicament carriers.

21. The inhaler device according to claim 16, wherein the movable airway component follows a substantially linear path.

22. The inhaler device according to claim 6, wherein the opening system peels the lidding sheet from the medicament carrier to completely open a blister.

* * * * *